United States Patent
Wallner et al.

(10) Patent No.: US 7,323,171 B2
(45) Date of Patent: *Jan. 29, 2008

(54) METHODS OF TREATING SKIN CONDITIONS USING INHIBITORS OF THE CD2/LFA-3 INTERACTION

(75) Inventors: Barbara P. Wallner, Cohasset, MA (US); Kevin D. Cooper, Ann Arbor, MI (US)

(73) Assignees: Astellas US LLC, Deerfield, IL (US); The Regents of the University of Michigan, Ann Arbor, MI (US)

( * ) Notice: Subject to any disclaimer, the term of this patent is extended or adjusted under 35 U.S.C. 154(b) by 463 days.

This patent is subject to a terminal disclaimer.

(21) Appl. No.: 10/778,373

(22) Filed: Feb. 13, 2004

(65) Prior Publication Data

US 2004/0136987 A1 Jul. 15, 2004

Related U.S. Application Data

(63) Continuation of application No. 09/730,465, filed on Dec. 5, 2000, now Pat. No. 6,764,681, which is a continuation-in-part of application No. 08/466,465, filed on Jun. 6, 1995, now Pat. No. 6,162,432, and a continuation-in-part of application No. PCT/US92/08755, filed on Oct. 6, 1992, which is a continuation-in-part of application No. 07/862,022, filed on Apr. 2, 1992, now abandoned, which is a continuation-in-part of application No. 07/770,969, filed on Oct. 7, 1991, now abandoned.

(51) Int. Cl.
*A61K 39/395* (2006.01)
*A61K 35/26* (2006.01)
*A61K 38/17* (2006.01)

(52) U.S. Cl. .............................. 424/154.1; 424/130.1; 424/133.1; 424/134.1; 424/135.1; 424/141.1; 424/143.1; 424/144.1; 424/152.1; 424/153.1; 424/172.1; 424/173.1; 424/185.1; 424/192.1; 514/2; 514/8; 514/15; 514/863; 514/885

(58) Field of Classification Search .................... None
See application file for complete search history.

(56) References Cited

U.S. PATENT DOCUMENTS

| | | | |
|---|---|---|---|
| 4,579,844 A | 4/1986 | Rovee et al. | |
| 4,681,760 A | 7/1987 | Fathman | |
| 4,738,297 A | 4/1988 | Takagi et al. | |
| 4,738,927 A | 4/1988 | Taniguchi et al. | |
| 4,816,397 A | 3/1989 | Boss et al. | |
| 4,816,567 A | 3/1989 | Cabilly et al. | |
| 4,833,092 A | 5/1989 | Geysen | |
| 4,956,281 A | 9/1990 | Wallner et al. | |
| 5,047,336 A | 9/1991 | Cate et al. | |
| 5,116,964 A | 5/1992 | Capon et al. | |
| 5,122,514 A | 6/1992 | Boger et al. | |
| 5,185,441 A | 2/1993 | Wallner et al. | |
| 5,190,859 A | 3/1993 | Dustin et al. | |
| 5,225,538 A | 7/1993 | Capon et al. | |
| 5,336,603 A | 8/1994 | Capon et al. | |
| 5,547,853 A | 8/1996 | Wallner et al. | |
| 5,556,943 A | 9/1996 | Yamashita et al. | |
| 5,565,335 A | 10/1996 | Capon et al. | |
| 5,728,677 A | 3/1998 | Wallner et al. | |
| 5,730,979 A | 3/1998 | Bazin et al. | 424/154.1 |
| 5,817,311 A | 10/1998 | Bazin et al. | 424/154.1 |
| 5,914,111 A | 6/1999 | Wallner et al. | |
| 5,928,643 A | 7/1999 | Wallner et al. | |
| 5,951,983 A | 9/1999 | Bazin et al. | 424/154.1 |
| 5,952,499 A | 9/1999 | Whittaker et al. | |
| 6,117,655 A | 9/2000 | Capon et al. | |
| 6,162,432 A | 12/2000 | Wallner et al. | |
| 6,270,766 B1 | 8/2001 | Feldman et al. | |
| 6,337,337 B1 | 1/2002 | Buck | |
| 6,384,198 B1 | 5/2002 | Diegel et al. | |
| 6,764,681 B2 * | 7/2004 | Wallner et al. | 424/154.1 |
| 2002/0009446 A1 | 1/2002 | Magilavy | |
| 2003/0044406 A1 | 3/2003 | Dingivan | |
| 2003/0185824 A1 | 10/2003 | Vaishnow et al. | |

FOREIGN PATENT DOCUMENTS

CA 2120500 4/1993

(Continued)

OTHER PUBLICATIONS

The Interferons: Basic Biology and Therapeutic Potential by Ezekowitz et al. in Therapeutic Immunology, edited by Austen et al., Blackwell Science, Cambridge, MA, 1996; see pgs. 249-263.*
Albert-Wolf et al., "Immunomodulatory Properties of Soluble Recombinant Human CD58 (LFA-3) Molecules" Develop. Biol. Standard vol. 77:87-92, 1992.
Capon et al., "Designing CD4 immunoadhesins for AIDS therapy," Nature 337:525-531 (1989).
Gregersen et al., "A CD4:immunoglobulin fusion protein with antiviral effects aganist HIV," Arch. Virol. 111:29-43 (1990).
Zettlmeissl et al, "Expression and characterization of human CD4:immunoglobulin fusion proteins," DNA and Cell Biol. 9:347-353 (1990).

(Continued)

*Primary Examiner*—Phillip Gambel
(74) *Attorney, Agent, or Firm*—Leydig, Voit & Mayer, Ltd

(57) ABSTRACT

Methods of using inhibitors of the CD2/LFA-3 interaction in treating skin conditions characterized by increased T cell activation and abnormal antigen presentation in the dermis and epidermis in mammals, including humans. Such conditions include psoriasis, UV damage, e.g., photoaging, atopic dermatitis, cutaneous T cell lymphoma such as mycosis fungoides, allergic and irritant contact dermatitis, lichen planus, alopecia areata, pyoderma gangrenosum, vitiligo, ocular cicatricial pemphigoid, and urticaria.

68 Claims, 7 Drawing Sheets

FOREIGN PATENT DOCUMENTS

| | | |
|---|---|---|
| CA | 1326940 | 2/1994 |
| CA | 1338078 | 2/1996 |
| EP | 0 200 412 A2 | 12/1986 |
| EP | 280 578 | 2/1988 |
| EP | 0 260 880 A2 | 3/1988 |
| EP | 0 314 317 B1 | 3/1989 |
| EP | 0 325 266 A2 | 7/1989 |
| EP | 0 345 466 A2 | 12/1989 |
| EP | 0 368 684 B2 | 5/1990 |
| EP | 0 503 646 A1 | 9/1992 |
| EP | 0 503 648 A1 | 9/1992 |
| EP | 0 517 174 B1 | 12/1992 |
| EP | 0 325 262 B1 | 3/1994 |
| EP | 0 626 447 A1 | 11/1994 |
| EP | 0 607 332 B1 | 12/1997 |
| EP | 1 637 155 A1 | 3/2006 |
| JP | 63-233917 T2 | 9/1988 |
| JP | 2-501113 T2 | 4/1990 |
| JP | 1-502875 T2 | 10/1990 |
| JP | 2-503269 T2 | 10/1990 |
| JP | 7-502495 T2 | 3/1995 |
| WO | WO 88/06592 A1 | 9/1988 |
| WO | WO88/07089 | 9/1988 |
| WO | WO 88/09820 A1 | 12/1988 |
| WO | WO 89/02922 A1 | 4/1989 |
| WO | WO89/07452 | 8/1989 |
| WO | WO 90/02181 | 3/1990 |
| WO | WO 90/07517 A1 | 7/1990 |
| WO | WO 90/08187 | 7/1990 |
| WO | WO90/09195 | 8/1990 |
| WO | WO 90/12099 A1 | 10/1990 |
| WO | WO91/07987 | 6/1991 |
| WO | WO91/10741 | 7/1991 |
| WO | WO 91/11194 A1 | 8/1991 |
| WO | WO 91/11461 A1 | 8/1991 |
| WO | WO 92/07581 A1 | 5/1992 |
| WO | WO 93/06852 A2 | 4/1993 |
| WO | WO 93/06866 A2 | 4/1993 |
| WO | WO 95/24217 A1 | 9/1995 |
| WO | WO 98/05357 A1 | 2/1998 |
| WO | WO 02/060480 A1 | 8/2002 |
| WO | WO 03/009740 A3 | 2/2003 |

OTHER PUBLICATIONS

Ellis et al., "Treatment of chronic plaque psoriasis by selective targeting of memory effector T lymphocytes," N. Engl. J. Med. 345:248-255 (2001).
U.S. Appl. No. 08/459,350, filed Jun. 2, 1995, Wallner et al.
Abraham et al., "Expression and Function of Surface Antigens on Scleroderma Fibroblasts" Arthritis and Rheumatism 34(9):1164-1172, 1991.
Altman et al., "Transfection of Genes For Cell Surface Products Involved in Antigen Presentation-Applications to the Understanding of Autoimmunity" Autoimmunity 7:213-220, 1990.
Baadsgaard et al., "Psoriac Epidermal Cells Demonstrate Increased Numbers and Function of Non-Langerhans Antigen-presenting Cells" J. Invest. Dermatol. 92:190-195; 1989.
Baadsgaard, O. et al., J. Invest. Dermat. 92(2): 190-195, 1989.
Barbosa et al. (1986) Gene Mapping and Somatic Cell Hybrid Analysis of the Role of Human Lymphocyte Function-Associated Antigen-3 (LFA-3) In CTL-Target Cell Interactions: J. Immunol. 136:3085-3091.
Bierer and Burakoff (1988) "T Cell Adhesion Molecules" FASEB J. 2:2584-2590.
Bierer et al. (1988) "Expression of the T-Cell Surface Molecule CD2 and an Epitope-Loss CD2 Mutant to Define the Role of Lymphocyte Function-Associated Antigen 3 (LFA-3) in T-Cell Activation" Proc. Natl. Acad. Sci. USA 85:1194-1198.
Bierer et al. (1989) "A Monoclonal Antibody to LFA-3, the CD2 Ligand, Specifically Immobilizes Major Histocompatibility Complex Proteins" Eur. J. Immunol. 19:661-665.
Bockenstedt et al. (1988) "The CD2 Ligand LFA-3 Activates T Cells But Depends on the Expression and Function of the Antigen Receptor" J. Immunol. 141:1904-1911.
Bromberg et al. (1991) "Anti-CD2 Monoclonal Antibodies Alter Cell-Mediated Immunity In Vivo" Transplantation 51:219-225.
Brown et al. (1987) T2.2 Characterization of CD2 Epitopes By Western Blotting: in Leukocyte Typing III, A.J. McMichael (ed.) Oxford, England: Oxford University Press, 110-112.
Brown et al. (1989) "The CD2 Antigen Associates With The T-Cell Antigen Receptor CD3 Antigen Complex on the Surface of Human T Lymphocytes" Nature 339:551-553.
Chang et al. (1992) "T-Cell Activation is Potentiated by Cytokines Released by Lesional Psoriatic, but not Normal, Epidermis" Arch. Dermatol. 128:1478.
Chin, Y.H. et al. J. Invest. Dermatol. 93(2) Supplemental: 82S-87S (1989).
Clayton et al. (1987) "Murine and Human T11 (CD2) cDNA Sequences Suggest a Common Signal Transduction Mechanism" Eur. J. Immunol. 17: 1367-1370.
Conti and Cosimi (1990) "Effect of Monoclonal Antibodies on Primate Allograft Rejection" Crit. Rev. Immunol. 10(2): 113-130.
Cooper (1990) "Immunoregulation in the Skin" Current Problems in Dermatology 19:69-80.
Cooper (1992) "Skin-infiltrating Lymphocytes in Normal and Disordered Skin: Activation Signals and Functional Roles in Psoriasis and Mycosis Fungoides-type Cutaneous T Cell Lymphoma" J. Dermatol. 19:731-737.
Cooper et al. (1985) Effects of ultraviolet radiation on human epidermal cell alloantigen presentation; initial depression of langerhans cell-dependent function is followed by appearance of T6-Dr+ cells that enhance epidermal alloantigen presentation: J. Immunol. 134: 129-137.
Cunningham and Harris (1992) Antibody engineering—how to be human: TIBTECH 10:112-113.
Curtis and Barnes (1992) "The Nature of Science" in Biology, 5th ed. (Worth Publishers, Inc.): 14-15.
Denning et al. (1987) Monoclonal Antibodies to CD2 and Lymphocyte Function-Associated Antigen 3 Inhibit Human Thymic Epithelial Cell-Dependent Cell-Dependent Mature Thymocyte Activation: J. Immunol. 139: 2573-2578.
Denning et al. (1988) "Purified Lymphocyte Function-Associated Antigen-3 (LFA-3) Activates Human Thymocytes Via the CD2 Pathway" J. Immunol. 141: 2980-2985.
Dustin et al. (1987) "Purified Lymphocyte Function-Associated Antigen 3 Binds to CD2 and Mediates T Lymphocyte Adhesion" J. Exp. Med. 165: 677-692.
Dustin et al. (1987) "T Cell Activation By LFA-3 and CD2 Antibodies" FASEB J. 45: A1239 (Abstract No. 5484).
Gonzalez-Ramos et al. (1992) "APC-Targeted Immunointervention in Psoriasis: Blockafe of LFA-3-CD2 and ICAM 1-LFA1 Ligand Pairing Blocks Autoreactivity to Lesional Epidermis" Clinical Research 40(2):500A.
Harris and Emery (1993) "Therapeutic antibodies—the coming of age" TIBTECH 11: 42-44.
Haynes, B.F. et al. Arthritis and Rheum. 31 (8): 947-955 (1988).
Howard et al. (1981) A human T lymphocyte differentiation defined by monoclonal antibodies that block E-rosette formation: J. Immunol. 126:2117-2122.
Hughes et al. (1990) "Endothelial Cells Augment T Cell Interleukin 2 production by a Contact-Dependent Mechanism involving CD2/LFA-3 Interaction" J. Exp. Med. 171:1453-1467.
Hughes et al. (1990) "The Endothelial Cell as a Regulator of T-Cell Function" Immunol. Rev. 117, 85-102.
Kaplan et al. (1987) "Distribution and Turnover of Langerhans Cells During Delayed Immune Responses in Human Skin" J. Exp. Med. 165:763-776.
Koyasu et al. (1990), "Role of Interaction of CD2 Molecules with Lymphocyte Function-Associated Antigen 3 In T-Cell Recognition of Norminal Antigen" Proc. Natl. Acad. Sci. USA 87: 2603-2607.

Krensky (1990) "The Human Cytolytic T Lymphocyte Response to Transplantation Antigens" Rediatric Res. 19: 1231-1234.

Krensky et al. (1983) "The Functional Significance, Distribution, and Structure of LFA-1, LFA-2, and LFA-3: Cell Surface Antigens Associated With CTL-Target Interactions" J. Immunol. 131:611-616.

Krensky et al. (1984) "Human Lymphocyte Function Associated Antigens" Surv. Immunol. Res. 3:39-44.

Larson and Springer (1990) "Structure and function of leukocyte integrins" Immunol. Revs. 114:181-217.

Le et al. (1987) "Anti-LFA-3 Monoclonal Antibody Induced Interleukin 1 (IL 3) Release by Thymic Epithelial (TE) Cells and Monocytes" FASEB J. 46(3):447 Abstract 761.

Le et al. (1990) "Ligan Binding to the LFA-3 Cell Adhesion Molecule Inducces II-1 Production By Human Thymic Epithelial Cells" J. Immunol. 144:4541-4547.

Makgoba et al. (1989) "The CDA2-LFA-3 and LFA-1-ICAM Pathways: Relevance to T-Cell Recognition" Immunol. Today 10:417-422.

Makgoba, M. et al., Immunol. Today 10 (12): 417-422 (1989).

Martz and Gromkowski (1985) "Lymphocyte Function-Associated Antigens: Regulation of Lymphocyte Adhesions In Vitro and immunity In Vivo" Adv. Exp. Med.Biol. 184:291-310.

Matis (1990) "The molecular basis of T-cell specificity" Ann. Rev. Immunol. 8:65-82.

Meuer et al. (1984) "An Alternative Pathway of T Cell Activation: A Functional Role for the 50 kd T11 Sheep Erythrocyte Receptor Protein" cell 36:897-906.

Meuer et al. (1984) "The human T-cell receptor" Ann. Rev. Immunol. 2:23-50.

Meuer et al. (1989) "The Alternative Pathway of T Cell Activation: Biology, Pathophysiology, and Perspectives for Immunopharmacology" Clin. Immunol. Immunopath. 50:S133-S138.

Miller (1993) "Specific Interactin of Lymphocyte Functin-associated Antigen 3 with CD2 Can Inhibit T Cell Responses" J. Exp. Med. 178:211-222.

Moingeon et al. (1989) "The Structural Biology of CD2" Immunol. Rev. 111:111-144.

Moingeon et al. (1991) "Complementary Roles for CD2 and LFA-1 Adhesion Pathways During T Cell Activation" Eur. J. Immunol. 21:605-610.

Nathan et al. (1986) "Local and Systemic Effects of Intradermal Recombinant Interferon-y in Patients with Lepromatous Leprosy" New Eng. J. Med. 315(1):6-15.

Nouri et al. (1990) "Selective and non-selective loss of immunoregulatory molecules (HLA-A,B,C antigens and LFA-3) in transitional cell carcinoma" J. Br. Cancer 62:603-606.

Osband et al. (1990) "Problem in the investigational Study and Clinical Use of Cancer Immunotherapy" Immunology today 11(6): 193-195.

Pepino et al. (1989) "Primate Cardiac Allo- and Xenotransplantation: Modulation of the Immune Response with Photochemotherapy" Eur. Surg. Res. 21:105-113.

Peterson and Seed (1987) "Monoclonal Antibody And Ligand Binding Sites of the T Cell Erythrocyte Receptor (CD2)" Nature 329:842-846.

Picker et al. (1990) "A Unique Phonotype of Skin-associated Lymphocytes in Humans" Am. J. Path. 136(5);1053-1068.

Poizot-Martin et al. (1991) "Are CD4 antibodies and peptide T new treatments for psoriasis" The Lancet 337:1477.

Prince (1989) "Requirement for both the CD3/T Cell Receptor Complex and the CD2/Lymphocyte Function-Associated Antigen-3 Adhesion System in Monocyte-Independent T Cell Activation By Oxidized Erthrocytes" Immunol. Investigations 18:1081-1093.

Prinz et al. (1991) "Chimaeric CD4 monoclonal antibody in treatment of generalised pustular psoriasis" The Lancet 338:320-321.

Recny et al. (1990) "Structural and Functional Characterization of the CD2 Immunoadhesion Domain" J. Biol. Chem. 263:8542-8549.

Rincon and Patarroyo (1989) "Effect of Antibodies From the T Cell (CD2'Only) and the NK/Non-Lineage (New Panel Only) Sections on Adhesion of Jurkat (T) Cell to Human Erythrocytes" Tissue Antigens 33:285.

Sanders et al. (1988) "T Cell Adhesion Receptors LFA-1 and CD2 and Their Ligands ICAM-1 and LFA-3" Analysis in Adhesion, Cell Mediated Lysis, and as Markers of T Cell Subsets in The T-Cell Receptor, A.R. Liss. Inc., pp. 269-279.

Sayre et al. (1987) "Molecular cloning and expression of T11 cDNAs reveal a receptor-like structure on human T lymphocytes" Chemical Abstracts 107(15): Abstract 128218x.

Schopf (1986) "Stimulation of T Cells by Autologous Molecular Leukocytes and Epidermal Cells in Psoriasis" Arch. Dermatol. Res. 279:89-94.

Seed and Aruffo (1987) "Molecular Cloning of the CD2 Antigen, The T-Cell Erythrocyte Receptor, By a Rapid immunoselection procedure" Proc. Natl. Acad. Sci. USA 84:3365-3369.

Selvaraj et al. (1987) "The T Lymphocyte Glycoprotein CD2 (LFA-2/T11/E-Rosette Receptor) Binds the Cell Surface Ligand LFA-3" FASEB J. 46(3):447 Abstract 760.

Sewell et al. (1986) "Molecular Cloning of the Human T-Lymphocyte Surface CD2 (T11) Antigen" Proc. Natl. Acad. Sci. USA 83:8717-8722.

Shaw et al. (1986) "Two Antigen-Independent Adhesion Pathways Used by Human Cytotoxic T-Cell Clones" Nature 323:262-264.

Simon et al. (1991) "Adhesion molecules CD11a, CD18, and ICAM-2 on Human Epidermal Lagerhans Cells Serve a Functional Role in the Activation of Alloreactive T Cells" Soc. Invest. Dermat. 96: 148-151.

Singer et al. (1990) "Thymocyte LFA-1 and Thymic Epithelial Cell ICAM-1 Molecules Mediate Binding of Activated Human Thymocytes to Thymic Epithelial Cells" J. Immunol. 144:2931-2939.

Singer, K.H. et al. J. Invest. Dermatol. 94 (6) Supplement: 85S-90S.

Smith and Thomas (1990) "Cellular Expression of Lyphocyte Function Associated Antigens and the Intercellular Adhesion Molecule-1 in Normal Tissue" J. Clin. Path. 45:893-900.

Springer (1990) "Adhesion Receptors of the Immune System" Nature 346:425-434.

Springer et al. (1987) "The Lymphocyte Function-Associated LFA-1, CD2, and LFA-3 Molecules: Cell Adhesion Receptors of the Immune System" Ann. Rev. Immunol. 5:223-252.

Stauton et al. (1989) "Molecular characterization of ICAM-1 and ICAM-2; Alternate Ligands for LFA-1" Tissue Antigens 33:287.

Stedman's Medical Dictionary, (1976) The Williams & Wilkens Company, BAltimore, MD, p. 810.

Suranyi et al. (1991) "Lymphocyte Adhesion Molecules in T Cell-Mediated Lysis of Human Kidney Cells" Kidney International 39:312-319.

Tadini (1989) "Adhesion Molecules Expression in Psoriasis" J. Invest. Dermatol. 93(2):309A.

Tang and Udey (1991) "Inhibition of Epidermal Langerhans Cell Function by Low Dose of Ultraviolet B Radiation" J. Immunol. 145:3347-3355.

Ullman et al. (1990) "Transmission of Signals from T Lymphocyte Antigen Receptor to the Genes Respondible for Cell Proliferation and Immune Function: The Missing Link" Ann. Rev. Immunol. 8:421-452.

Valdimarsson et al. (1986) "Psoriasis: a disease of abnormal keratinocyte proliferation induced by T lymphocytes" Immunol. Today 7:256-259.

van Seventer et al. (1989) "The Three LFA-3 Specific Monoclonal Antibodies in the Non-Lineage panel of Workshop Monoclonal Antibodies All Inhibit T-Cell Rosetting" Tissue Antigens 33:298.

Virella et al. (1988) "The Interaction of CD2 With Its LFA-3 Ligand Expressed By Autologous Erythrocytes Results in Enhancement of B Cell Responses" Cell. Immunol. 116:308-319.

Vollger et al. (1987) "Thymocyte Binding to Human Tymic Epithelial Cells is Inhibited by Monoclonal Antibodies to CD-2 and LFA-3 Antigens" *J. Immunol.* 138:358-363.

Waldmann (1991) "Monoclonal Antibodies in Diagnosis and Therapy," *Science* 252:1657-1662.

Wallner et al (1987) "Primary Structure of Lymphocyte Function-Associated Antigen 3 (LFA-3)-The Ligand of the Lymphocyte CD2 Glycoprotein" *J. Exp. Med.* 166:923-932.

Webb et al. (1990) "LFA-3, CD44, and CD45: Physiologic Triggers of Human Monocyte TNF and IL-1 Release" Science 249:1295-1297.

Winter and Harris (1993) "Humanized antibodies" TiPS 14:139-142.

Yong and Khwaja (1990) "Leukocyte Cellular Adhesion Molecules" Blood Reviews 4:211-225.

Zheng et al. (1990) "Expression of Intercellular and Adhesion Molecule-1 and Lyphocyte Function-Associated Antigen-3 on Human Thyroid Epithelial Cells in Graves'and Hashimoto's Disease" J. Autoimmunity 3:727-736.

Actis, et al., "Continuosly Infused Cyclosporine at Low Dose Is Sufficient to Avoid Emergency Colectomy in Acute Attacks of Ulcerative Colitis Without in Asute Attacks of Ulcerative Colitis Without the Need for High-Dose Steroids", *Journal of Clinical Gastroenterology*, vol. 17,No. 1, pp. 10-13, 1993.

Adams, "How the Immune System Works and Why it Causes Autoimune Deseases" *Immunology Today*,1996.

Alcover, et al., "Interdependence of CD3-Ti and CD2 Activation Pathways in Human T Lyphocytes, " *The EMBo Journal*, vol. 7, No. 7, pp. 1973-1977, 1988.

Alora, et al., "Narrow-band (311 nm) UVB Phototherapy: An Audit of the First Year's experience at the Massachusetts General Hospital", *Photodermatology Photoimmunology & Photomedicine*, vol. 13, pp. 82-84, 1997.

Altmeyer, et al., Traitement Systemique Du Psoriasis Par Les Derives De L'Acide Fumarique, *Ann. Dermatol. Venereol*, vol. 123, pp. 838-841, 1996.

Altschuler, "Implications of Psoriasis as a New Disease", *Dermatology*, vol. 199, pp. 1-2, 1999.

Arbuckle, et al., "Psoriasis" *Pediatrics in Review*, 1998.

Arellano, "Risk of Cancer with Cyclosporine in Psoriasis" *International Journal of Dermatology*, vol. 36, No. 1, pp. 15-17, 1997.

Arend, "The Pathophysiology and Treatment of Rheumatoid Arthritis" *Arthritis & Rheumatism*, vol. 40, No. 4, pp. 595-597, 1997.

Armitage, "Tests for Linear Trends in Proportions and Frequences" *Biometrics*, 1955.

Asadullah, et al., IL-10 is a Key Cytokine in Psoriasis, *Journal of Clinical Investigation*, vol. 101, No. 4, pp. 783-794, 1998.

Ashcroft, et al., "Clinical Measures of Disease Severity and Outcome in Psoriasis:A Critical Appraisal of their Quality" *British Journal of Dermatology*, vol. 141, pp. 185-191, 1999.

Bangha, et al., "Evaluation of Topical Antipsoriatic Treatment by Chromametry, Visiometry and 20-MHz Ultrasound in the Psoriasis Plaque Test", *Skin Pharmacology*, vol. 9, pp. 298-306, 1996.

Bansil, et al. "Multiple Sclerosis: Immune Mechanism and Update on Current Therapies" *Annals of Neurology*, vol. 37, pp. 87-101, 1995.

Bardolph, "psoriasis: A Review of Present and Future Management", *Nursing Standard*, vol. 12, No. 21, pp. 43-47, 1998.

Barker, "The Pathophysiology of Psoriasis", *The Lancet*, vol. 338, pp. 227-230, 1991.

Barker, et al., "Leukocycte-Endothelium Interactions in Cutneous Inflammatory Process", *Springer Seminars in Immunopathology*, vol. 13, pp. 355-367, 1992.

Barker, et al., "Topical Maxacalcitol for the Treatment of *Psoriasis vulgaris* : A Placebo-Controlled, Double-Blind, Dose-Finding Study with Active Comparator", *British Journal of Dermatology*, vol. 141, pp. 274-278, 1999.

Barsoum, "Introduction of Stable High-Copy-Number DNA into Chinese Hamster Ovary Cells by Electroporation" *DNA and Cell Biology*, vol. 9, No. 4, pp. 293-300, 1990.

Bay, et al., "psoriasis Patients have T-cells with Reduced Responsiveness to Common Mycobacterial Antigens", FEMS *Immunology and MEdical Microbiology*, vol. 21, pp. 65-70, 1998.

Bell, et al. "CD2 and the Regulation of T Cell Anergy", *The Journal of Immunology*, pp. 2805-2807, 1995.

Bennett, "Cyclosporine Nephrotoxicity: Implications for Dermatology", *International Journal of Dermatology*, vol. 36, pp. 11-14, 1997.

Berth-Jones, et al., "Treatment of Psoriasis with Intermittent Short Course Cyclosporin (Neoral® ). A Multicentre Study", *British Journal of Dermatology*, vol. 136, pp. 527-530, 1997.

Bjerke, et al., "Acitretin Versus Etretinate in Severe Psoriasis. A double-blind Randomized Nordic Multicenter Study in 168 Patients", *Acta Derm Venereol Suppl* (Stockh), vol. 146, pp. 206-207, 1989.

Bjerrring, et al., "Topical Treatment of Psoriatic Skin with Methotrexate Cream: A Clinical, Pharmacokinetic, and Histological Study", *Acta Derm Venereol (Stockh)*, vol. 66, pp. 515-519, 1986.

Boehncke, et al., "Differential Expression of Adhesion Molecules on Infiltrating Cells Inflammatory Dermatoses", *Journal of American Academy of Dermatology*, vol. 26, No. 6, pp. 907-913, 1992.

Bonifati, et al., "Recognition and Treatment of Psoriasis: Special Considerations in Elderly Patients" *Drugs& Aging*, vol. 12, No. 3, pp. 177-190, 1998.

Borroni, et al., "Evidence for CD8+ Cell Increase in Long-Term PUVA-Treated Psoriatic Patients after PUVA Discontinuation", *Dermatology*, vol. 185, pp. 69-71, 1992.

Bos, et al., "Immunologie in de Medische Praktijk. VII. Psoriasis", *Ned Tijdschr Geneeskd*, vol. 141, No. 48, pp. 2334-2338, 1997.

Bouhnik, et al., "Long- term Follow-up of Patients with Crohn's Disease Treated with Azathioprine or 6-Mercaptopurine", *The Lancet*, vol. 347, pp. 215-219, 1996.

Brottier, et al., "T Cell Activation Via CD2 [T, gp50] Molecules: Accessory Cells are Required to Trigger T Cell Activation via CD2-D66 Plus CD2-9.6/T11$_1$ Epitopes[1] ", *The Journal of Immunology*, vol. 135, pp. 1624-1631, 1985.

Buccheri, et al., "Acitretin Therapy is Effective for Psoriasis Associated with Human Immunodeficiency Virus Infection", *Archives of Dermatology*, vol. 133, pp. 711-715, 1997.

Burden, "Management of Psoriasis in Childhood", *Clinical and Experimental Dermatology*, vol. 24, pp. 341-345, 1999.

Burns, et al., "Intralesional Cyclosporine for Psoriasis", *Archives of Dermatology*, vol. 128, pp. 786-790, 1992.

Camisa, et al., "Psoriasis", *Blackwell Scientific Publications*, 1994.

Chandraratna, "Tazarotene: The First Receptor-Selective Topical Retinoid for the Treatment of Psoriasis", *American Academy of Dermatology*, vol. 37, No. 2, pp. S12-S17, 1997.

Chisholm, et al., "The Effects of an Immunomodulatory LFA3-IgG$_1$ Fusion Protein on Nonhuman Primates", *Therapeutic Immunology*, vol. 1, pp. 205-216, 1994.

Cristiansen, et al., "Etretinate (Tigason® ) and Betamethasone Valerate (Celeston Valerate® ) in the Treatment of Psoriasis", *Dermatologica*, vol. 165, pp. 204-207, 1982.

Christophers, et al., "Cyclosporine in Psoriasis: A Multicenter Dose-Finding Study in Severe Plaque Psoriasis", *Therapy, Journal of the American Academy of Dermatology*, vol. 26, No. 1, pp. 876-90, 1992.

Christophers, et al., "The Inflammatory Infiltrate in Psoriasis", *Clinics in Dermatology*, vol. 13, pp. 131-135, 1995.

Cohen, et al., "Immunomodulatory Agents and Other Medical Therapies in Inflammatory Bowel Disease" *Current Opinion in Gastroenetrology*, vol. 11, pp. 321-330, 1995.

Colten, et al., "Pulmonary Inflammation-A Balancing Act", *The New England Journal of Medicine*, pp. 1094-1096, 1997.

Crispe, et al., "Strange Brew: T Cells in the Liver" *Immunology Today*, vol. 17, No. 11, pp. 522-525, 1996.

Cronstein, "The Mechanism of Action of Methotrexate", *Rheumatic Disease Clinics of North America*, vol. 23, No. 4, pp. 739-755, 1997.

Danielian, et al., "The Tyrosine Kinase Activity of p56$^{lck}$ is Increase in Human T Cell Activated vai CD2", *European Journal of Immunology*, vol. 21, pp. 1967-1970, 1991.

Davies, et al., "Physiological Parameters in Laboratory Animals and Humans" *Pharmaceutical Research*, vol. 10, No. 7, pp. 1093-1095, 1993.

Dawe, et al., "Narrow-Band (TL-01) Ultraviolet B Phototherapy for Chronic Plaque Psoriasis: Three Times of Five Times Weekly Tratment?" *British Journal of Dermatology*, vol. 1, No. 38, pp. 833-839, 1998.

Department of Health & Human Services, "International Conference on Harmonisation" *Federal Register*, vol. 62, No. 222, pp. 61515-61519, 1997.

Ding et al. (1996) "A novel murine model for the assessment of human CD2-related reagents In Vivo," *J. Immunol.* 157(5): 1863-1869.

Dinowitz, et al., "Recent Studies on Retrovirus-Like Particles in Chinese Hamster Ovary Cells", *Developments in Biological Standardizations*, vol. 76, pp. 201-207, 1991.

Drake, et al., "Guidelines of Care for Psoriasis", *Journal of American Academy of Dermatology*, vol. 28, No. 4, pp. 632-637, 1993.

Driscoll, et al., "Structure of Domain 1 of Rat T Lymphocyte CD2 Antigen", *Nature*, vol. 353, pp. 762-765, 1991.

Dustin, et al., "T-Cell Receptor Cross-Linking Transiently Stimulates Adhesiveness Through LFA-1" *Nature*, vol. 341, pp. 619-624, 1989.

Dustin, et al., "Role of Lymphocyte Adhesion Receptors in Transient Interaction and Cell Locomotion" *Annual Review of Immunology*, vol. 27, pp. 27-66, 1991.

Dustin, et al., "Low Affinity Interaction of Human or Rat T Cell Adhesion Molecule CD2 with Its Ligand Aligns Adhering Membranes to Achieve High Physiological Affinity", *The Journal of Biological Chemistry* vol. 272, No. 49, pp. 30889-30898, 1997.

Dustin, et al., "Corelation of CD2 Binding and Functional Properties of Multimeric Lymphocyte Function-Associated Antigen 3" *Journal of Experimental Medicine*, vol. 169, pp. 503-517, 1989.

Dustin, et al., "Anchoring Mechanisms for LFA-3 Cell Adhesion Glycoprotein at Membrane Surface", *Nature*, vol. 329, 846-848, 1987.

Duvic, et al., "Molecular Mechanisms of Tazarotene Action in Psoriasis", *Journal of American Academy of Dermatology*, vol. 37, No. 2, pp. S18-S24, 1997.

Economidou, et al., "Effects of Cyclosporin A on Immune Activation Markers in Patients with Active Psoriasis", *Dermatology*, vol. 199, pp. 144-148, 1999.

Edelhoch, "Spectroscopic Determination of Tryptophan and Tyrosine in Proteins" *Biochemistry*, vol. 6, No. 7, pp. 1948-1954, 1967.

Ehmann, et al., "Effect of Oral Synthetic Retinoids on Keratinizing Disordes", *Journal of American Academy of Dermatology*, vol. 6, No. 4, pp. 692-696, 1982.

Ekborn, et al., "Crohn's Disease After In-Utero Measles Virus Exposure", *The Lancet*, vol. 348, pp. 515-517, 1996.

Elder, et al., "Efficacy and Pharmacokinetics of Two Formulations of Cycloporine A in Patients with Psoriasis" *Journal of Clinical Pharmacology*, vol. 35, pp. 865-875, 1995.

Ellis, et al., "Cyclosporine for plaque-Type Psoriasis: Results of a Multidose, Double-Blind Trial", *The New England Journal of Medicine* vol. 324, No. 5, pp. 276-284, 1991.

Ewe,et al., "Azathioprine and Prednisolone for Active Crohn Disease", *ACP Journal Club*, 1994.

Farber, "Juvenile Psoriasis: Early Interventions Can Reduce Risks for Problems Later" *Postgraduate Medicine* vol. 103, No. 4, pp. 89-100, 1998.

Farber, et al. "Psoriasis: A Disease of the Total Skin" *Journal of American Academy of Dermatology*, vol. 12, pp. 150-156, 1985.

Faulds, et al., "Cyclosporin: A Review of its Pharmacodynamic and Pharmacokinetic Properties, and Therapeutic Use in Immunoregulatory Disorders", *Drugs*, vol. 45, No. 6, pp. 953-1040, 1993.

Feagan, et al., "Methotrexate for the Treatment of Crohn'Disease" *The New England Journal of Medicine*, vol. 332, pp. 292-297, 1995.

Feagan, et al., "Therapeutics and Inflammatory Bowel Disease: A Guide to the Interpretation of Radomized Controlled Trials" *Gastroenterology*, vol. 110, pp. 275-283, 1996.

Feagan, et al., "Methotrexate Improved Symptoms in Chronic Active Crohn Disease", *ACP Journal Club*, 1995.

Feldman, et al., "The Economic Impact of Psoriasis Increases with Psoriasis Severity" *Journal of American Academy of Dermatology*, vol. 37, pp. 564-569, 1997.

Feldman, et al., "The Self-Administered Psoriasis Area and Severity Index Is Valid and Reliable", *Journal of Investigative Dermatology*, vol. 106, pp. 183-186, 1996.

ffrench-Constant, "Pathogenesis of Multiple Sclerosis", *The Lancet*, vol. 343, pp. 272-278, 1994.

Finlay, et al., Dermatology Life Quality Index (DLQI): A Simple Practical Measure for Routine Clinical Use, *Clinical and Experimenttal Dermatology*, vol. 19, pp. 210-216, 1993.

Finzi, et al., "A Clinical Survey of Psoriasis in Italy: $1^{st}$ AISP Report" *Journal of the European Academy of Dermatology and Venereology*, vol. 10,pp. 125-129, 1998.

Finzi, et al., "Cyclosporine versus Etretinate: Italian Multicenter Comparative Trial in Severe Plaque-Form Psoriasis", *Dermatology*, vol. 187, pp. 8-18, 1993.

Fleischer,Jr., et al., "Patient Measurement of Psoriasis Disease Severity with a Structures Instrument" *Journal of Investigative Dermatology*, vol. 102, No. 6, pp. 967-969, 1994.

Fleischer,Jr., et al., "Disease Severity Measures in a Population of Psoriasis Patients: The Symptoms of Psoriasis Correlate with Self-Administered Psoriasis Area Severity Index Scores", *Journal of Investigative Dermatology*, vol. 107, No. 1, pp. 26-29, 1996.

Fortune, et al., "Quality of Life in Patient with Psoriasis: the Contribution of Clinical Variables and Psoriasis-Specific Stress", *British Journal of Dermatology*, vol. 137, pp. 755-760, 1997.

Fox, "The Role of T Cells in the Immunopathogenesis of Rheumatoid Arthritis", *Arthritis & Rheumatism*, vol. 40, No. 4, pp. 598-609, 1997.

Georgouras, et al. "Systemic Treatment of Severe Psoriasis", *Australasian Journal of Dermatology*, vol. 38, pp. 171-182, 1997.

Gismondi, et al., "Triggering through CD16 or Phorbol Esters Enhances Adhesion of NK Cells to Laminin via Very Late Antigen 6", *Journal of Experimental Medicine*, vol. 176,pp. 1251-1257, 1992.

Goebell, et al., "Drug Trials in Inflammatory Bowel Diseases 1993-1995: A Survey Conducted by the IOIBD", *Inflammatory Bowel Disease*, vol. 2, pp. 265-267, 1996.

Goldman, et al., "OKT3-Induced Cytokine Release Attenuation by High-Dose MethilPrednisolone", *The Lancet*, pp. 802-803, 1989.

Gollnick, et al., "Acitretin* versus Etretinate in Psoriasis: Clinical and Pharmacokinetic Results of a German Multicenter Study", *Journal of American Academy of Dermatology*, vol. 19, No. 3, pp. 458-468, 1988.

Gollob, et al., "CD2 Regulates Responsivenes of Activated T Cells to Interleukin 12", *Journal of Experimental Medicine*, vol. 182, pp. 721-731, 1995.

Gottlieb, "The Challenges of Treating Moderate to Severe Psoriasis", *International Journal of Dermatology*, vol. 36, pp. 41-44, 1997.

Greaves, et al., "Treatment of Psorisis", *The New England Journal of Medicine*, vol. 332, No. 9, pp. 581-588, 1995.

Greenberg, et al., "Oral Budesonide for Active Chrohn's Disease", *The New England Journal of Medicine*, vol. 331, No. 13, pp. 836-845, 1994.

Grossman, et al., "Long-term Safety of Cyclosporine in the Treatment of Psoriasis", *Archives of Dermatology*, vol. 132, pp. 623-629, 1996.

Grossman, et al., "A Novel Therapeutic Approach to Psoriasis with Combination Calcipotriol Ointment and Very- Low-Dose Cyclosporine: Results of a Multicenter Placebo-Controlled Study", *Journal of American Academy of Dermatology*, vol. 31, No. 1, pp. 68-74, 1994.

Guckian, et all., "Immunomodulation at the Initiation of Phototherapy and photochemotherapy", *Photodermatology, Photoimmunology & Photomedicine*, vol. 11, pp. 163-169, 1995.

Gulliver, et al., Increased Bioavailability and Improved Efficacy, in Sever Psoriasis, of a New Microemulsion Formulation of Cyclosporin*, *British Journal of Dermatology*, vol. 135, pp. 35-39, 1996.

Guzzo, "Recent Advances in the Treatment of Psoriasis", *Dermatologic Clinics*, vol. 15, No. 1, pp. 59-68, 1997.

Hamblin, "From Dendritic Cells to Tumour Vaccines", vol. 347, pp. 705-706, 1996.

Hanauer, "Inflammatory Bowel Disease", *Drug Therapy*, vol. 334, No. 13, pp. 841-848, 1996.

Hanauer, "Medical Therapy of Ulcerative Colitis" *The Lancet*, vol. 342, pp. 412-417, 1993.

Hardman, et al., "Active Psoriasis and Profound CD4+Lymphocytopenia", *British Journal of Dermatology*, vol. 136, pp. 930-932, 1997.

Hawke, et al., "Autoimune T Cells in Myasthenia Gravis: Heterogeneity and Potential for Specific Immunotargeting", *Immunology Today*, vol. 17, No. 7, pp. 307-311, 1996.

Henseler, "The Genetics of Psoriasis", *Journal of American Academy of Dermatology*, vol. 37, No. 2, pp. S1-S11, 1997.

Henseler,et al., "Disease Concomitance in Psoriasis", *Journal of American Academy of Dermatology*, vol. 32, pp. 982-986.

Henseler,et al., "Psoriasis of Early and Late Onset: Characterization of Two Types of *Psoriasis vulgaris*", *Journal of American Academy of Dermatology*, vol. 13, No. 3, pp. 450-456, 1985.

Herbin, et al., "Automated Registration of Dissimilar Images: Application to Medical Imagery", *Computer Vision, Graphics, and Image Processing*, vol. 47, pp. 77-88, 1989.

Hiramine, et al., "Differential Effect of Cyclosporine in Vivo on the Distribution of T cell Subsets in the Thymus, Spleen, and Lymph Nodes", *Transplatation*, vol. 47, No. 3, pp. 499-503, 1989.

Hirano, et al., "Individual Pharmacodynamics Assessed by Antilymphocyte Action Predicts Clinical Cyclosporine Efficacy in Psoriasis", *Clinical Pharmacology & Therateutics*, vol. 63, No. 4, pp. 465-470, 1998.

Ho, et al., "Intermittent Short Courses of Cyclosporin (Neoral® ) for Psoriasis Unresponsive to Topical Therapy: A 1-Year Multicentre, Randomized Study", *British Journal of Dermatology*, vol. 141, pp. 283-291, 1999.

Honeyman, et al., "Low-Dose Cyclosporine a Improves Severe Disabling Psoriasis in Latin America", *International Journal of Dermatology*, vol. 34, pp. 583-588, 1995.

Hopkins, et al., "Adouble-Blind Controlled Trial of Etretinate (Tigason) and Ibuprofen in Psoriatic Arthritis", *Annals of the Rheumatic Diseases*, vol. 44, pp. 189-193, 1985.

Hugot, et al., "Mapping of a Susceptibility Locus for Crohn's Disease on Chromosome 16", *Nature*, vol. 379, pp. 821-823, 1996.

Hunt, et al., "Generalized Pustular Psoriasis Responsive to PUVA and Oral Cyclosporin Therapy", *Australasian Journal of Dermatology*, vol. 38, pp. 199-201, 1997.

Ieiri, et al., "Evaluation of the Therapeutic Range of Whole Blood Cyclosporin Concentration in the Treatment of Psoraisis", *International Journal of Clinical Pharmacology and Therateutics*, vol. 34, No. 3, pp. 106-111, 1996.

Ikemizu, et al., "Crystal Structure of the CD2-Binding Domain of CD58 (Lymphocite Function-Associated Antigen 3) at 1.8-ÅResolution", *Proceedings of the National Academy of Science*, vol. 96, pp. 4289-4294, 1999.

Ip, et al., Structural Characterization of the N-Glycans of a Humanized Anti-CD18 Murine Immunoglobulin G, *Archives of Biochemistry and Biophysics*, vol. 308, No. 2, pp. 387-399, 1994.

Isaacs, et al., "Humanized *Anti-CD4 Monoclonal Antibody Therapy of Autoimmune and Inflammatory Disease*", *Clinical and Experimental Immunology*, vol. 110, pp. 158-166, 1997.

Jefferies, et al., Glycosylation of Antibody Molecules: Structural and Functional Significance, *Chemical Immunology*, vol. 65, pp. 111-113, 1997.

Jemec, et al., "The Applicability of Clinical Scoring Systems: SCORAD and PASI in Psoriasis and Atopic Dermatits", *Acta Derm Venereol (Stockholm)*, vol. 77, pp. 392-393, 1997.

Jenkins, et al., "CD28 Delivers A Constimulatory Signal Involved in Antigen-Specific IL-2 Production by Human T Cells", *The Journal of Immunology*, vol. 147, pp. 2461-2466, 1991.

Johnson, "On Teaching Dermatology to Nondermatologists", *Arch Dermatol*, vol. 130, pp. 850-852, 1994.

Jones, et al., "Crystal Structure at 2.8ÅResolution of a Soluble Form of the Cell Adhesion Molecule CD2" *Nature*, vol. 360, pp. 232-239,1992.

June, "Increases in Tyrosine Phosphorylation are Detectable Before Phospholipase C Activation After T Cell Receptor Stimulation", *The Journal of Immunology*, vol. 144, No. 5, pp. 1591-1599, 1990.

Majeau et al. (1994), "Mechanism of lymphocyte function-associated molecule 3-Ig fusion proteins inhibition of T cell responses," J. of Immunol. 15: 2753-2767.

Meier et al (1995) "Immunomodulation by LFA3TIP, an LFA-3/ IgG$_1$ fusion protein: cell line dependent glycosylation effects on pharmacokinetics and pharmacodynamic markers," *Therapeutic Immunology* 2: 159-171.

Moingeon et al. (1989), "CD2-mediated adhesion facilitates T lymphocyte antigen recognition function," *Nature* 339: 312-339.

Osborn et al. (1995), "Amino acid residues required for binding of lymphocyte function-associated antigen 3 (CD58) to its counter-receptor CD2," *J. Exp. Med.* 181(1): 429-434.

Pepinsky et al. (1991), "The increased potency of cross-linked lymphocyte function-associated antigen-3 (LFA-3) multimers is a direct consequence of changes in valency," *J. Biol Chem.* 266(27): 18244-18249.

Riggs et al. (1996), "The pharmacokinetic/pharmacodynamic (PK/PD) modeling of immunoglobin fusion protein, LFA3TIP, using a non-linear saturable cell activity model," *Pharmaceutical Research* 13 (9 Supp.):s398.

Savage et al. (1991), "Endothelial cell lymphocyte function-associated antigen-3 and an unidentified ligand act in concert to provide costimulation to human peripherial blood CD4* T cells," *Cellular Immunology* 137: 150-163.

Semnani et al. (1994), "Costimulation by purified intercellular adhesion molecule 1 and lymphocyte function-associated antigen 3 induces distinct proliferation, cytokine and cell surface antigen profiles in human "naïve" and "memory" CD4* T cells," *J. Exp. Med.* 180: 2125-2135.

(Editors) (1990) "Adhesion Molecules in Diagnosis and Treatment of Inflammatory Disease" *The Lancet* 336:1351-1352.

Abraham et al. (1990) Interactions Between Lymphocytes and Dernal Fibroblasts: An In Vitro Model of Cutaneous Lymphocyte Trafficking *Exp. Cell. Res.* 190:118-126.

Neuberger et al., "recombinant antibodies possessing novel effector functions", 1984, Nature, vol. 312;604-608.

Traunecker et al., "A novel approach for preparing anti-T cell . . . ", 1986, Eur. J. Immunol., vol. 16;851-854.

Gascoigne et al., "Secreation of a chimeric T-cell . . . ", 1987, P.N.A.S. USA, vol. 84;2936-2940.

Traunecker et al., "Soluble CD4 molecules neutralize . . . ", 1988, Nature, vol. 331;84-86.

The Merck Manual of Diagnosis and Therapy, sixteenth edition, edited by Berkow et al., Merck Research Lab., Rahway NJ 1992, pp. 2435-2445.

Actis, et al., "Continuously Infused Cyclosporine at Low Dose Is Sufficient to Avoid Emergency Colectomy in Acute Attacks of Ulcerative Colitis Without the Need for High-Dose Steroids", *Journal of Clinical Gastroenterology*, vol. 17,No. 1, pp. 10-13, 1993.

Adams, "How the Immune System Works and Why it Causes Autoimmune Diseases" *Immunology Today*, Jul. 1996;17(7):300-2.

Alcover, et al., "Interdependence of CD3-Ti and CD2 Activation Pathways in Human T Lymphocytes", *The EMBO Journal*, vol. 7, No. 7, pp. 1973-1977, 1988.

Alora, and Taylor, "Narrow-band (311 nm) UVB Phototherapy: An Audit of the First Year's experience at the Massachusetts General Hospital", *Photdermatology Photoimmunology & Photomedicine*, vol. 13, pp. 82-84, 1997.

Altmeyer, and Nuchel, "Traitment Systemique Du Psoriasis Par Les Derives De L'Acide Fumarique", *Ann. Dermatol. Venereol*, vol. 123, pp. 838-841, 1996.

Altschuler, "Implications of Psoriasis as a New Disease", *Dermatology*, vol. 199, pp. 1-2, 1999.

Arbuckle, and Hartley, "Psoraisis" *Pediatrics in Review*, Mar. 1998; 19(3):106-7.

Arellano, "Risk of Cancer with Cyclosporine in Psoriasis" *International Journal of Dermatology*, vol. 36, No. 1, pp. 15-17, 1997.

Arend, "The Pathophysiology and Treatment of Rheumatoid Arthritis" *Arthritis & Rheumatism*, vol. 40, No. 4, pp. 595-597, 1997.

Armitage, "Tests for Lineat Trends in Proportions and Frequencies" Biometrics, 11, 375-386, 1955.

Asadullah, et al., IL-10 Is a Key Cytokine in Psoriasis, *Journal of Clinical Invetigation*, vol. 101, No. 4, pp. 783-794, 1998.

Ashcroft, et al., "Clinical Measures of Disease Severity and Outcome in Psoriasis:A Critical Appraisal of their Quality" *British Journal of Dermatology*, vol. 141, pp. 185-191, 1999.

Bangha, and Elsner, "Evaluation of Topical Antipsoriatic Treatment by Chromametry, Visiometry and 20-MHz Ultrasound in the Psoriasis Plaque Test", *Skin Pharmacology*, vol. 9, pp. 298-306, 1996.

Bansil, et al. "Multiple Sclerosis: Immune Mechanism and Update on Current Therapies" *Annals of Neurology*, vol. 37, pp. 87-101, 1995.

Bardolph, and Ashton, "Psoriasis: A Review of Present and Future Management", *Nursing Standard*, vol. 12, No. 21, pp. 43-47, 1998.

Barker, "The Pathophysiology of Psoriasis", *The Lancet*, vol. 338, pp. 227-230, 1991.

Barker, and Nickoloff, "Leukocyte-Endothelium Interactions in Cutaneous Inflammatory Processes", *Springer Seminars in Immunopathology*, vol. 13, pp. 355-367, 1992.

Barker, et al., "Topical Maxacalcitol for the Treatment of *Psoriasis vulgaris* : A Placebo-Controlled, Double-Blind, Dose-Finding Study with Active Comparator", *British Journal of Dermatology*, vol. 141, pp. 274-278, 1999.

Barker, "Psoriasis" *Journal of the Royal College of Physicians of London*, vol. 31, No. 3, pp. 238-240, 1997.

Barsoum, "Introduction of Stable High-Copy-Number DNA into Chinese Hamster Ovary Cells by Electroporation" *DNA and Cell Biology*, vol. 9, No. 4, pp. 293-300, 1990.

Bay, et al., "Psoriasis Patients have T-cells with Reduced Responsiveness to Common Mycobacterial Antigens", FEMS *Immunology and Medical Microbiology*, vol. 21, pp. 65-70, 1998.

Bell, and Imboden, "CD2 and the Regulation of T Cell Anergy", *J Immunol.* 1995 Sep. 15;155(6):2805-7.

Bennett, "Cyclosporine Nephrotoxicity: Implications for Dermatology", *International Journal of Dermatology*, vol. 36, pp. 11-14, 1997.

Berth-Jones, et al., "Treatment of Psoriasis with Intermittent Short Course Cyclosporin (Neoral® ). A Multicentre Study", *British Journal of Dermatology*, vol. 136, pp. 527-530, 1997.

Bjerke, and Geiger, "Acitretin Versus Etretinate in Severe Psoriasis. A double-blind Randomized Nordic Multicenter Study in 168 Patients", *Acta Derm Venereol Suppl* (Stockh), vool. 146, pp. 206-207, 1989.

Bjerring, et al., "Topical Treatment of Psoriatic Skin with Methotrxate Cream: A Clinical, Pharmacokinetic, and Histological Study", *Acta Derm Venereol (Stockh)*, vol. 66, pp. 515-519, 1986.

Boehncke, et al., "Differential Expression of Adhesion Molecules on Infiltrating Cells Inflammatory Dermatoses", *Journal of American Academy of Dermatology*, vol. 26, No. 6, pp. 907-913, 1992.

Bonifati, et al., "Recognition and Treatment of Psoriasis: Special Considerations in Elderly Patients" *Drugs & Aging*, vol. 12, No. 3, pp. 177-190, 1998.

Borroni, et al., "Evidence for CD8+ Cell Increase in Long-Term PUVA-Treated Psoriatic Patients after PUVA Discontinuation", *Dermatology*, vol. 185, pp. 69-71, 1992.

Bos, and Rie, "Immunologie in de Medische Praktijk. VII. Psoriasis", *Ned Tijdschr Geneeskd*, vol. 141, No. 48, pp. 2334-2338, 1997.

Bouhnik, et al., "Long- term Follow-up of Patients with Crohn's Disease Treated with Azathioprine or 6-Mercaptopurine", *The Lancet*, vol. 347, pp. 215-219, 1996.

Brottier, et al., "T Cell Activation Via CD2 [T, gp50] Molecules: Accessory Cells are Required to Trigger T Cell Activation via CD2-D66 Plus CD2-9.6/T11, Epitopes[1] ", *The Journal of Immunology*, vol. 135, pp. 1624-1631, 1985.

Buccheri, et al., "Acitretin Therapy is Effective for Psoriasis Associated with Human Immunodeficiency Virus Infection", *Archives of Dermatology*, vol. 133, pp. 711-715, 1997.

Burden, "Management of Psoriasis in Childhood", *Clinical and Experimental Dermatology*, vol. 24, pp. 341-345, 1999.

Burns, et al., "Intralesional Cyclosporine for Psoriasis", *Archives of Dermatology*, vol. 128, pp. 786-790, 1992.

Camisa, *Psoriasis, Blackwell Scientific Publications*, 1994, 1st Ed.

Chandraratna, "Tazarotene: The First Receptor-Selective Topical Retinoid for the Treatment of Psoriasis", *American Academy of Dermatology*, vol. 37, No. 2, pp. S12-S17, 1997.

Christiansen, et al., "Etretinate (Tigason® ) and Betamethasone Valerate (Celeston Valerate® ) in the Treatment of Psoriasis", *Dermatologica*, vol. 165, pp. 204-207, 1982.

Christophers, et al., "Cyclosporine in Psoriasis: A Multicenter Dose-Finding Study in Severe Plaque Psoriasis", *Therapy, Journal of the American Academy of Dermatology*, vol. 26, No. 1, pp. 876-90, 1992.

Christophers, and Mrowietz, "The Inflammatory Infiltrate in Psoriasis", *Clinicas in Dermatology*, vol. 13, pp. 131-135, 1995.

Cohen, and Hanauer, "Immunomodulatory Agents and Other Medical Therapies in Inflammatory Bowel Disease" *Current Opinion in Gastroenetrology*, vol. 11, pp. 321-330, 1995.

Colten, and Krause, "Pulmonary Inflammation-A Balancing Act", N Engl J Med. Apr. 10, 1997;336(15):1094-6.

Crispe, and Mehal, "Strange Brew: T Cells in the Liver" *Immunology Today*, vol. 17, No. 11, pp. 522-525, 1996.

Cronstein, "The Mechanism of Action of Methotrexate", *Rheumatic Disease Clinics of North America*, vol. 23, No. 4, pp. 739-755, 1997.

Danielian, et al., "The Tyrosine Kinase Activity of p56$^{lck}$ is Increased in Human T Cells Activated via CD2", *European Journal of Immunology*, vol. 21, pp. 1967-1970, 1991.

Davies, and Morris, "Physiological Parameters in Laboratory Animals and Humans" *Pharmaceutical Research*, vol. 10, No. 7, pp. 1093-1095, 1993.

Dawe, et al., "Narrow-Band (TL-01) Ultraviolet B Phototherapy for Chronic Plaque Psoriasis: Three Times of Five Times Weekly Treatment?" *British Journal of Dermatology*, vol. 1, No. 38, pp. 833-839, 1998.

Department of Health & Human Services, "International Conference on Harmonisation" *Federal Register*, vol. 62, No. 222, pp. 61515-61519, 1997.

Dinowitz, et al., "Recent Studies on Retrovirus-Like Particles in Chinese Hamster Ovary Cells", *Developments in Biological Standardizations*, vol. 76, pp. 201-207, 1991.

Drake, et al., "Guidelines of Care for Psoriasis", *Journal of American Academy of Dermatology*, vol. 28, No. 4, pp. 632-637, 1993.

Driscoll, et al., "Structure of Domain 1 of Rat T Lymphocyte CD2 Antigen", *Nature*, vol. 353, pp. 762-765, 1991.

Dustin, and Springer, "T-Cell Receptor Cross-Linking Transiently Stimulates Adhesiveness Through LFA-1" *Nature*, vol. 341, pp. 619-624, 1989.

Dustin, and Springer, "Role of Lymphocyte Adhesion Receptors in Transient Interaction and Cell Locomotion" *Annual Review of Immunology*, vol. 27, pp. 27-66, 1991.

Dustin, et al., "Low Affinity Interaction of Human or Rat T Cell Adhesion Molecule CD2 with its Ligand Aligns Adhering Membranes to Achieve High Physiological Affinity", *The Journal of Biological Chemistry* vol. 272, No. 49, pp. 30889-30898, 1997.

Dustin, et al., "Correlation of CD2 Binding and Functional Properties of Multimeric and Monomeric Lymphocyte Function-Associated Antigen 3" *Journal of Experimental Medicine*, vol. 169, pp. 503-517, 1989.

Dustin, et al., "Anchoring Mechanisms for LFA-3 Cell Adhesion Glycoprotein at Membrane Surface", *Nature*, vol. 329, 846-848, 1987.

Duvic, et al., "Molecular Mechanisms of Tazarotene Action in Psoriasis", *Journal of American Academy of Dermatology*, vol. 37, No. 2, pp. S18-S24, 1997.

Economidou, et al., "Effects of Cyclosporin A on Immune Activation Markers in Patients with Active Psoriasis", *Dermatology*, vol. 199, pp. 144-148, 1999.

Edelhoch, "Spectroscopic Determination of Tryptophan and Tyrosine in Proteins" *Biochemistry*, vol. 6, No. 7, pp. 1948-1954, 1967.

Ehmann, and Voorhees, "Effect of Oral Synthetic Retinoids on Keratinizing Disorders", *Journal of American Academy of Dermatology*, vol. 6, No. 4, pp. 692-696, 1982.

Ekbom, et al., "Crohn's Disease After In-Utero Measles Virus Exposure", *The Lancet*, vol. 348, pp. 515-517, 1996.

Elder, et al., "Efficacy and Pharmacokinetics of Two Formulations of Cyclosporine A in Patients with Psoriasis" *Journal of Clinical Pharmacology*, vol. 35, pp. 865-875, 1995.

Ellis, et al., "Cyclosporine for Plaque-Type Psoriasis: Results of a Multidoes, Double-Blind Trial", *The New England Journal of Medicine* vol. 324, No. 5, pp. 276-284, 1991.

Ewe,et al., "Azathioprine and Prednisolone for Active Crohn Disease", *ACP Journal Club*, 1994, Annals of Internal Medicine 120/2 SUPPL. 1 (13).

Farber, "Juvenile Psoriasis: Early Interventions Can Reduce Risks for Problems Later" *Postgraduate Medicine* vol. 103, No. 4, pp. 89-100, 1998.

Farber, et al. "Psoriasis: A Disease of the Total Skin" *Journal of American Academy of Dermatology*, vol. 12, pp. 150-156, 1985.

Faulds, et al., "Cyclosporin: A Review of its Pharmacodynamic and Pharmacokinetic Properties, and Therapeutic Use in Immunoregulatory Disorders", *Drugs*, vol. 45, No. 6, pp. 953-1040, 1993.

Feagan, et al., "Methotrexate for the Treatment of Crohn's Disease" *The New England Journal of Medicine*, vol. 332, pp. 292-297, 1995.

Feagan, et al., "Therapeutics and Inflammatory Bowel Disease: A Guide to the Interpretation of Randomized Controlled Trials" *Gastroenterology*, vol. 110, pp. 275-283, 1996.

Feagan, et al., "Methotrexate Improved Symptoms in Chronic Active Crohn Disease", *ACP Journal Club*, 1995, Jul.-Aug.; 123 (1) 9.

Feldman, et al., "The Economic Impact of Psoriasis Increase with Psoriasis Severity" *Journal of American Academy of Dermatology*, vol. 37, pp. 564-569, 1997.

Feldman, et al., "The Self-Administered Psoriasis Arear and Severity Index Is Valid and Reliable", *Journal of Investigative Dermatology*, vol. 106, pp. 183-186, 1996.

ffrench-Constant, "Pathogenesis of Multiple Sclerosis", *The Lancet*, vol. 343, pp. 272-278, 1994.

Finlay, and Khan, "Dermatology Life Quality Index (DLQI): A Simple Practical Measure for Routine Clinical Use", *Clinical and Experimental Dermatology*, vol. 19, pp. 210-216, 1993.

Finzi, et al., "A Clinical Survey of Psoriasis in Italy: $1_{st}$ AISP Report" *Journal of the European Academy of Dermatology and Venerology*, vol. 10,pp. 125-129, 1998.

Finzi, et al., "Cyclosporin versus Etretinate: Italian Multicenter Comparative Trial in Severe Plaque-Form Psoriasis", *Dermatology*, vol. 187, pp. 8-18, 1993.

Fleischer,Jr., et al., "Patient Measurement of Psoriasis Disease Severity with a Structured Instrument" *Journal of Investigative Dermatology*, vol. 102, No. 6, pp. 967-969, 1994.

Fleischer,Jr., et al., "Disease Severity Measures in a Population of Psoriasis Patients: The Symptoms of Psoriasis Correlate with Self-Administered Psoriasis Area Severity Index Scores", *Journal of Investigative Dermatology*, vol. 107, No. 1, pp. 26-29, 1996.

Fortune, et al., "Quality of Life in Patient with Psoriasis: the Contribution of Clinical Variables and Psoriasis-Specific Stress", *British Journal of Dermatology*, vol. 137, pp. 755-760, 1997.

Fox, "The Role of T Cells in the Immunopathogenesis of Rheumatoid Arthritis", *Arthritis & Rheumatism*, vol. 40, No. 4, pp. 598-609, 1997.

Georgouras, et al. "Systemic Treatment of Severe Psoriasis", *Australasian Journal of Dermatology*, vol. 38, pp. 171-182, 1997.

Gismondi, et al., "Triggering through CD16 or Phorbol Esters Enhances Adhesion of NK Cellls to Laminin via Very Late Antigen ;", *Journal of Experimental Medicine*, vol. 176,pp. 1251-1257, 1992.

Goebell, et al., "Drug Trials in Inflammatory Bowel Diseases 1993-1995: A Survey Conducted by the IOIBD", *Inflammatory Bowel Diseases*, vol. 2, pp. 265-267, 1996.

Goldman, et al., "OKT3-Induced Cytokine Release Attenuation by High-Dose MethilPrednisolone", Lancet. Sep. 30, 1989;2(8666):802-3.

Gollnick, et al., "Acitretin* versus Etretinate in Psoriasis: Clinical and Pharmacokinetic Results of a German Multicenter Study", *Journal of American Academy of Dermatology*, vol. 19, No. 3, pp. 458-468, 1988.

Gollob, et al., "CD2 Regulates Responsiveness of Activated T Cells to Interleukin 12", *Journal of Experimental Medicine*, vol. 182, pp. 721-731, 1995.

Gottlieb, "The Challenges of Treating Moderate to Severe Psoraisis", *International Journal of Dermatology*, vol. 36, pp. 41-44, 1997.

Greaves, and Weinstein, "Treatment of Psoriasis", *The New England Journal of Medicine*, vol. 332, No. 9, pp. 581-588, 1995.

Greenberg, et al., "Oral Budesonide for Active Chrohn's Disease", *The New England Journal of Medicine*, vol. 331, No. 13, pp. 836-845, 1994.

Grossman, et al., "Long-term Safety of Cyclosporine in the Treatment of Psoriasis", *Archives of Dermatology*, vol. 132, pp. 623-629, 1996.

Grossman, et al., "A Novel Therapeutic Approach to Psoriasis with Combination Calcipotriol Ointment and Very- Low-Dose Cycloporine: Results of a Multicenter Placebo-Controlled Study", *Journal of American Academy of Dermatology*, vol. 31, No. 1, pp. 68-74, 1994.

Guckian, et all., "Immunomodulation at the Initiation of Phototherapy and photochemotherapy", *Photodermatology, Photoimmunology & Photomedicine*, vol. 11, pp. 163-169, 1995.

Gulliver, et al., Increased Bioavailability and Improved Efficacy, in Severe Psoriasis, of a New Microemulsion Formulation of Cyclosporin*, *British Journal of Dermatology*, vol. 135, pp. 35-39, 1996.

Guzzo, "Recent Advances in the Treatment of Psoriasis", *Dermatologic Clinics*, vol. 15, No. 1, pp. 59-68, 1997.

Hamblin, "From Dendritic Cells to Tumour Vaccines", vol. 347, pp. 705-706, 1996.

Hanauer, "Inflammatory Bowel Disease", *Drug Therapy*, vol. 334, No. 13, pp. 841-848,1996.

Hanauer, "Medical Therapy of Ulcerative Colitis" *The Lancet*, vol. 342, pp. 412-417, 1993.

Hardman, et al., "Active Psoriasis and Profound $CD4^+$Lymphocytopenia", *British Journal of Dermatology*, vol. 136, pp. 930-932, 1997.

Hawke, et al., "Autoimmune T Cells in Myasthenia Gravis: Heterogeneity and Potential for Specific Immunotargeting", *Immunology Today*, vol. 17, No. 7, pp. 307-311, 1996.

Henseler, "The Genetics of Psoriasis", *Journal of American Academy of Dermatology*, vol. 37, No. 2, pp. S1-S11, 1997.

Henseler, and Christophers, "Disease Concomitance in Psoriasis", *Journal of American Academy of Dermatology*, vol. 32, pp. 982-986, 1997.

Henseler, and Christophers, "Psoriasis of Early and Late Onset: Characterization of Two Types of *Psoriasis vulgaris*", *Journal of American Academy of Dermatology*, vol. 13, No. 3, pp. 450-456, 1995.

Herbin, et al., "Automated Registration of Dissimilar Images: Application to Medical Imagery", *Computer Vision, Graphics, and Iamge Processing*, vol. 47, pp. 77-88, 1989.

Hiramine, et al., "Differential Effect of Cyclosporine in Vivo on the Distribution of T cell Subsets in the Thymus, Spleen, and Lymph Nodes", *Transplatation*, vol. 47, No. 3, pp. 499-503, 1989.

Hirano, et al., "Individual Pharmacodynamics Assessed by Antilymphocyte Action Predicts Clinical Efficacy in Psoriasis", *Clinical Pharmacology & Therateutics*, vol. 63, No. 4, pp. 465-470, 1998.

Ho, et al., "Intermittent Short Courses of Cyclosporine (Neoral® ) for Psoriasis Unresponsive to Topical Therapy: A 1-Year Multicentre, Randomized Study", *British Journal of Dermatology*, vol. 141, pp. 283-291, 1999.

Honeyman, et al., "Low-Dose Cyclosporine a Improves Severe Disabling Psoriasis in Latin America", *International Journal of Dermatology*, vol. 34, pp. 583-588, 1995.

Hopkins, et al., "A double-Blind Controlled Trial of Etretinate (Tigason) and Ibuprofen in Psoriatic Arthritis", *Annals of the Rheumatic Diseases*, vol. 44, pp. 189-193, 1985.

Hugot, et al., "Mapping of a Susceptibility Locus for Crohn's Disease on Chromosome 16", *Nature*, vol. 379, pp. 821-823, 1996.

Hunt, et al., "Generalized Pustular Psoriasis Responsive to PUVA and Oral Cyclosporin Therapy", *Australasian Journal of Dermatology*, vol. 38, pp. 199-201, 1997.

Ieiri, et al., "Evaluation of the Therapeutic Range of Whole Blood Cyclosporin Concentration in the Treatment of Psoriasis", *International Journal of Clinical Pharmacology and Therateutics*, vol. 34, No. 3, pp. 106-111, 1996.

Ikemizu, et al., "Crystal Structure of the CD2-Binding Domain of CD58 (Lymphocyte Function-Associated Antigen 3) at 1.8-Å Resolution", *Proceedings of the National academy of Science*, vol. 96, pp. 4289-4294, 1999.

Ip, et al., Structural Characterization of the N-Glycans of a Humanized Anti-CD18 Murine Immunoglobulin G, *Archives of Biochemistry and Biophysics*, vol. 308, No. 2, pp. 387-399, 1994.

Isaacs, et al., "Humanized *Anti-CD4 Monoclonal Antibody Therapy of Autoimmune and Inflammatroy Disease*", *Clinical and Experimental Immunology*, vol. 110, pp. 158-166, 1997.

Jefferis, and Lund, "Glycosylation of Antibody Molecules: Structural and Functional Significance", *Chemical Immunology*, vol. 65, pp. 111-113, 1997.

Jemec, and Wulf, "The Applicability of Clinical Scoring Systems: SCORAD and PASI in Psoriasis and Atopic Dermatitis", *Acta Derm Venereol (Stockholm)*, vol. 77, pp. 392-393, 1997.

Jenkins, et al., "CD28 Delivers a Constimulatory Signal Involved in Antigen-Specific IL-2 Production by Human T Cells", *The Journal of Immunology*, vol. 147, pp. 2461-2466, 1991.

Johnson, "On Teaching Dermatology to Nondermatologists", *Arch Dermatol*, vol. 130, pp. 850-852, 1994.

Jones, et al., "Crystal Structure at 2.8Å Resolution of a Soluble Form of the Cell Adhesion Molecule CD2" *Nature*, vol. 360, pp. 232-239, 1992.

June, "Increases in Tyrosine Phosphorylation are Detectable Before Phospholipase CActivation After T Cell Receptor Stimulation", *The Journal of Immunology*, vol. 144, No. 5, pp. 1591-1599, 1990.

Kang, et al., "Calcipotriene-Induced Improvement in Psoriasis is Associated with Reduced Interleukin-8 and Increased Interleukin-10 levels within Lesions", *British Journal of Dermatology*, vol. 138, pp. 77-83, 1998.

Kanner, et al., "CD2/LFA-3 Ligation Induces Phospholipase-C$\gamma$ 1 Tyrosine Phosphorylation and Regulates CD3 Signaling", *The Journal of Immunology*, vol. 148, No. 7, pp. 2023-2029, 1992.

Kantor, et al., "Double-Blind Bilateral paired Comparison of 0.05% Halobetasol Propionate Cream and its Vehicle in Patients with Chronic Atopic Dermatitis and Other Eczematous Dermatoses", *Jouranl of the American Academy of Dermatology*, vol. 25, No. 6, pp. 1184-1186, 1991.

Kato, et al., "CD48 is a Counter-Receptor for Mouse CD2 and is Involved in T Cell Activation", *Journal of Experimental Medicine*, vol. 176, pp. 1241-1249, 1992.

Kaufman, and Sharp, "Amplication and Expression of Sequences Contransfected with a Modular Dihydrofolate Reductase Complementary DNA Gene", *Journal Molecular Biology*, vol. 159, pp. 601-621, 1982.

Kaufman, and Sharp, "Construction of a Molecular Dihydrofolate Reductase cDNA Gene: Analysis of Signals Utilized for Efficient Expression", *Molecular and Cellular Biology*, vol. 2, No. 11, pp. 1304-1319, 1982.

Kelso, Th1 and TH2 Subsets: Paradigms Lost?, *Immunology Today*, vol. 16, No. 8, pp. 374-379, 1995.

Killeen, et al., "The MRC OX-45 Antigen of Rat Leukocytes and Endothelium is in a Subset of the Innunoglobulin Superfamily with CD2, LFA-3 and Carcinoembryonic Antigens", *The EMBO Journal*, vol. 7, No. 10, pp. 3087-3091, 1988.

Kingston, et al., "Etretin Therapy for Severe Psoriasis", *Arch Dermatol*, vol. 123, pp. 55-58, 1987.

Kollias, "Letter to the Editor: Simple Changes to PUVA Phototherapy May Minimize the Photocarcinogenic Risks", *Photodermatology, Photoimmunology, & Photomedicine*, vol. 15, pp. 205, 1999.

Koo, "Neoral in Psoriasis Therapy: Toward a New Perspective", *International Journal of Dermatology*, vol. 36, pp. 25-29, 1997.

Koo, "Systematic Sequential Therapy of Psoriasis; A New Paradigm for Improved Therapeutic Results", *Journal of the American Academy of Dermatology*, vol. 41, No. 3, pp. S25-S28, 1999.

Koo, "Population-Based Epidemiological Study of Psoriasis with Emphasis on Quality of Life Assessment", *Psychodermatology*, vol. 14, No. 3, pp. 485-496, 1996.

Koo, et al., "Mometasone Furoate 0.1%-Salicylic Acid 5% Ointment Versus Mometasone Furoate 0.1% Ointment in the Treatment of Moderate-to-Severe Psoriasis: A Multicenter Study", *Clinical Therapeutics*, vol. 20, No. 2, pp. 283-291, 1998.

Koshy, et al., "Increased Expression of CD40 Ligand on Systemic Lupus Erthematosus Lymphocytes", *Journal of Clinical Investigation*, vol. 98, No. 3, pp. 826-837, 1996.

Koyasu, et al., "Role of Interaction of CD2 Molecules with Lymphocyte Function-Associated Antigen 3 in T-Cel Recognition of Normal Antigen", *Proceedings of the National Academy of Science*, vol. 87, pp. 2603-2607, 1990.

Kragballe, et al., "a Double-Blind Comparison of Acitretin and Etertinate in the Treatment of Severe Psoriasis", *Acta Derm Venereol (Stockh)*, vol. 69, pp. 35-40, 1989.

Kruegar, and Duvic, "Epidemiology of Psoriasis: Clinical Issues", *The Journal of Investigative Dermatology*, vol. 102, No. 6, pp. 14S-18S, 1994.

Krueger, et al., "The Safety and Efficacy to Tazarotene Gel, a Topical Acetylenic Retinoid, in the Treament of Psoriasis", *Arch Dermatol*, vol. 134, pp. 57-60, 1998.

Kullavanijaya, and Kulthanan, "Clinical Efficacy and Side Effects of Acitretin on the Disorders of Keratinization: A One-Year Study", *The Journal of Dermatology*, vol. 20, pp. 501-506, 1993.

Kumar, et al., "Short Term Methotrexate Therapy in Psoriasis", *Indian J Med Res*, vol. 100, pp. 277-280, 1994.

Kumar, et al., "Methotrexate in Childhood Psoriasis", *Pediatric Dermatology*, vol. 11, No. 3, 271-273, 1994.

Laburte, et al., "Efficacy and Safety of Oral Cyclosporine A (CyA; Sandimmun® ) for Long-Term Treatment of Chronic Severe Plaque Psoriasis", *British Journal of Dermatology*, vol. 130, pp. 366-375, 1994.

Lai, et al., "Solid-State Chemical Stability of Proteins and Peptides", *Journal of Pharmaceutical Sciences*, vol. 88, No. 5, pp. 489-500, 1999.

Lambert, et al., "Safety and Pharmacokinetics of Hyperimmune Anti-Human Immunodeficiency Virus (HIV) Immunoglobulin Administered to HIV-Infected Pregnant Women and Their Newborns", *The Journal of Infectious Disease*, vol. 175, pp. 283-291, 1997.

Langford, et al., "Use of Cytotoxic Agents and Cyclosporine in the Treatment of Autoimmune Disease", *Annals of Internal Medicine*, vol. 129, No. 1, pp. 49-58, 1998.

Lanigan, "Treatment of Psoriasis with the Pulsed Dye Laser", *Journal of the American academy of Dermatology*, vol. 37, No. 2, pp. 288-289, 1997.

Lauharanta, and Geiger, "A Double-Blind Comparison of Acitretin and Eretinate in Combination with Bath PUVA in the Treatment of Extensive Psoriasis", *British Journal of Dermatology*, vol. 121, 107-112, 1989.

Lauharanta, et al., "A Clinical Evaluation of the Effects of an Aromatic Retinoid (Tigason), Combination of Retinoid and PUVA, and PUVA Alone in Severe Psoriasis", *British Joruna lof Dermatology*, vol. 104, pp. 325-332, 1981.

Lebwohl, et al., "Interactions Between Calcipotriene and Ultraviolet Light", *Journal of the American Academy of Dermatology*, vol. 37, No. 1, pp. 93-95, 1997.

Lebwohl, et al., "Once-Daliy Tazarotene Gel Versus Twice-Daliy Flucinonide Cream in the Treatment of Plaque Psoriasis", *Journal of the American Academy of Dermatology*, vol. 38, No. 5, pp. 705-711, 1998.

Ledo, et al., "Acitretin (Ro 10-1670) in the Treatment of Severe Psoriasis: A Randomized Double-Blind parallel Study Comparing Acitrecin and Eretinate", *International Journal of Psoriasis*, vol. 27, No. 9, pp. 656-659, 1988.

Lemster, et al., "FK 506 Inhibits Cytokine Gene and Adhesion Molecule Expression in Psoriatic Skin Lesions", *Annals of New York Academy of Sciences*, vol. 696, pp. 250-256, 1993.

Lennard-Jones, "Defining Ulcer Depth in Colitis", *The Lancet*, vol. 347, pp. 1708, 1996.

Letvin, et al., "T Lymphocyte Surface Antigens in Primates", *European Journal of Immunology*, vol. 13, pp. 345-347, 1983.

Ley, et al., "The T Cell Receptor/CD3 Complex and CD2 Stimulate the Tyrosine Phosphorylation of Indistinguishable Patterns of Polypepetides in the Human T Leukemic Cell Line Jurkat", *European Journal of Immunology*, vol. 21, pp. 2203-2209, 1991.

Lichtiger, et al., "Cyclosporine in Sever Ulcerative Colitis Refractory to Steroid Therapy", *The New England Journal of Medicine*, vol. 330, No. 26, pp. 1841-1845, 1994.

Lindelof, "Risk of Melanoma with Psoralen/Ultraviolet A Therapy for Psoriasis", *Drug Safety*, vol. 20, No. 4, pp. 289-297, 1999.

Llewellyn-Smith, et al., "Effects of Anti-CD4 Antibody Treatment on Lymphocyte Subsets and Stimulated Necrosis Factor Alpha Production: A Study of 29 Multiple Sclerosis Patients Entered into a Clinical Trial of cM-T412", *Neurology*, vol. 48, pp. 810-816, 1997.

Lorincz, "Cutaneous T-Cell Lymphoma (Mycosis Fungoides)", *The Lancet*, vol. 347, pp. 871-876, 1996.

Lotti, et al., "Neuropeptides and Skin Disorders. The New Frontiers of Neuro-Endocrine-Cutaneous Immunology", *International Journal of Dermatology*, vol. 38, pp. 673-675, 1999.

Lowe, "Initiating Neoral® Therapy", *international Journal of Dermatology*, vol. 36, pp. 30-33, 1997.

Ludden, "Population Pharmacokinetics", *Journal of Clinical Pharmacology*, vol. 28, pp. 1059-1063, 1988.

Mackay, et al., "Naïve and Memory T Cells Show Distinct Pathways of Lymphocyte Recirculation", J Exp Med. Mar. 1, 1990;171(3):801-17.

Mahrle, et al., "Anti-Inflammatory Efficacy of Low-Dose Cyclosporin A in Psoriatic Arthritis. A Prospective Multicentre Study", *British Journal of Dermatology*, vol. 135, pp. 752-757, 1996.

Majeau, et al., "Low Affinity Binding of an LFA-3/IgG1 Fusion Protein to CD2+ T Cells is Independent of Cell Activation", *Cell Adhesion and Communication*, vol. 7, No. 3, pp. 267-279, 1999.

Majewski, et al., "Papillomavirus and Autoimmunity in Psoriasis", *Immunology Today*, vol. 20, No. 10, pp. 475-476, 1999.

Matsuyama, et al., "The Quantitative and Qualitative Defect of CD4+ CD45RO+ Memory-Type T Cells are Involved in the Abnormality of TH1 Immunity in Atopic Dermatitis Patients", *Clinical and Experimental Allergy*, vol. 29, pp. 687-694, 1999.

Mazzanti, et al., "Methotrexate and Cyclosporin Combined Therapy in Severe Psoriatic Arthritis. A Pilot Study", *Acta Derm Venereol (Stockh)*, Suppl. 186, pp. 116-117, 1994.

McFarland, "Complexities in the Treatment of Autoimmune Disease", *Science*, vol. 274, pp. 2037-2038, 1996.

Meffert, and Sonnichsen, "Acitrecin in the Treatment of Severe Psoriasis: A Randomized Double-Blind study Comparing Acitrecin and Etretinate", *Acta Derm Venereol (Stockh)*, Suppl. 146, pp. 176-177, 1989.

Meffert, et al., "Low-Dose (1.25 mg/kg) Cyclosporin A: Treatment of Psoriasis and Investigation of the Influence on Lipid Profile", *Acta Derm Venereol (Stockh)*, vol. 77, pp. 137-141, 1997.

Meingassner, et al., "A Novel Anti-Inflammatory Drug, SDZ ASM 981, for the Topical and Oral Treatment of Skin Diseases: In Vivo Pharmacology", *British Journal of Dermatology*, vol. 137, pp. 568-576, 1997.

Menter, and Barker, "Psoriasis Prctice", *The Lancet*, vol. 338, pp. 231-234, 1991.

Mesalamine Study Group, "An Oral Preparation of Mesalamine as Long-Term Maintenance Therapy for Ulcerative Colitis: A Randomized Placebo-Controlled Trial", *Annals of Internal Medicine*, vol. 124, pp. 204-211, 1996.

Mordenti, "Forecasting Cephalosporin and Monobactam Antibiotic Half-Lives in Humans from Data Collected in Laboratory Animals", *Antimicrobial Agents and Chemotherapy*, vol. 27, No. 6, pp. 887-891, 1985.

Moreland, et al., "Biological Agents for Treating Rheumatoid Arthritis", *Arthritis and Rheumatism*, vol. 40, No. 3, pp. 397-409, 1997.

Morison, et al., "Consensus Workshop on the Toxic Effects of Long-Term PUVA Therapy" *Arch Dermatol*, vol. 134, pp. 595-598, 1998.

Mosmann, et al., "The Expanding Universe of T-Cell Subsets: Th1, Th2 and More", *Immunology Today*, vol. 17, No. 3, pp. 138-145, 1996.

Mrowietz, et al., "Long-Term Maintenance Therapy with Cyclosporine and Posttreatment Survey in Severe Psoriasis: Results of a Multicenter Study", *Journal of the American Academy of Dermatology*, vol. 33, No. 3, pp. 470475, 1995.

Murray, et al., "a 12-Month Treatment of Sever Psoriasis with Acitrecin: Results of a Canadian Open Multicenter Study", *Journal of the American Academy of Dermatology*, vol. 24, No. 4, pp. 598-602, 1991.

Muchenberger, et al., "The Combination of Oral Acitrecin and Bath PUVA for the Treatment of Severe Psoriasis", *British Journal of Dermatology*, vol. 137, pp. 587-589, 1997.

Mussi, et al., "Serum TNF-Alpha Levels Correlate with Disease Severity and are Reduced by Effective Therapy in Plaque-Type Psoriasis", *J Biol Regul Homeost Agents*, vol. 11, No. 3, pp. 115-118, 1997.

Nair, et al., "Evidence for Two Psoriasis Susceptibility Loci (HLA and 17q) and Two Novel Candidate Regions (16q and 20p) by Genome-Wide Scan", *Human Molecular Genetics*, vol. 6, No. 8, pp. 1349-1356, 1997.

Naldi, et al., "Analytical Epidemiology in Psoriasis", *Journal of Investigative Dermatology*, vol. 102, No. 6, pp. 19S-23S, 1994.

Nickoloff, et al., "Cytokine Networks: Immunobiology Surfaces", *The Journal of NIH Research*, vol. 3, pp. 71-74, 1991.

Nickoloff, "The Cytokine Network in Psoriasis", *Arch Dermatol*, vol. 127, pp. 871-884, 1991.

Nickoloff, et al., "Acessory Cell Function of Keratinocytes for Superantigens: Dependence of Lymphocyte Function-Associated Antigen-1/Intercellular Adhesion Molecule-1 Interaction", *The Journal of Immunology*, vol. 150, No. 6, pp. 2148-2159, 1993.

Nishibu, et al., "Overexpression of Monocyte-Derived Cytokines in Active Psoriasis: A Relation to Coexistent Arthropathy", *Journal of Dermatological Science*, vol. 21, pp. 63-70, 1999.

Olivieri, et al., "Therapy with Cyclosporine in Psoriatic Arthritis", *Seminars in Arthritis and Rheumatism*, vol. 27, No. 1, pp. 36-43, 1997.

Park, and Youn, "Factors Influencing Psoriasis: An Analysis Based upon the Extent of Involvement and Clinical Type", *The Journal of Dermatology*, vol. 25, pp. 97-102, 1998.

Patel, et al., "Compatibility of Calcipotriene with Other Topical Medications", *Journal of the American Academy of Dermatology*, vol. 38 No. 6, pp. 1010-1011, 1998.

Pavli, et al., "Inflammatory Bowel Disease: Germs or Genes?", *The Lancet*, vol. 347, pp. 1198, 1996.

Pearson, et al., "Azathioprine and 6-Mercaptopurine in Crohn Disease: A Meta-Analysis", *Annals of Internal Medicine*, vol. 122, pp. 132-142, 1995.

Peckham, et al., "The Treatment of Severe Psoriasis", *Arch Dermatol*, vol. 123, pp. 1303-1307, 1987.

Peterson, "Genetic Analysis of CD2/LFA-3 and CD4/HIV Interactions", Ph.D. dissertation, Harvard University, Jul. 1988.

Pettit, "Oral Retinoid for Psoriasis: A Report of a Double Blind Study", Acta Derm Venereol Suppl (Stockh). 1979;59(85):133-6.

Petzelbauer, et al., "Cyclosporin A Suppresses ICAM-1 Expression by Papillary Endothelium in Healing Psoriatic Plaques", *The Journal of Investigative Dermatology*, vol. 96, No. 3, pp. 362-386, 1991.

Pitzalis, et al., "Selective Migration of the Human Helper-Inducer Memory T Cell Subset: Confirmation by In Vivo Cellular Studies", *European Journal of Immunology*, vol. 21, pp. 369-376, 1991.

Podolsky, "Inflammatory Bowel Disease", *The New England Journal of Medicine*, vol. 325, No. 13, pp. 928-1014, 1991.

Poikolainen, et al., "Excess Mortality Related to Alcohol and Smoking Among Hospital-Treated Patients with Psoriasis", *Arch Dermatol*, vol. 135, pp. 1490-1493, 1999.

Polito, et al., "Preliminary Evidence for Genetic Anticipation in Crohn's Disease", *The Lancet*, vol. 347, pp. 798-800, 1996.

Prens, et al., "T Lymphocytes in Psoriasis", *Clinics in Dermatology*, vol. 13, pp. 115-129, 1995.

Prinz, "Which T Cells Cause Psoriasis?", *Clinical and Experimental Dermatology*, vol. 24, pp. 291-295, 1999.

Rao, et al., "C-Terminal Modification Occurs in Tissue Culture Produced OKT3", Biopharm-The Technology & Business of Biopharmaceuticals, 1991, v. 4, N. 10, p. 38-43.

Refsum, et al., "Fasting Plasma Homocysteine as a Sensitive Parameter of Antifolate Effect: A Study of Psoriasis Patients Receiving Low-Dose Methotrexate Treatment", Clinical Pharmacology Therapy, vol. 46, No. 5, pp. 510-520, 1989.

Reilly, et al., "Problems of Delivery of Monoclonal Antibodies: Pharmaceutical and Pharmacokinetic Solutions", Clinical Pharmacokenetics, vol. 28, No. 2, pp. 126-142, 1995.

Reilly, et al., "Compartmental Analysis of the Pharmacokinetics of Radioiodinated Monoclonal Antibody B72.3 in Colon Cancer Patients", Nucl. Med. Biol, vol. 20, No. 1, pp. 57-64, 1993.

Rivers, et al., "UVA Sunbeds: Tanning, Photoprotection, Acute Adverse Effects and Immunological Changes", British Journal of Dermatology, vol. 120, pp. 767-777, 1989.

Rodriguez, et al., "Optic Neuritis Posed a 40-Year Risk of 60% for Multiple Sclerosis", ACP Journal Club, vol. 122-123: 21, 1995.

Salmi, et al., "Dual Binding Capacity of Mucosal Immunoblasts to Mucosal and Synovial Endothelium in Humans: Dissection of the Molecular Mechanisms", Journal of Experimental Medicine, vol. 181, pp. 137-149, 1995.

Salmi, et al., "Homing of Mucosal Leukocytes to Joints: Distinct Endothelial Ligands in Synovium Mediate Leukocyte-Subtype Specific Adhesion", Journal of Clinical Investigation, vol. 99, No. 9, pp. 2165-2172, 1997.

Sander, et al., "The Annual Cost of Psoriasis", Journal of the American Academy of Dermatology, vol. 28, No. 3, pp. 422-425, 1993.

Sanders, et al., "Human Memory T Lymphocytes Express Increased Levels of Three Cell Adhesion Molecules (LFA-3, CD2, and LFA-1) and Three Other Molecules (UCHL1, CDw29, and Pgp-1) and have enhanced IFN-γ Production", The Journal of Immunology, vol. 140, No. 5, pp. 1401-1407, 1988.

Schraven, et al., "Alterations of CD2 Association with T Cell Receptor Signaling Molecules in 'CD2 Unresponsive' Human T Lymphocytes", European Journal of Immunology, vol. 23, pp. 119-123, 1993.

Schwartz, et al., "Identification of the TS2/18-Recognized Epitope on the CD2 Molecule as a Target for Suppression of T Cell Cytokine Synthesis", The Journal of Immunology, vol. 154, pp. 5813-5820, 1995.

Seed, "An LFA-3 cDNA Encodes a Phospholipid-Linked Membrane Protein Homologous to its Receptor CD2", Nature, vol. 329, pp. 840-842, 1987.

Seo, "Evaluation of Disease Activity in Patients with Moderately Active Ulcerative Colitis: Comparisions Between a New Activity Index and Truelove and Witts' Classification", The American Journal of Gastroenterology, vol. 90, No. 10, pp. 1759-1763, 1995.

Shahidullah, et al., "Etretinate Therapy for Psoriasis and Other Keratinizing Disorders: A 10-Year Retrospective Study in Singapore", International Journal of Dermatology, vol. 32, No. 9, pp. 686-689, 1993.

Shanahan, "Pathogenesis of Ulcerative Colitis", The Lancet, vol. 342, pp. 407-411, 1993.

Shaw, et al., "Cyclosporin A and Vitamin D Metabolism: Studies in Patients with Psoriasis and in rats", Clinical Science, vol. 86, pp. 627-632, 1994.

Shupack, "Maintenance Therapy with Neoral® ", International Journal of Dermatology, vol. 36, pp. 34-36, 1997.

Singh, et al., "Acute Immobilization Stress Triggers Skin Last Cell Degranulation via Corticotropin Releasing Hormone, Neurotensin, and Substance P: A Link to Neurogenic Skin Disorders", Brain Behavior, and Immunity, vol. 13, pp. 225-239, 1999.

Smith, and Barker, "Cell Trafficking and Role of Adhesion Molecules in Psoriasis", Clinics in Dermatology, vol. 13, pp. 151-160, 1995.

Somerville, and Scott, "Neoral-New Cyclosporin For Old?", British Journal of Rheumatology, vol. 36, pp. 1113-1115, 1997.

Spuls, et al., "A Systematic Review of Five Systematice Treatments for Severe Psoriasis", British Journal of Dermatology, vol. 137, pp. 943-949, 1997.

Storkus, and Dawson, "A Target Structures Involved in Natural Killing (NK): Characteristics, Distribution, and Candidate Molecules", Immunology, vol. 10, No. 5, 393-416, 1991.

Stern, "Utilization of Outpatient Care for Psoriasis", The Journal of the American Academy of Dermatology, vol. 35, No. 4, pp. 543-549, 1996.

Stern, "Narrowband UV-B and Psoriasis", Arch Dermatol, vol. 133, pp. 1587-1588, 1997.

Stern, "Psoriasis", The Lancet, vol. 350, pp. 349-353, 1997.

Stern, et al., "Malignant Melanoma in Patients Treated for Psoriasis with Methoxsalen (Psoralen) and ultraviolet A Radiation (PUVA)", The New England Journal of Medicine, vol. 336, No. 15, pp. 1041-1045, 1997.

Stern, et al., "The Safety of Etretinate as Long-Term Therapy for Psoriasis: Results of the Etretinate Follow-Up Study", Journal of the American Academy of Dermatology, vol. 33, No. 1, pp. 44-52, 1995.

Sultan, et al., "Blockade of CD2-LFA-3 Interactions Protects Human Skin Allografts in Immunodeficient Mouse/Human Chimeras", Nature Biotechnology, vol. 15, pp. 759-762, 1997.

Sutherland, et al., "Standards for Trials of Therapy in Inflammatory Bowel Disease", Inflammatory Bowel Diseases, vol. 3, No. 4, pp. 277-283, 1997.

Talwat, et al., "Sequential Clinico-Histological Studies in Psoriasis Following Methotrexate Therapy", Ind J Dermatol Venereol Leprol, vol. 61, pp. 284-287, 1995.

Task Force of the Working Group on Arrhythmias of the European Society of Cardiology, "The Early Termination of Clinical Trials: Causes, Consequences, and Control", European Heart Journal, vol. 15, pp. 721-738, 1994.

Thomas, et al., "Transdermal Nicotine as Maintenance Therapy for Ulcerative Colitis", The New England Journal of Medicine, vol. 332, No. 15, pp. 988-992, 1995.

Traupe, "The Puzzling Genetics of Psoriasis", Clinics in Dermatology, vol. 13, pp. 99-103, 1995.

Trembath, et al., "Identification of a Major Susceptibility Locus on Chromosome 6p and Evidence for Further Disease Loci Revealed by a Two Stage Genome-Wide Search in Psoriasis", Human Molecular Genetics, vol. 6, No. 5, pp. 813-820, 1997.

Urlaub, and Chasin, "Isolation of Chinese Hamster Cell Mutants Deficient in Dihydrofolate Reductase Activity", Proc Natl Acad Sci, vol. 77, No. 7, pp. 4216-4220, 1980.

Urlaub, et al., "Effect of Gamma Rays at the Dihydrofolate Reductase Locus: Deletions and Inversions", Somatic Cell and Molecular Genetics, vol. 12, No. 6, pp. 555-566, 1986.

Valdimarsson, et al., "Psoriasis: A T-Cell-Mediated Autoimmune Disease Induced by Streptococcal Superantigens?", Immunology Today, vol. 16, No. 3, pp. 145-149, 1995.

Van de Kerkhof, "An Update on Vitamin D3 Analogues in the Treatment of Psoriasis", Skin Pharmacology and Applied Skin Physiology, vol. 11, pp. 2-10, 1998.

Van de Kerkhof, "The Psoriasis Area and Severity Index and Alternative Approaches for the Assessment of Severity: Persisting Areas of Confusion", British Journal of Dermatology, vol. 137, pp. 661-662, 1997.

Van de Kerkhof, "Reduction of Epidermal Abnormalities and Inflammatory Changes in Psoriatic Plaques During Treatment with Vitamin D3 Analogs", Journal of Investigative Dermatology Symposium Proceedings, vol. 1, pp. 78-81, 1996.

Van de Kerkhof, "Review: The Management of Psoriasis", Netherlands Journal of Medicine, vol. 52, pp. 40-45, 1998.

Van de Kerkhof, et al., "TheEffect of Addition of Calcipotriol Ointment (50 μg/g) to Acitretin Therapy in Psoriasis", British Journal of Dermatology, vol. 138, pp. 84-89, 1998.

Van de Kerkhof, et al., "Evaluation of Topical Drug Treatment in Psoriasis", Dermatology, vol. 197, pp. 31-36, 1998.

Van der Merwe, et al., "Human Cell-Adhesion Molecule CD2 Binds CD58 (LFA-3) with a Very Low Affinity and an Extremely Fast Dissociation Rate but does not Bind CD48 or CD59", Biochemistry, vol. 33, pp. 10149-10160, 1994.

Van der Rhee, et al., "Combined Treatment of Psoriasis with a New Aromatic Retinoid (Tigason) in Low Dosage Orally and Triamcinolone Acetonide Cream Topically: A Double-Blind Trial", *British Journal of Dermatology*, vol. 102, pp. 203-211, 1980.

Van Kooyk, et al., "Enhancement of LFA-1-Mediated Cell Adhesion by Triggering through CD2 or CD3 on T Lymphocytes", *Nature*, vol. 342, pp. 811-813, 1989.

Van Onselen, "Psoriasis in General Practice", *Nursing Standard*, vol. 12, No. 30, pp. 32-33, 1998.

Verstuyf, et al., "Recent Developments in the Use of Vitamin D Analogues", *Expert Opin Investig Drugs*, vol. 9, No. 3, pp. 397-403, 1998.

Wahl, "The Impact of Psoriasis on Psychosocial Life Domains: A Review", *Scandinavian Journal of Caring Science*, vol. 11, pp. 243-249, 1997.

Wahl, et al., "Sulfasalazine: A Potent and Specific Inhibitor of Nuclear Factor Kappa B", *Journal of clinical Investigation*, vol. 101, No. 5, pp. 1163-1174, 1998.

Wang, et al., "Structure of a Heterophilic Adhesion Complex between the Human CD2 and CD58 (LFA-3) Counterreceptors", *Cell*, vol. 97, pp. 971-803, 1999.

Wanquing, et al., "Clinical Study of Cyclosporin A for Psoriasis in China", *Annals of Dermatology*, vol. 7, No. 4, pp. 313-317, 1995.

Weinblatt, et al., "Methotrexate for Chronic Diseases in Adults", *The New England Journal of Medicine*, vol. 332, No. 5, pp. 330-331, 1995.

Weiner, et al., "Phase I Evaluation of an Anti-Breast Carcinoma Monoclonal Antibody 260F9-Recombinant Ricin A Chain Immunoconjugate", *Cancer Research*, vol. 49, pp. 4062-4067, 1989.

Weinstein, "Psoriasis Therapy After Remission: The Next Step", *International Journal of Dermatology*, vol. 36, pp. 37-40, 1997.

Weinstein, "Tazarotene Gel: Efficacy and Safety in Plaque Psoriasis", *Journal of the American Academy of Dermatology*, vol. 37, No. 2, pp. S33-S38, 1997.

Weinstein, et al., "Tazarotene Gel, a New Retinoid, for Topical Therapy of Psoriasis: Vehicle-Controlled Study of Safety, Efficacy, and Duration of Therapeutic Effect", *Journal of the American Academy of Dermatology*, vol. 37, No. 1, pp. 85-92, 1997.

Weiss, and Ashwell, "The Asialoglycoprotein Receptor: Properties and Modulation by Ligand", Baumann, P., et al., (ED.). Progress in Clinical and Biological Research, vol. 300.

Whitmore, and Morison, "Melanoma after PUVA Therapy for Psoriasis", *The New England Journal of Medicine*, vol. 337, No. 7, pp. 502, 1997.

Willkens, et al., "Randomized, Double-Blind, Placebo Controlled Trial of Low-Dose Pulse Methotrexate in Psoriatic Arthritis", *Arthritis and Rheumatism*, vol. 27, No. 4, pp. 376-381, 1984.

Wolska, et al., "Etretinate in Severe Psoriasis: Results of Double-Blind Study and Maintenance Therapy in Pustular Psoriasis", *Journal of the American Academy of Dermatology*, vol. 9, No. 6, pp. 883-887, 1983.

Wright, et al., "Human Low-Dosage Parenteral Methotrexate Therapy: A Controlled Toxicity Study", *Arch Derm*, vol. 93, pp. 731-736, 1966.

Yocum, et al., "Clinical and immunological effects of a Primatized Anti-CD4 Monoclonal Antibody in Active Rheumatoid Arthritis: Results of a Phase I, Single Dose, Dose Escalating Trial", *Journal of Rheumatology*, vol. 25, pp. 1257-1262, 1998.

Young, et al., "A Persepctive study of Renal Structure and Function in Psoriasis Patients with Cyclosporin", *Kidney International*, vol. 46, pp. 1216-1222, 1994.

Zachariae, "Alcohol Interactions with Drugs and its Effects on the Treatment of Skin Diseases", *Clinics in Dermatology*, vol. 17, pp. 443-445, 1999.

Abraham et al. (1990) "Interactions between lymphocutes and dermal fibroblasts: An in vitro model of cutaneous lymphocyte trafficking," Experimental Cell Research 190, 118-126.

Alberts et al., Molecular Biology of the Cell, 1994, Garland Publishing, Inc., New York, NY, pp. 1243, 1994.

Ameen, "Genetic basis of *Psoriasis vulgaris* and its pharmacogenetic potential", Pharmacogenomics 4(3); 297-308 (2003).

Athos, et al., "Identification of the Residues in Human CD4 Critical for the Binding of HIV", Cell, 57(3):469-481 (1989).

ATCC Cell Lines and Hybridomas 8th Edition 1994 p. 420 only.

Barthels et al., "Isolation and Nucleotide Sequence of Mouse NCAM cDNA that Codes for a M.sub.r 79000 Polypeptide Without a Membrane-Spanning Region," EMBO Journal, 6 (4), pp. 907-914 (1987).

Benjamin, et al., "MAb to cell interaction antigens block human T-dependent B cell activation", J. Cell. Biochem. Keystone Symposia on Molecular & Cellular Biology Supp. 17B: 172 (1993).

Benton et al., "Screening the Recombinant Clones by Hybridization to Single Plaques in situ", Science, 196, 180-182 (1977).

Bieber et al. (1981) "Complications in long-term survivors of cardiac transplantation", Transplant Proc. 8(1): 207-211.

Bierer, B. et al. "Synergistic T cell activation via the physiological ligands for CD2 and the T cell receptor", J. Exp. Med. 168: 1145-1156, Sep. 1988.

Bonnerjea, et al. "Protein Purification: The Right Step at the Right Time" Bio/Technology 4:955 (1986).

Bovenschen, et al., "Explorative immunohistochemical study to evaluate the addition of a topical corticosteroid in the early phase of alefacept treatment for psoriasis", Arch. Dermatol. Res. 298: 457-463 (2007).

Bowie et al. Deciphering the messages in protein sequences: Tolerance to amini acid sustitutions. Science 240: 1306-1310; Mar. 1990.

Bressler, P., et al., "Anti-CD2 Receptor Antibodies Activate the HIV Long Terminal Repeat in T Lymphocytes", J. Immunol., 147(7), pp. 2290-2294 (Oct. 1, 1991).

Brod, S. A. et al., "T-T Cell Interactions Are Mediated by Adhesion Molecules," Eur. J. Immunol., 20, pp. 2259-2268 (1990).

Carrera, et al. "Triggering of co-mitogenic signals in T cell proliferations by anti-LFA-1 (CD18, CD11a), CLA-3, and CD7 monoclonal antibodies", J. Immunol. 141(6):1919-1924 (1988).

Cate, et al., "Isolation of the Bovine and Human Genes for Mullerian Inhibiting Substance and Expression of the Human 'Gene in Animal Cells", Cell, 45, 685-698 (1986).

Cerdan, et al., "Prolonged IL-2 receptor a/CD25 expression after T cell activation via the adhesion molecules CD2 and CD28", J. Immunol. 149(7):2255-2261 (1992).

Chavin, et al., "Prolongation of allograft and xenograft survival in mice by anti-CD2 monoclonal antibodies", Transplantation, 54(2):286-291 (1992).

Church, et al., "Genomic Sequencing", Proc. Natl. Acad. Sci. U.S.A., 81, 1991-1995 (1984).

Colvin, et al., "Cellular and Molecular Mechanisms of Allograft Rejection", Ann Rev Med 41:361-375 (1990).

Conzelmann et al. (1986) "Anchoring of membrane proteins via phosphatidylinositol is deficient in two classes of Thy-1 negative mutant lymphoma cell", The EMBO J., vol. 5, No. 12, pp. 3291-3296.

Cosimi et al.; "In Vivo Effects of Monoclonal Antibody to ICAM-1 (CD54) in Nonhuman Primates with Renal Allografts.sup.1" (The Journal of Immunology—Jun. 15, 1990 pp. 4604-4612).

Cosimi et al.; "Prolonged survival of nonhuman primate renal allograft recipients treated only with anti-CD4 monoclonal antibody" Surgery, 108 (2): 1990 pp. 406-414).

Cosimi, et al. "Immunosuppression of Cynomolgus Recipients of Renal Allografts . . . " Leukocyte Adhesion Molecules (Springer-Verlog 1988) pp. 275-281.

Cosimi, et al., "Anti-T-Cell Monoclonal Antibodies in Transplantation Therapy", Transplantation Proc. 15(3):1889-1892 (1983).

Cuelar, et al., "Psoriatic Arthritis Current Developments" J. Florida M.A. 82(5):338-342 (1995).

Cunningham et al., "Neural Cell Adhesion Molecule: Structure, Immunoglobulin-Like Domains, Cell Surface Modulation, and Alternative RNA Splicing," Science, 236, pp. 799-806 (1987).

Dailey, et al., "Sequences in the Polyomavirus DNA Regulatory Region Involved in Viral DNA Replication and Early Gene Expression," J. Virology, 54 (3), pp. 739-749 (Jun. 1985).

Damle, et al., "Costimulation of T lymphocytes with integrin ligands inttercellular adhesion molecule 1 or vascular cell adhesion molecule 1 induces functional expression of CTLA-4, a second receptor for B7" J. Immunol (1994).

Damle, et al., "Stimulation of cloned human T lymphocytes via the CD3 or CD28 molecules induces enhancement in vascular endothelial permability to macromolecules with participation to type -1 and type-2 intercellular adhesion pathways" Eur. J. Immunol. 20 (9):1995-2003 (1990).

Damle, N., et al., "Differential Costimulatory Effects of Adhesion Molecules B7, ICAM-1, LFA-3, and VCAM-1 on Resting and Antigen-Primed CD4.sup.+T Lymphocytes" The Journal of Immunology, vol. 148, 1985-1992, No. 7 (Apr. 1, 1992).

Deckert, et al., "CD59 molecule: A second ligand for CD2 in T cell adhesion", Eur. J. Immunol. 22:2943-2947 (1992).

Dente, L., et al., "pEMBL: a New Family of Single Stranded Plasmids," Nucleic Acids Research, 11(6), pp. 1645-1655 (1983).

Ellis, "Quality of Life Results from a Randomized Double Blind Multi Center Dose Response study of LFA3TIP in patients with Chronic Plaque Psoriasis" Am Acad Dermatol. 58th Ann Meeting Mar. 10-15, 2000. (Abstract).

Enea, V. and N. D. Zinder, "Interference Resistant Mutants of Phage f1," Virology, 122, pp. 222-226 (1982).

Ezekowitz, et al., "The Interferons: Basic Biology and Therapeutic Potential" in Therapeutic Immnology, edited by Austen et al., (Blackwell Science, Cambridge, MA, 1996) 249-263.

Ferguson et al. (1988) "Cell-surface anchoring of proteins via glycosyl-phosphatidylinositol structures", Ann. Rev. Biochem., vol. 57, pp. 285-320.

Feracilli, et al., "Effects of cyclosporine on joint damage in rheumatoid arthritis", clin Exp. Rheum. 15 (Supp 17):S83-S89 (1997).

Findlay "Purification of Membrane Proteins" Ch. 4 in Protein Purification Applications, A Practical Approach (Harris and Angel, eds) 1990 (cited for argument).

First, "Transplantation in the Nineties", Transplantation 53(1): 1-11 (1992).

Fishel, et al. "The cellular response to xenotransplantation", curr. Surg. 47(5):345-347 (1990).

Fischer, "T cell adhesion", J. Exp. Clin. Hematol. 32:49-51 (1990).

Gamache et al. (1996) "Pharmacokinetics of LFA3TIP, an immunoglobulin fusion protein, in male and female baboons", Pharmaceutical Research 13 (9 Sup.); s399 (Abstract).

Geider, K., et al., "A Plasmid Cloning System Utilizing Replication and Packaging Functions of the Filamentous Bacteriophage fd," Gene, 33, pp. 340-349 (1985).

Genmab Press release 48/2002 "HuMAX CD-4 in combination therapy not effective in Rheumatoid Arthritis".

Gimenez-Arnau, et al., "Psoriasis: bases de actuacion terapeutica", Act. Dermatolog. 3:159-171(1998).

Giorgi, et al, "Immunosuppressive Effect and Immunogenicity of OKT11A monoclonal antibody in monkey allograft recipients", Transplantation Proc. 15(1):639-642 (1983).

Goedkoop et al., "Alefacept therapy reduces the efector T-cell population in lesional psoriatic epidermis", Arch. Dermatol. Res. 295:465-473 (2004).

Gordon, et al. "Treatment of psoriasis with alefacept", Arch. Dermatol. 139: 1563-1570 (2003).

Grosveld, et al., "The Construction of Cosmid Libraries Which Can Be Used to Transform Eukaryotic Cells", Nucl. Acids. Res., 10(21), 6715-6732 (1982).

Gubler, et al., "A Simple and Very Efficient Method for Generating cDNA Libraries", Gene, 25, 263-269 (1983).

Hafler, et al., "Anti-CD4 and anti-CD2 monoclonal antibody infusions in subjects with multiple sclerosis", J. Immunol. 141(1): 131-138 (1988).

Hale, et al. "Bromelain treatment of human T cells removes CD44, CD45RA, E2/MIC2, CD6, CD7, CD8, and Leu 8/LAM1 surface molecules and markedly enhances CD2-mediated T cell activation", J. Immunol. 149(12):3809-3816 (1992).

Hawkes, et al., "a Dot-Immnobinding Assay for Monoclonal and Other Antibodies", Anal. Biochem,., 119, 142-147 (1982).

He et al., "Phosphatidylinositol is Involved in the Membrane Attachment of NCAM-120, the Smallest Component of the Neural Cell Adhesion Molecule", EMBO Journal, 5, (10), pp. 2489-2494 (1986).

Hebel, et al., "Suppression of the immune response by a soluble complement receptor of B lymphocytes", Science 254(5028):102-105 (1991) (cited for argument).

Heij (La Hej), et al., "Adhesion molecules in iris biopsy specimens from patients with uveitis", Br. J. Opthamol. 82(4): 432-437 (1998).

Hewick, et al., "A Gas-Liquid Solid Phase Peptide and Protein Sequentor", J. Biol. Chem., 256(15), 7990-7997 (1981).

Hoffmann, et al., "Initiation and perpetuation of rat adjuvant arthritis is inhibited by the anti-CD2 monoclonal antibody (mAb) OX34", Annals of Rheumatic Diseases, 56 (12) : 716-722 (1997).

Hollsberg, et al., "Increased protein kinase C activity in human memory T cells", Cell. Immunol. 149(1):170-179 (1993).

Hooks et al., "Muromonab CD-3: A review of its pharmacology, pharmacokinetics, and clinical use in transplantation", Pharmacotherpy 11(1):25-37 (1991).

Hyman (1985) "Cell-surface-antigen mutants of haematopoietic cells", Biochem J., vol. 225, pp. 27-40.

Inoue, et al., "Anti-adhesion molecule therapy in Theiler's murine encephalomyelitis virus-induced demyelinating disease", Int. Immunol. 9(12): 1837-1847 (1997).

International Searching Authority, International Search Report for International Application No. PCT/US88/01924, dated Oct. 7, 1988.

International Searching Authority, International Search Report for International Application No. PCT/US89/03652, dated Feb. 7, 1990.

International Searching Authority, International Search Report for International Application No. PCT/US92/02050, dated Aug. 12, 1992.

International Searching Authority, International Search Report for International Application No. PCT/US92/08754, dated Jun. 28, 1993.

International Searching Authority, International Search Report for International Application No. PCT/US92/08755, dated Jul. 8, 1993.

International Searching Authority, International Search Report for International Application No. PCT/US99/20026, dated May 8, 2000.

International Searching Authority, International Search Report for International Application No. PCT/US02/02314, dated Jun. 11, 2002.

International Searching Authority, International Search Report for International Application No. PCT/US02/21631, dated Jun. 25, 2003.

International Searching Authority, International Search Report for International Application No. PCT/US05/16265, dated Oct. 26, 2005.

International Searching Authority, International Search Report for International Application No. PCT/US05/15531, dated Feb. 24, 2006.

International Searching Authority, International Search Report for International Application No. PCT/US05/03907, dated Oct. 3, 2005.

International Searching Authority, International Search Report for International Application No. PCT/US05/39070, dated Apr. 27, 2007.

Ip,et al., Structural Characterization of the N-Glycans of a Humanized Anti-CD 18 Murine Immunoglobulin G, Archives of Biochemistry and Biophysics, vol. 308, No. 2, pp. 387-399, 1994.

Jonker, "Immunosuppressive Therapy by monoclonal anti-T lymphocyte subset antibodies", Leukocyte Typing III (Oxford Univ. Press 1987) pp. 923-927.

Jonker, et al., "The Influence of OKT8F Treatment on Allograft Survival in Rhesus Monkeys", Transplantation 41(4): 431-435 (1986).

Jonker, et al., "Effects of in vivo administration of monoclonal antibodies specific for human T cell subpopulations on the immune system in a rhesus monkey model", Transplantation 35(6): 521-526 (1983).

Kaplon et al. (1996) "Short course single agent therapy with an LFA-3-lgG.sub.I fusion protein prolongs primate cardiac allograft survival." Transplantation 61(3): 356-363.

Kasahara, et al., "Role of interleukin 6 for differential responsiveness of naive and memory CD4+ T cells in CD2-mediated activation", J. Exp. Med. 172 (5): 1419-1424 (1990).

Kawai, et al., "Intrathecal administration of antibodies against LFA-1 and against ICAM-1 suppresses experimental allergic encephalomyelitis in rats", Cell Immunol. 171(2):262-268 (1996).
Kent, S. B. H., "Chemical Synthesis of Peptides and Proteins," Ann. Rev. Biochem., 57, pp. 957-989 (1988).
Kimball ,Introduction to Immunology, 1983, (Ed.), Macmillan Publishing Co., New York, NY, 1983.
Kirkham, et al., "Chimeric CD7 monoclonal antibody therapy in Rheumatoid arthritis", J. Rheumatol. 19(9) 1348-1352 (1992).
Knox, et al., "Observations on the effect of chimeric anti-CD4 monoclonal antibody in patients with mycosis fungoides", Blood 77(1):20-30 (1991).
Kohler, G. and C. Milstein, "Continuous Cultures of Fused Cells Secreting Antibody of Predefined Specificity," Nature, 256, pp. 495-497 (Aug. 7, 1975).
Kraan et al., "Alefacept Treatment in Psoriatic Arthritis" Arthritis Rheum. 46(10):2776-2784 (2002).
Kranz et al., "Immunoprecipitation of Cell Surface Structures of Cloned Cytotoxic T Lymphocytes by Clone-Specific Antisera," Proc. Natl. Acad. Sci. U.S.A., vol. 81, pp. 573-77 (1984).
Krueger, et al., "Anti-CD11a treatment for psoriasis concurrently increases circulating T-cells and decreases plaque T-cells, consistent with inhibition of cutaneous T-cell trafficking", J. Inves. Derm. 115:333 (2000) (Abstract).
Krueger "Efficacy and Safety results of a phase II trial with LFA3TIP in patients with chronic plaque psoriasis." Am Acad Dermatol. 58th Ann Meeting Mar. 10-15, 2000. (Abstract).
Krueger, Efficacy and Safety results of a phase II trial with LFA3TIP in patients with chronic plaque psoriasis. From Gene to Clinic Congress. AMEVIVE™ Breakfast Meeting Dec. 3, 1999 p. 1.
Kupper, "Immune and inflammatory processes in cutaneous tissues: mechanisms and speculations", J. Clin. Invest. 86:1783-1789 (1990).
Lai et al., "Two Forms of TB236/Myelin-Associated Glyco Protein, a Cell Adhesion Molecule for Postnatal Neural Development, are Produced by Alternative Splicing," Proc. Natl. Acad. Sci. U.S.A., 84, pp. 4337-4441 (1987).
Lambert, J. M. et al., "Purified Immunotoxins That Are Reactive With Human Lymphoid Cells," J. Biol. Chem., 260(22), pp. 12035-12041 (1985).
Li, et al., "Enhancement of B cell responses by the interaction of CD2 with LFA-3", J. Tongji Med. Univ. 12(2):71-74 (1992).
Liao, T., et al., "Modification of Sialyl Residues of Sialoglycoprotein(s) of the Human Erythrocyte Surface," J. Biol. Chem., 248(23), pp. 8247-8253 (Dec. 10, 1973).
Low, "Biochemistry of the Glycosyl-Phosphatidylinositol Membrane Protein Anchors," Biochem. J., 244, pp. 1-13 (1987).
Magilavy, et al., "Targeting CD2 for immunotherapy: results of a phase 1 trial with a LFA-3/IgG Fe fusion protein", Arthritis Rheum. 40(9-suppl.): S176 (1997) (Abstract).
Magilavy, et al., "Pharmacodynamic effects of LFA3TIP (Amevive) in patients with chronic palque psoriasis (CPP) : Selective modulation of CD45RO+lymphocytes", J. Invest. Dermatol 112(4):609 (1999) (Abstract).
Makgoba et al., "Human T Cell Rosetting is Mediated by LFA-3 on Autologous Erythrocytes," Journ. Immunol., vol. 138(11), pp. 3587-3589 (1987).
Maniatis, et al., "Extraction, Purification, and Analysis of mRNA from Eukaryotic Cells", Molecular Cloning, A Laboratory Manual187-209 (Cold Spring Harbor Laboratory, 1982).
March, et al., "A Simplified Method for Cyanogen Bromide Activation of Agarose for Affinity Chromatography", Anal. Biochem., 60, 149-152 (1974).
Maxam et al., "Sequencing End-Labeled DNA with Base-Specific Chemical Cleavages", Methods in Enzymology, 65:499-560 (Academic Press, 1980).
Maxam, et al., "A New Method for Sequencing DNA", Proc. Natl. Acad. Sci., 74, 560-564 (1977).
Meier et al (1995) "Immunomodulation by LFA3TIP, an LFA-3/IgG.sub.I fusion protein: cell line dependent glycosylation effects on pharmacokinetics and pharmacodynamic markers," Therapeutic Immunology 2(2): 159-171.

Merck Manual, Seventeenth Ed. pp. 303-313, 448, 725-729, 1474-1476.
Michler, et al. "Pretransplant blood transfusion in a primate cardiac xenograft model", Curr. Surg. 44(1):42-45 (1987).
Michler, et al., "Technique for primate heterotopic cardiac xenotransplantation", J. Med. Primatol. 14:357-362 (1985).
Michler, et al., "Prolongation of primate cardiac xenograft survival with cyclosporine", Transplantation 44(5):632-636 (1987).
Mikayama, et al., "Molecular cloning and functional expression of a cDNA encoding glycosylation-inhibiting factor", PNAS 90:10056-10060 (1993).
Moreland, et al. "Use of a chimeric monoclonal anti-Cd4 antibody in patients with refractory rheumatoid arthritis", Arthritis and Rheumatism 36(3) (1993).
Moroney, S. E., et al., "Modification of the Binding Site(s) of Lectins by an Affinity Column Carrying an Activated Galactose-Terminated Ligand," Biochemistry, 26, pp. 8390-8398 (1987).
Morrison, S. L., "Transfectomas Provide Novel Chimeric Antibodies," Science, 229, pp. 1202-1207 (Sep. 20, 1985).
Mulligan et al., "Selection for Animal Cells that Express the Escherichia Coli Gene Coding for Xanthine-Guanine Phophoribosyltransferase", Proc. Natl. Acad. Sci. U.S.A., 78:2072-2076 (1981).
Nakakura, et al., "Potent and effective prolongation by anti-LFA-1 monoclonal antibody monotherapy of non-primarily vascularized heart allograft survival in mice without T cell depletion", Transplantation 5592):412-417 (1993).
Ngo et al. "Computational complexity, protein structure prediction, and the Levinthal paradox" in The Protein Folding Problem and Tertiary Structure Prediction, 1994, Merz et al. (Ed.) Birkhauser, Boston, MA, pp. 433 and 492-495, 1994.
Nicolas, et al., "CD4 antibody treatment of severe psoriasis", Lancet 338:321 (1991).
O'Gorman, et al., "Genetic Polymorphisms associated with clinical improvement of chronic plaque psoriasis after treatment with alefacept", J. Inves. Derm. 124(4): A40 (2005) (Abstract).
Okayama, et al., "High-Efficiency Cloning of Full-Length cDNA", Mol. Cell. Biol., 2(2):161-170 (1982).
Peng, et al., "Ligation of CD2 provides a strong helper signal for the production of the type 2 cytokines", Cell. Immunol., 181(1):76-85 (1997).
Pepinsky, et al., "Purification and Partial Sequence Analysis of a 37-kDA Protein that Inhibits Phospholipase A.sub.2 Activity from Rat Peritoneal Exudates", J. Bio. Chem., 261(9), 4239-4246 (1986).
Pitzalis, "Skin and joint disease in psoriatic arthritis: What is the link?" Br. J. Rheum. 37(5): 480-483 (1998).
Platt, et al. "Transplantation of discordant xenografts: a review of progress", Immunol. Today 11(12):450-456 (1990).
Prentice "Deaths Linked to Growth Hormone" The Times (London), Apr. 6, 1991 (Cited for argument).
Qin et al, "Induction of classical transplantation tolerance in the adult", J. Exp. Med. 169(3):779-794 (1989).
Queen et al, "A humanized antibody that binds to the interleukin 2 receptor", PNAS 86:10029-10033 (1989).
Ramakrishnan, S. and L. L. Houston, "Comparison of the Selective Cytotoxic Effects of Immunotoxins Containing Ricin A Chain or Pokeweed Antiviral Protein and Anti-Thy 1.1 Monoclonal Antibodies," Cancer Research, 44, pp. 201-208 (Jan. 1984).
Rau, et al., "Longterm combination therapy of refractory and destructive rheumatoid arthritis with methotrexate (MTX) and intramuscular gold or other disease modifying antirheumatic drugs compared to MTX monotherapy", J. Rheumatol. 25(8): 1485-1492 (1998).
Reemtsma, "Xenografts", Transplantation Proceedings 21(1):517-518 (1989).
Reichlin, M., "Use of Glutaraldehyde as a Coupling Agent for Proteins and Peptides," In Methods in Enzymology, 70, edited by Van Vunakis et al., (Academic Press, New York, 1980) pp. 159-165 (1980).
Riechmann, et al., "Reshaping human antibodies for therapy", Nature 332:323-327 (1998).

Reimann et al.; "In Vivo Administration of Lymphocyte-Specific Monoclonal Antibodies in Nonhuman Primates" (Transplantation-Dec. 1989 pp. 906-912).
Richardson, N.E., et al., "Adhesion Domain of Human T11 (CD2) is Encoded by a Single Exon," Proc. Natl. Acad. Sci. (USA), 85, pp. 5176-5180 (1988).
Roitt, Immunology, Gower Medical Pub. (1985)—Immunology textbook.
Rose, "Risks of Cardiac Transplantation", Ann. Thoracic Surg. 47:645 (1989).
Rose, et al. "Immunosuppression in Cardiac Transplantation", Biblthca Cardiol. 43:1-9 (1988).
Rose, et al. "Humoral immune responses after cardiac transplantation: Correlation with fatal rejection and graft atheroscelerosi", Surgery 106(1):203-208 (1989).
Rose, et al., "Cardiac Xenotransplantation", Prog. Cardiovasc. Diseases 33(2):105-117 (1990).
Rose, et al., "Present Status of Human Cardiac Allografts and Prospects for Xenografts", Trans Am. Soc. Artif. Intern. Organs 34:19-23 (1988).
Rudinger, J. "Characteristics of the amino acids as components of a peptide hormone sequence" in Peptide Hormones, Parson, J. A. (Ed.), University Park Press, Baltimore, MD, pp. 1-7, 1976.
Sachs, et al., "Immunology of Xenograft Rejection", Hum. Immunol. 28:245-251 (1990).
Sanchez-Madrid, F. et al., "Three Distinct Antigens Associated with Human T-Lymphocyte-Mediated Cytolysis: LFA-1, LFA-2, and LFA-3," Proc. Natl. Acad. Sci, USA, 79, pp. 7489-7493 (Dec. 1982).
Sayre, et al. "Molecular cloning and expression of T11 cDNAs reveal a receptor-like structure on human T lymphocytes", PNAS 84:2941-2945 (1987).
Schneider, et al., (Abstract) "A pilot study of the safety and efficacy of Alefacept in subject with active rheumatoid arthritis on methotrexate" European League Against Rheumatism (2003).
Schopf, "Interactions between epidermal cells and lymphocytes in psoriasis", Immunology Today 7:358 (1988).
Schweighoffer, et al. "Adhesions cascades: diversity through combinatorial strategies", Curr. Opin. Cell. Biol. 4(5):824-829 (1991).
Selvaraj et al. "Deficiency of Lymphocyte Function Associated Antigen 3 (LFA3) in Paroxysmal Nocutrnal Hemoglobinuria," J. Exp. Med., 166, pp. 1011-1025 (1987).
Selvaraj et al. (1987) "The T Lymphocyte Glycoprotein CD2 (LFA-2/T11/E-Rosette Receptor) Binds The Cell Surface Ligand LFA-3" FASEB J. 46(3):447 Abstract 760.
Shaw, S. and G. E. Ginther Luce, "The Lymphocyte Function-Associated Antigen (LFA)-1 and CD2/LFA-3 Pathways of Antigen-Independent Human T Cell Adhesion," J. Immunol., 139, pp. 1037-1045 (Aug. 15, 1987).
Shimizu, et al "Four Molecular Pathways of T Cell Adhesion to Endothelial Cells: roles of :FA-1, VCAM-1 and Elam-1 and Changes in Pathway Hierarchy Under Different Activation Conditions", J. Cell. Biol. 113(5):1203-1212 (1991).
Short, J. M., et al., ".lambda. ZAP: A Bacteriophage Expression Vector with In Vivo Excision Properties," Nucleic Acids Research, 16(15), pp. 7583-7600 (1988).
Sofer and Britton "Designing an Optimal Chromatographic Purification Scheme for Proteins" Bio/Techniques 1(4):198-203 (1983).
Southern, E. M. "Detection of Specific Sequences Among DNA Fragments Separated by Gel Electrophoresis", J. Mol. Biol., 98, 503-517 (1975).
Spadaro, et al., "Comparison of cyclosporine A and methotrexate in the treatment of psoriatic arthritis: a one-year prospective study", Clin. Exp. Rheum. 13:589-593 (19950.
Srinivasachar, K. and d. M. Neville, Jr., "New Protein Cross-Linked Reagents That Are Cleaved by Mild Acid," Biochemistry, 28(4), pp. 2501-2509 (1989).
Stern, "Narrowband UV-B and Psoriasis", Arch Dermatol, vol. 133, pp. 1587-1588, 1997.
Strand, "The Future Use of Biologi Therapies in Combination for the Treatment of Rheumatoid Arthritis", J. Rhematol. 23 (suppl. 44):91-96 (1996).

Thomas, et al., "Purification of Membrane Proteins" in Methods in Enzymology, Deutscher, M. ed., (Academic Press, San Diego) 182: 499 (1990) (cited for argument).
Ticho, et al., "Reduced T cell monitoring in psoriasis patients receiving alefacept: results of clinical studies and mathematical modeling", J. Inves. Derm. 124(4): A40 (2005) (Abstract).
Uchio, et al., "Supression of Experimental Uveitis With Monoclonal Antibodies to ICAM-1 and LFA-1", invest. Opthamol. Vis. Sci. 35(5):2626-2631 (1994).
Van Nort, et al., "Cell Biology of Autoimmune Diseases", in International Review of Cytology: A Survey of Cell Biology, Jeon, K. ed. (Academic Press, San Diego, 1998), pp. 127-207.
Van Seventer, et al. "Roles of multiple accessory muleucles in T-cell activation", Curr. Opin. Immunol. 3(3):294-303 (1991).
Verhoeven, et al., "Combination Therapy in Rheumatoid Arthritis: Updated systematic review", Br. J. Rheum. 37:612-619 (1998).
Wallner et al (1987) "Primary Structure of Lymphocyte Function-Associated Antigen 3 (LFA-3)-The Ligand of the Lymphocyte CD2 Glycoprotein" J. Exp. Med. 166(4):923-932.
Wallner, et al., "Cloning and Expression of Human Lipocortin, a Phospholipase A2 inhibitor with Potential Anti-Inflammatory Activity", Nature, 320(6), 77-81 (1986).
Walters, et al., "Suberythemogenic narrow-band UVB is markedly more effective than conventional UVB in treatment of *Psoriasis vulgaris*", J.Acad. Dermatol. 40(6) 893-900.
Wang, X. et al., "A Vector That Expresses Secreted Proteins on the Cell Surface," DNA, 8(10), pp. 753-758 (Dec. 1989).
Watanabe, et al., "Effect of recombinant soluble CD4 in rhesus monkeys infected with simian immunodeficiency virus of macaques", Nature 337:267(1989) (cited for argument).
Weinblatt, "Efficacy of Methotrexate in Rheumatoid Arthritis" Br. J. Rheum. 34(S2)43-48 (1995).
Wendling, et al. "Therapeutic Use of Monoclonal Anti-CD4 Antibody in Rheumatoid Arthritis", J. Rheum. 18(3): 325-7 (1991) ) (abstract only).
Weyand, et al. "Immunosuppression by Anti-Cd4 Treatments In Vivo", Transplantation 47(6):1039-1042 (1989).
Whitcup, et al., "Monoclonal Antibodies aganist ICAM-1 (CD54) and LFA-1 (CD11a/CD18) Inhibit Experimental Autoimmune Uveitis", clin. Immunol Immunopathol 67(2):143-150 (1993).
Wong et al., "Identification of a Partial cDNA Clone for the Human Receptor for Completement Fragments C3b/C4b," Proc. Natl. Acad. Sci. U.S.A., 82, 7711-7715 (1985).
Wong, et al., "Mechanisms of action of cyclosporine A in the treatment of psoriasis", Immunol. Today 14(2):69-74 (1993).
Wood, W. I. (1987) "Gene Cloning Based on Long Oligoneucleotide Probes", Meth. Entymol. 152:443-47.
Written Opinion PCT/US02/02314.
Yamashita, et al., "A multimeric form of soluble recombinant sheep LFA-3 (CD-58) inhibits human T-cell proliferation" Immunol. 92(1):39-44 (1997).
Yeh, et al., "recombinant Soluble Human Complement Receptor Type 1 Inhibits Inflammation in the Reversed Passive Arthus Reaction in Rats", J. Immunol. 146(1):250 (1991) (cited for argument.
Zheng et al. (1990) "Expression of Intercellular Adhesion Molecule-1 And Lymphocyte Function-Associated Antigen-3 on Human Thyroid Epithelial Cells In Graves' And Hashimoto's Diseases" J. autoimmunity 3:727-736.
Translation of Examiner's report for Czech Patent Application No. PV 2001-725.
File history for U. S. Appl. No. 60/098,456, filed Aug. 31, 1998.
File history for U. S. Appl. No. 09/796,033, filed Feb. 27, 2001.
File history for International Application No. PCT/US99/20026, filed Aug. 31, 1999.
File history for U. S. Appl. No. 11/398,908, filed Apr. 6, 2006.
File history for U. S. Appl. No. 60/307,688, filed Jul. 24, 2001.
File history for U. S. Appl. No. 60/382,459, filed May 22, 2002.
File history for U. S. Appl. No. 10/484,329, filed Jul. 10, 2002.
File history for International Application No. PCT/US02/21631, filed Jul. 10, 2002.
File history for U. S. Appl. No. 60/568,371, filed May 4, 2004.

File history for International Application No. PCT/US05/15531, filed May 4, 2005.
File history for U. S. Appl. No. 11/578,342, filed May 4, 2005.
File history for U. S. Appl. No. 60/542,311, filed Feb. 6, 2004.
File history for International Application No. PCT/US05/03907, filed Feb. 6, 2005.
File history for U. S. Appl. No. 10/588,323, filed Feb. 7, 2005.
File history for U. S. Appl. No. 60/568,955, filed May 7, 2004.
File history for International Application No. PCT/US05/16265, filed May 9, 2005.
File history for U. S. Appl. No. 11/578,391, filed May 9, 2005.
File history for U. S. Appl. No. 07/667,971, filed Mar. 12, 1991.
File history for U. S. Appl. No. 07/770,967, filed Oct. 7, 1991.
File history for International Application No. PCT/US92/02050, filed Mar. 12, 1992.
File history for U. S. Appl. No. 07/940,861, filed Oct. 21, 1992.
File history for U. S. Appl. No. 08/459512, filed Jun. 2, 1995.
File history for U. S. Appl. No. 08/459,657, filed Jun. 2, 1995.
File history for U. S. Appl. No. 08/460,132, filed Jun. 2, 1995.
File history for U. S. Appl. No. 07/772,705, filed Oct. 7, 1991.
File history for U. S. Appl. No. 07/850,706, filed Mar. 12, 1992.
File history for International Application No. PCT/IS92/08754, filed Oct. 6, 1992.
File history for U. S. Appl. No. 08/211,631, filed Apr. 5, 1994.
File history for U. S. Appl. No. 08/459,350, filed Jun. 2, 1995.
File history for U. S. Appl. No. 07/770,969, filed Oct. 7, 1991.
File history for U. S. Appl. No. 07/862,022, filed Apr. 2, 1992.
File history for International Application No. PCT/US92/08755, filed Oct. 6, 1992.
File history for U. S. Appl. No. 08/466,465, filed Jun. 6, 1995.
File history for U. S. Appl. No. 09/730,465, filed Dec. 5, 2000.
File history for U. S. Appl. No. 11/282,853, filed Nov. 18, 2005.
File history for U. S. Appl. No. 60/265,964, filed Feb. 1, 2001.
File history for International Application No. PCT/US02/02314, filed Aug. 8, 2002.
File history for U. S. Appl. No. 10/470,764, filed Jan. 25, 2002.
File history for U. S. Appl. No. 10/329,599, filed Dec. 26, 2002.
File history for U. S. Appl. No. 11/312,627, filed Dec. 20, 2005.
File history for U. S. Appl. No. 07/057,615, filed Jun. 3, 1987.
File history for International Application No. PCT/US88/01924, filed Jun. 3, 1988.
File history for U. S. Appl. No. 07/365,107, filed Mar. 20, 1989.
File history for U. S. Appl. No. 07/537,031, filed Mar. 20, 1989.
File history for U. S. Appl. No. 08/381,299, filed Jan. 31, 1995.
File history for U. S. Appl. No. 07/237,309, filed Aug. 26, 1988.
File history for International Application No. PCT/US89/03652, filed Aug. 24, 1989.
File history for U. S. Appl. No. 07/959,550, filed Oct. 13, 1992.
File history for U. S. Appl. Nos. 08/261,463, filed Jun. 17, 1994 and 08/460,243, filed Jun. 2, 1995.
File history for U. S. Appl. No. 60/623,364, filed Oct. 28, 2004.
File history for International Application No. PCT/US05/39070.

* cited by examiner

METHODS OF TREATING SKIN CONDITIONS USING INHIBITORS OF THE CD2/LFA-3 INTERACTION

CROSS-REFERENCE TO RELATED APPLICATIONS

This application is a continuation of U.S. Ser. No. 09/730,465, filed Dec. 5, 2000, now U.S. Pat. No. 6,764,681, which is a continuation of U.S. Ser. No. 08/466,465, filed Jun. 6, 1995, now U.S. Pat. No. 6,162,432, which is a continuation-in-part of U.S. Ser. No. 07/862,022, filed Apr. 2, 1992, now abandoned, and of PCT/US92/08755, filed Oct. 6, 1992, which is a continuation-in-part of U.S. Ser. No. 07/770,969, filed Oct. 7, 1991, now abandoned, all of which are herein incorporated by reference.

TECHNICAL FIELD OF THE INVENTION

This invention relates to methods of using inhibitors of the CD2/LFA-3 interaction in treating skin conditions characterized by increased T cell activation and abnormal antigen presentation in the dermis and epidermis in mammals, including humans. Such conditions include psoriasis, UV damage, e.g., photoaging, atopic dermatitis, cutaneous T cell lymphoma such as mycosis fungoides, allergic and irritant contact dermatitis, lichen planus, alopecia areata, pyoderma gangrenosum, vitiligo, ocular cicatricial pemphigoid, and urticaria.

BACKGROUND OF THE INVENTION

There are numerous skin conditions characterized by increased T cell activation and abnormal antigen presentation in the dermis and epidermis. The pathophysiologic mechanisms involved in the evolution of such inflammatory processes are poorly understood. However, it has become apparent that skin cells are important in the generation of a cutaneous inflammatory response (Kupper, "Immune and Inflammatory Processes in Cutaneous Tissues", *J. Clin. Invest.*, 86, pp. 1783-89 (1990)).

The normal adult epidermal population contains 1-2% Langerhans' cells and about 98% keratinocytes. Keratinocytes and other nonhematopoietically-derived cells resident in skin contribute to immune homeostasis and can produce various cytokines which influence migration of T cells and expression of adhesion molecules.

As antigen presenting cells, Langerhans' cells express a high density of Class II major histocompatibility complex (MHC) antigen on the cell surface. MHC Class II molecules bind peptides derived from endocytosed antigen and are recognized primarily by helper T lymphocytes. The T cell receptor on T cells recognizes antigen as a peptide fragment bound to the cell-surface molecules encoded by the MHC (Springer, "Adhesion Receptors of the Immune System", *Nature*, 346, pp. 425-27 (1990)).

There are many interactions between molecules expressed on the surface of Langerhans' cells and the surface of T cells, in addition to the T cell receptor/MHC interaction. These surface molecules, often referred to as adhesion molecules, participate in a number of functions including cellular adhesion, antigen recognition, co-stimulatory signalling in T cell activation and stimulation of effectors of T cell cytotoxicity ("Adhesion Molecules in Diagnosis and Treatment of Inflammatory Diseases", *The Lancet*, 336, pp. 1351-52 (1990)). Such cell adhesion appears to be involved in activation of T cell proliferation in the generation of an immune response (Hughes et al., "The Endothelial Cell as a Regulator of T-cell Function", *Immunol. Rev.*, 117, pp. 85-102 (1990)).

Various skin conditions are characterized by increased T cell activation and abnormal antigen presentation in the dermis and epidermis (Cooper, "Immunoregulation in the Skin", in *Cutaneous Lymphoma, Curr. Probl. Dermatol.*, eds. van Vloten et al., 19, pp. 69-80 at pp. 73, 74, 76 (1990)). For example, in contact allergic dermatitis, activation of intracutaneous T cells is observed. It is known that skin from patients exhibiting atopic dermatitis contains an increased number of Langerhans' cells (Cooper, "Immunoregulation in the Skin", in *Cutaneous Lymphoma, Curr. Probl. Dermatol.*, eds. van Vloten et al., 19, at p. 74 (1990)). In psoriatic skin, there is an increased number of antigen presenting cells, composed of both Langerhans' cells and non-Langerhans' cell Class II MHC-bearing antigen presenting cells (Cooper, "Immunoregulation in the Skin", in *Cutaneous Lymphoma, Curr. Probl. Dermatol.*, eds. van Vloten et al., 19, at p. 75 (1990)).

UV exposed skin is characterized by an overall depletion of Langerhans' cells and migration of a non-Langerhans' cell antigen-presenting cell population into the epidermis, which activates autologous T cells to proliferate (Cooper, "Immunoregulation in the Skin" in *Cutaneous Lymphoma, Curr. Probl. Dermatol.*, eds. van Vloten et al., 19, at pp. 75-76 (1990)). In human skin after 4 minimal erythemal doses of UV B, Langerhans' cells (the constitutive antigen presenting cell population) are inactivated for approximately 3 days (Cooper et al., "Effects Of Ultraviolet Radiation On Human Epidermal Cell Alloantigen Presentation: Initial Depression Of Langerhans Cell-Dependent Function Is Followed By Appearance Of T6-DR$^+$ Cells That Enhance Epidermal Alloantigen Presentation", *J. Immunol.*, 134, pp. 129-37 (1985)). In this type of UV damaged skin, the CD1a-DR$^+$ macrophage population (a population of antigen presenting cells) increases from 0% (normal skin) to approximately 2-10% of the entire epidermal cell population and is the cell population entirely responsible for the induction of T cell proliferation to alloantigen. (Cooper et al., *J. Immunol.*, supra (1985); Baadsgaard et al., "In Vivo Ultraviolet-Exposed Human Epidermal Cells Activate T Suppressor Cell Pathways That Involve CD4$^+$ CD45RA$^+$ Suppressor-Inducer T Cells", *J. Immunol.*, 145, pp. 2854-61 (1990)).

Cutaneous T cell lymphoma is characterized by the expansion of a malignant clonal population of T cells in the dermis and epidermis. Lesional epidermal cells contain increased numbers of CD1$^+$DR$^+$ antigen presenting cells (Cooper, "Immunoregulation in the Skin" in *Cutaneous Lymphoma, Curr. Probl. Dermatol.*, eds. van Vloten et al., 19, at pp. 76-77 (1990)).

Presently known therapies for the above mentioned skin diseases are inadequate. Steroids or cyclosporin A are commonly used in the treatment of psoriasis, lichen planus, urticaria, atopic dermatitis, UV damage, pyoderma gangrenosum, vitiligo, ocular cicatricial pemphigoid, alopecia areata, allergic and irritant contact dermatitis and cutaneous T cell lymphoma. In addition, for some of these skin conditions, various therapies include retinoids, PUVA, nitrogen mustard, interferon, chemotherapy, methotrexate, UV light, antibiotics and antihistamines. See generally Fitzpatrick, *Dermatology in General Medicine*, 3rd ed., McGraw Hill (1987).

Side effects to these therapies are known. Most commonly encountered drawbacks for cyclosporin A include toxicity due to immunosuppression and renal and neural toxicity. Steroids have well known side effects including induction of Cushing Syndrome. Side effects of certain of the other aforementioned therapies include skin cancer, bone marrow and constitutional toxicities, ligament calcification, liver fibrosis and other disorders.

T cells play a major role in the immune response by interacting with target and antigen presenting cells. For example, T cell-mediated killing of target cells is a multi-step process involving, initially, adhesion of cytolytic T cells (the effector cells) to target cells. Also, helper T cells help initiate the immune response by adhesion to antigen presenting cells.

These interactions of T cells with target and antigen presenting cells are highly specific and depend on the recognition of an antigen on the surface of a target or antigen presenting cell by one of the many specific antigen receptors on the surface of T cells.

The receptor-antigen interaction of T cells and other cells is also facilitated by various T cell surface proteins, e.g., the antigen-receptor complex CD3 and accessory adhesion molecules such as CD4, LFA-1, CD8, and CD2. It is also facilitated by accessory adhesion molecules, such as LFA-3, ICAM-1 and MHC, that are expressed on the surface of the target or antigen presenting cells. For example, LFA-1 and its counter receptor ICAM-1 or ICAM-2, as well as CD2 and its counter receptor LFA-3 have been implicated in cellular adhesion and T cell activation. It is known that the LFA-1/ICAM and CD2/LFA-3 interactions are independent.

A number of other molecules present on resting T cells have also been implicated in T cell adhesion, including E2 (MIC2), VLA-4 (CD49d), CD44 (Hermes, Pgp-1, ECM-RIII), and H19 (N4) (see Makgoba et al., "The CD2-LFA-3 and LFA-1-ICAM Pathways: Relevance to T-cell Recognition", *Immunol. Today*, 10, pp. 417-22 (1989)).

One way in which T cells are activated is by binding of their antigen specific T cell receptors to peptide-MHC complexes on the surface of antigen presenting cells such as macrophages. T cell activation stimulates proliferation and differentiation of two types of functional T cells: helper cells, which promote the proliferation and maturation of antibody-producing B lymphocytes, and killer cells, which lyse target cells (Bierer et al., "A Monoclonal Antibody to LFA-3, the CD2 Ligand, Specifically Immobilizes Major Histocompatibility Complex Proteins", *Eur. J. Immunol.*, 19, pp. 661-65 (1989); Springer "Adhesion Receptors of the Immune System", *Nature*, 346, pp. 425-34 (1990)).

The interaction between CD2 and LFA-3 remains poorly understood with respect to activation of T cell activity. Recent studies have suggested that there is a specific interaction between CD2 (a T cell adhesion molecule) and LFA-3 (a target cell and antigen presenting cell adhesion molecule) which mediates T cell adhesion to the target or antigen presenting cells. This cell-cell adhesion has been implicated in the initiation of T cell functional responses (Dustin et al., "Purified Lymphocyte Function Associated Antigen 3 Binds to CD2 and Mediates T Lymphocyte Adhesion," *J. Exp. Med.*, 165, pp. 677-92 (1987); Springer et al., "The Lymphocyte Function-associated LFA-1, CD2, and LFA-3 Molecules: Cell Adhesion Receptors of the Immune System", *Ann. Rev. Immunol.*, 5, pp. 223-52 (1987)).

LFA-3, which is found on the surface of a wide variety of cells, including human erythrocytes, has become the subject of a considerable amount of study to further elucidate its role in various T cell interactions (see, e.g., Krensky et al., "The Functional Significance, Distribution, and Structure of LFA-1, LFA-2, and LFA-3: Cell Surface Antigen Associated with CTL-Target Interactions", *J. Immunol.*, 131(2), pp. 611-16 (1983); Shaw et al., "Two Antigen-Independent Adhesion Pathways Used by Human Cytotoxic T-cell Clones", *Nature*, 323, pp. 262-64 (1986)). Two natural forms of LFA-3 have been identified. One form of LFA-3 ("transmembrane LFA-3") is anchored in the cell membrane by a transmembrane hydrophobic domain. cDNA encoding this form of LFA-3 has been cloned and sequenced (see, e.g., Wallner et al., "Primary Structure of Lymphocyte Function-Associated Antigen-3 (LFA-3)", *J. Exp. Med.*, 166, pp. 923-32 (1987)). Another form of LFA-3 is anchored to the cell membrane via a covalent linkage to phosphatidylinositol ("PI")-containing glycolipid. This latter form has been designated "PI-linked LFA-3", and cDNA encoding this form of LFA-3 has also been cloned and sequenced (Wallner et al., PCT Publn. WO 90/02181).

The human CD2 (T11) molecule is a 50 kD surface glycoprotein expressed on >95% of thymocytes and virtually all peripheral T lymphocytes. Biochemical analyses using specific monoclonal antibodies have suggested that CD2 is T lineage-specific and exists on the cell surface in several differentially glycosylated forms (Howard et al., "A Human T Lymphocyte Differentiation Marker Defined by Monoclonal Antibodies that Block E-Rosette Formation", *J. Immunol.*, 126, pp. 2117-22 (1981); Brown et al., in *Leukocyte Typing III*, ed. McMichael, Oxford University Press, pp. 110-12 (1987); Sayre et al., "Molecular Cloning and Expression of T11 cDNAs Reveals a Receptor-Like Structure on Human T Lymphocytes", *Proc. Natl. Acad. Sci. USA*, 84, pp. 2941-45 (1987)).

The sequence of a human CD2 gene has been reported (Seed and Aruffo, "Molecular Cloning of the CD2 Antigen, the T-cell Erythrocyte Receptor, by a Rapid Immunoselection Procedure", *Proc. Natl. Acad. Sci. USA*, 84, pp. 3365-69 (1987); Sayre et al., "Molecular Cloning and Expression of T11 cDNAs Reveal a Receptor-like Structure on Human T Lymphocytes", *Proc. Natl. Acad. Sci. USA*, 84, pp. 2941-45 (1987)). CD2 cDNA clones predict a cleaved signal peptide of 24 amino acid residues, an extracellular segment of 185 residues, a transmembrane domain of 25 residues and a cytoplasmic region of 117 residues (Sayre et al., supra (1987); Sewell et al., "Molecular Cloning of the Human T-Lymphocyte Surface CD2 (T11) Antigen", *Proc. Natl. Acad. Sci. USA*, 83, pp. 8718-22 (1986); Seed and Aruffo, supra (1987); Clayton et al., *Eur. J. Immunol.*, 17, pp. 1367-70 (1987)).

Soluble CD2 polypeptides having an LFA-3 binding domain have been reported (PCT Publn. WO 90/08187).

Monoclonal antibodies to CD2, for example TS2/18, $T11_1$, $T11_2$, $T11_3$, and to LFA-3, for example TS2/9, have also been reported (see, e.g., Hughes et al., "The Endothelial Cell as a Regulator of T-Cell Function", *Immunol. Reviews*, 117, pp. 85-102 (1990); Meuer, "An Alternative Pathway of T-Cell Activation: A Functional Role for the 50 kD T11 Sheep Erythrocyte Receptor Protein", *Cell*, 36, pp. 897-906 (1984)).

The need still exists for improved methods of preventing and treating skin conditions exhibiting increased T cell activation and abnormal antigen presentation.

SUMMARY OF THE INVENTION

The present invention generally solves many of the problems referred to above. It for the first time provides a method of preventing or treating skin conditions, characterized by increased T cell activation and abnormal antigen presentation in the dermis and epidermis, in a mammal, whereby an inhibitor of the CD2/LFA-3 interaction, is administered to the mammal. The methods of this invention are superior to previously available therapies for these skin conditions for many reasons, including less immunosuppression than pre-existing therapies and more specific therapy with less general toxicity.

The method of the present invention preferably will be used in the treatment or prophylaxis of skin conditions selected from psoriasis, UV damage, e.g., photoaging, atopic dermatitis, cutaneous T cell lymphoma such as mycosis fungoides, allergic and irritant contact dermatitis, lichen planus, alopecia areata, pyoderma gangrenosum, vitiligo, ocular cicatricial pemphigoid, and urticaria, preferably psoriasis or UV damage.

Inhibitors that can be used in accordance with the method of the present invention include any molecule that inhibits the CD2/LFA-3 interaction. Preferably, the inhibitor is selected from the group consisting of anti-LFA-3 antibody homologs, anti-CD2 antibody homologs, soluble LFA-3 polypeptides, small molecules, e.g., carbohydrates, soluble CD2 polypeptides, CD2 or LFA-3 mimetic agents and derivatives thereof.

DETAILED DESCRIPTION OF THE INVENTION

Definitions

Figure 1:
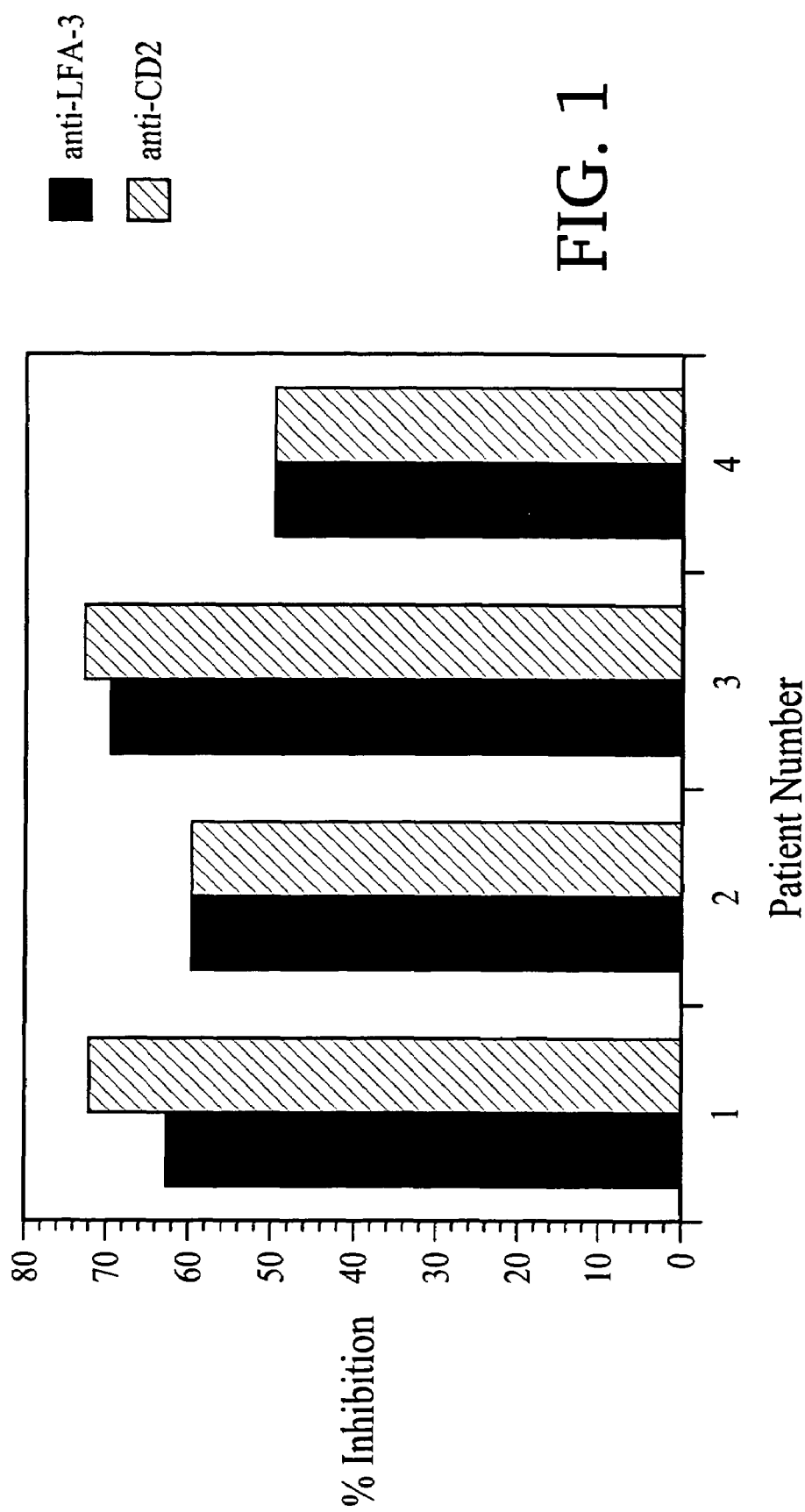
FIG. 1 illustrates the percent inhibition caused by an anti-LFA-3 monoclonal antibody (7A6) or an anti-CD2 monoclonal antibody (TS2/18) as compared to a non-specific control IgG$_1$ antibody (MOPC21) of autologous T cell activation by psoriatic epidermal cells in 4 patients.

As used herein, "CD2" means a CD2 polypeptide that binds to a naturally occurring LFA-3 polypeptide and which is encoded by (a) a naturally occurring mammalian CD2 DNA sequence (e.g., SEQ ID NO:5); (b) a DNA sequence degenerate to a naturally occurring CD2 DNA sequence; or (c) a DNA sequence that hybridizes to one of the foregoing DNA sequences under conditions equivalent to about 20° C. to 27° C. below $T_m$ and 1 M sodium chloride.

As used herein, "LFA-3" means an LFA-3 polypeptide that binds to a naturally occurring CD2 polypeptide and which is encoded by (a) a naturally occurring mammalian LFA-3 DNA sequence (e.g., SEQ ID NO:1 or SEQ ID NO:3); (b) a DNA sequence degenerate to a naturally occurring LFA-3 DNA sequence; or (c) a DNA sequence that hybridizes to one of the foregoing DNA sequences under conditions to about 20° C. to 27° C. below $T_m$ and 1 M sodium chloride.

As used herein, a "soluble LFA-3 polypeptide" or a "soluble CD2 polypeptide" is an LFA-3 or CD2 polypeptide incapable of anchoring itself in a membrane. Such soluble polypeptides include, for example, CD2 and LFA-3 polypeptides that lack a sufficient portion of their membrane spanning domain to anchor the polypeptide or are modified such that the membrane spanning domain is non-functional. As used herein soluble LFA-3 polypeptides include full-length or truncated (e.g., with internal deletions) PI-linked LFA-3.

As used herein, an "antibody homolog" is a protein comprising one or more polypeptides selected from immunoglobulin light chains, immunoglobulin heavy chains and antigen-binding fragments thereof which are capable of binding to one or more antigens. The component polypeptides of an antibody homolog composed of more than one polypeptide may optionally be disulfide-bound or otherwise covalently crosslinked. Accordingly, antibody homologs include intact immunoglobulins of types IgA, IgG, IgE, IgD, IgM (as well as subtypes thereof), wherein the light chains of the immunoglobulin may be of types kappa or lambda. Antibody homologs also include portions of intact immunoglobulins that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like.

As used herein, a "humanized recombinant antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain.

As used herein, a "chimeric recombinant antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain.

Skin Conditions

The methods of this invention are useful to prevent or treat mammalian, including human, skin conditions characterized by increased T cell activation and abnormal antigen presentation in the dermis and epidermis, by administering inhibitors of the CD2/LFA-3 interaction. Such conditions include psoriasis, UV damage, atopic dermatitis, cutaneous T cell lymphoma such as mycosis fungoides, allergic and irritant contact dermatitis, lichen planus, alopecia areata, pyoderma gangrenosum, vitiligo, ocular cicatricial pemphigoid, and urticaria. It is to be understood that methods of treatment and prophylaxis of skin conditions such as pyoderma gangrenosum and urticaria are included within the scope of the present invention. These latter skin conditions are also cyclosporin A sensitive dermatoses and therefore involve T cell activation. Preferably, the methods of the invention are used in the prophylaxis or treatment of psoriasis or UV damage. The methods of the invention may be practiced on any mammal, preferably on humans.

While not wishing to be bound by theory, applicants believe that inhibitors of the CD2/LFA-3 interaction used in accordance with the methods of this invention are prophylactic and therapeutic for the treatment of the aforementioned skin conditions because they inhibit the interaction between T cells and antigen presenting cells, resulting in, among other things, an inhibition of T cell proliferation and activation. Applicants believe that adverse effects of skin conditions of the type discussed herein are due to such T cell proliferation and activation. Applicants believe that the methods of the present invention are superior to previously available therapies for these skin conditions for a number of reasons, including, inhibition of antigen specific interactions for all antigens present, inhibition of T cell activation, no general immunosuppression and, possibly, induction of tolerance.

In particular, applicants believe that use of the methods of this invention will result in more specific targeting of therapy to T cells actually in the initiating stage of the lesion with no effect on polymorphonuclear leukocytes or macrophage mediated effector mechanisms. Accordingly, the patient will be less susceptible to infections than with steroids or other general immunosuppressants. Thus, methods of inhibiting T cell activation, as provided herein, are prophylactic and therapeutic for such skin conditions.

Inhibitors Of The CD2/LFA-3 Interaction

Any inhibitor of the CD2/LFA-3 interaction is useful in the methods of this invention. Such inhibitors include anti-LFA-3 antibody homologs, anti-CD2 antibody homologs, soluble LFA-3 polypeptides, soluble CD2 polypeptides, small molecules, e.g., carbohydrates, LFA-3 and CD2 mimetic agents and derivatives thereof. Preferred inhibitors are soluble LFA-3 polypeptides and anti-LFA-3 antibody homologs.

The utility in the methods of this invention of specific soluble CD2 polypeptides, soluble LFA-3 polypeptides, anti-LFA-3 antibody homologs, anti-CD2 antibody homologs or CD2 and LFA-3 mimetic agents may easily be determined by assaying their ability to inhibit the LFA-3/CD2 interaction. This ability may be assayed, for example, using a simple cell binding assay that permits visual (under magnification) evaluation of the ability of the putative inhibitor to inhibit the interaction between LFA-3 and CD2 on cells bearing these molecules. Jurkat cells are preferred as the $CD2^+$ substrate and sheep red blood cells or human JY cells are preferred as the $LFA-3^+$ substrate. The binding characteristics of soluble polypeptides, antibody homologs and mimetic agents useful in this invention may be assayed in several known ways, such as by radiolabeling the antibody homolog, polypeptide or agent (e.g., $^{35}S$ or $^{125}I$) and then contacting the labeled polypeptide, mimetic agent or antibody homolog with $CD2^+$ of $LFA-3^+$ cells, as appropriate. Binding characteristics may also be assayed using an appropriate enzymatically labelled secondary antibody. Rosetting competition assays such as those described by Seed et al. (*Proc. Natl. Acad. Sci. USA*, 84, pp. 3365-69 (1987)) may also be used.

A. Anti-LFA-3 And Anti-CD2 Antibody Homologs

Many types of anti-LFA-3 or anti-CD2 antibody homologs are useful in the methods of this invention. These include monoclonal antibodies, recombinant antibodies, chimeric recombinant antibodies, humanized recombinant antibodies, as well as antigen-binding portions of the foregoing.

Among the anti-LFA-3 antibody homologs, it is preferable to use monoclonal anti-LFA-3 antibodies. It is more preferable to use a monoclonal anti-LFA-3 antibody produced by a hybridoma selected from the group of hybridomas having Accession Nos. ATCC HB 10693 (1E6), ATCC HB 10694 (HC-1B11), ATCC HB 10695 (7A6), and ATCC HB 10696 (8B8), or the monoclonal antibody known as TS2/9 (Sanchez-Madrid et al., "Three Distinct Antigens Associated with Human T-Lymphocyte-Mediated Cytolysis: LFA-1, LFA-2 and LFA-3", Proc. Natl. Acad. Sci. USA, 79, pp. 7489-93 (1982)). Most preferably, the monoclonal anti-LFA-3 antibody is produced by a hybridoma selected from the group of hybridomas having Accession Nos. ATCC HB 10695 (7A6) and ATCC HB 10693 (1E6).

Among the anti-CD2 antibody homologs, it is preferable to use monoclonal anti-CD2 antibodies, such as the anti-CD2 monoclonal antibodies known as the $T11_1$ epitope antibodies, including TS2/18 (Sanchez-Madrid et al., "Three Distinct Antigens Associated with Human T-Lymphocyte-Mediated Cytolysis: LFA-1, LFA-2 and LFA-3", Proc. Natl. Acad. Sci. USA, 79, pp. 7489-93 (1982)).

The technology for producing monoclonal antibodies is well known. Briefly, an immortal cell line (typically myeloma cells) is fused to lymphocytes (typically splenocytes) from a mammal immunized with preparation comprising a given antigen, and the culture supernatants of the resulting hybridoma cells are screened for antibodies against the antigen. See generally, Kohler et al., Nature, "Continuous Cultures of Fused Cells Secreting Antibody of Predefined Specificity", 256, pp. 495-97 (1975). Useful immunogens for the purpose of this invention include CD2- or LFA-3-bearing cells, as well as cell free preparations containing LFA-3, CD2 or counter receptor-binding fragments thereof (e.g., CD2 fragments that bind to LFA-3 or LFA-3 fragments that bind to CD2).

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, useful anti-LFA-3 or anti-CD2 antibodies may be identified by testing the ability of the immune serum to block sheep red blood cell rosetting of Jurkat cells, which results from the presence of LFA-3 and CD2 on the respective surfaces of these cells. The lymphocytes used in the production of hybridoma cells typically are isolated from immunized mammals whose sera have already tested positive for the presence of the desired antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium").

Typically, HAT-sensitive mouse myeloma cells are fused to mouse splenocytes using polyethylene glycol ("PEG") 3350. Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants, for example, for the ability to bind to their respective counter receptor, or for their ability to block Jurkat cell adhesion to sheep red blood cells. Subcloning of the hybridoma cultures by limiting dilution is typically performed to ensure monoclonality.

To produce anti-LFA-3 or anti-CD2 monoclonal antibodies, hybridoma cells that tested positive in such screening assays are cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the desired antibodies optionally further purified by well-known methods.

Alternatively, the desired antibody may be produced by injecting the hybridoma cells into the peritoneal cavity of a pristane-primed mouse. The hybridoma cells proliferate in the peritoneal cavity, secreting the antibody, which accumulates as ascites fluid. The antibody may be harvested by withdrawing the ascites fluid from the peritoneal cavity with a syringe.

Anti-CD2 and anti-LFA-3 antibody homologs useful in the present invention may also be recombinant antibodies produced by host cells transformed with DNA encoding immunoglobulin light and heavy chains of a desired antibody. Recombinant antibodies may be produced by well known genetic engineering techniques. See, e.g., U.S. Pat. No. 4,816,397, which is incorporated herein by reference.

For example, recombinant antibodies may be produced by cloning cDNA or genomic DNA encoding the immunoglobulin light and heavy chains of the desired antibody from a hybridoma cell that produces an antibody homolog useful in this invention. The cDNA or genomic DNA encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector.

Prokaryotic or eukaryotic host cells may be used. Expression in eukaryotic host cells is preferred because such cells are more likely than prokaryotic cells to assemble and secrete a properly folded and immunologically active antibody. However, any antibody produced that is inactive due to improper folding may be renaturable according to well known methods (Kim and Baldwin, "Specific Intermediates in the Folding Reactions of Small Proteins and the Mechanism of Protein Folding", *Ann. Rev. Biochem.*, 51, pp. 459-89 (1982)). It is possible that the host cells will produce portions of intact antibodies, such as light chain dimers or heavy chain dimers, which also are antibody homologs according to the present invention.

It will be understood that variations on the above procedure are useful in the present invention. For example, it may be desired to transform a host cell with DNA encoding either the light chain or the heavy chain (but not both) of an antibody homolog. Recombinant DNA technology may also be used to remove some or all of the DNA encoding either or both of the light and heavy chains that is not necessary for CD2 or LFA-3 counter receptor binding. The molecules expressed from such truncated DNA molecules are useful in the methods of this invention. In addition, bifunctional antibodies may be produced in which one heavy and one light chain are anti-CD2 or anti-LFA-3 antibody homologs and the other heavy and light chain are specific for an antigen other than CD2 or LFA-3, or another epitope of CD2 or LFA-3.

Chimeric recombinant anti-LFA-3 or anti-CD2 antibody homologs may be produced by transforming a host cell with a suitable expression vector comprising DNA encoding the desired immunoglobulin light and heavy chains in which all or some of the DNA encoding the hinge and constant regions of the heavy and/or the light chain have been substituted with DNA from the corresponding region of an immunoglobulin light or heavy chain of a different species. When the original recombinant antibody is nonhuman, and the inhibitor is to be administered to a human, substitution of corresponding human sequences is preferred. An exemplary chimeric recombinant antibody has mouse variable regions and human hinge and constant regions. See generally, U.S. Pat. No. 4,816,397 and Morrison et al., "Chimeric Human Antibody Molecules: Mouse Antigen-Binding Domains With Human Constant Region Domains", *Proc. Natl. Acad. Sci. USA*, 81, pp. 6851-55 (1984).

Humanized recombinant anti-LFA-3 or anti-CD2 antibodies may be produced by transforming a host cell with a suitable expression vector comprising DNA encoding the desired nonhuman immunoglobulin light and heavy chains in which all or some of the DNA encoding amino acids not involved in antigen binding have been substituted with DNA from the corresponding region of a desired human immunoglobulin light or heavy chain. See generally, Jones et al., "Replacing the Complementarity-Determining Regions in a Human Antibody with Those from a Mouse", *Nature*, 321, pp. 522-25 (1986).

Anti-CD2 and anti-LFA-3 antibody homologs that are not intact antibodies are also useful in this invention. Such homologs may be derived from any of the antibody homologs described above. For example, antigen-binding fragments, as well as full-length monomeric, dimeric or trimeric polypeptides derived from the above-described antibodies are themselves useful. Useful antibody homologs of this type include Fab fragments, Fab' fragments, F(ab')$_2$ fragments, F(v) fragments, heavy chain monomers or dimers, light chain monomers or dimers, dimers consisting of one heavy and one light chain, and the like. Anti-LFA-3 heavy chains are preferred anti-LFA-3 antibody fragments.

Antibody fragments may also be produced by chemical methods, e.g., by cleaving an intact antibody with a protease, such as pepsin or papain, and optionally treating the cleaved product with a reducing agent. Alternatively, useful fragments may be produced by using host cells transformed with truncated heavy and/or light chain genes. Heavy and light chain monomers may be produced by treating an intact antibody with a reducing agent, such as dithiothreitol, followed by purification to separate the chains. Heavy and light chain monomers may also be produced by host cells transformed with DNA encoding either the desired heavy chain or light chain, but not both. See, e.g., Ward et al., "Binding Activities of a Repertoire of Single Immunoglobulin Variable Domains Secreted from *Escherichia coli*", *Nature*, 341, pp. 544-46 (1989); Sastry et al., "Cloning of the Immunological Repertoire in *Escherichia coli* for Generation of Monoclonal Catalytic Antibodies: Construction of a Heavy Chain Variable Region-Specific cDNA Library", *Proc. Natl. Acad. Sci. USA*, 86, pp. 5728-32 (1989).

B. Soluble CD2 and LFA-3 Polypeptides

Soluble LFA-3 polypeptides or soluble CD2 polypeptides that inhibit the interaction of LFA-3 and CD2 are useful in the methods of the present invention. Soluble LFA-3 polypeptides are preferred.

Soluble LFA-3 polypeptides may be derived from the transmembrane form of LFA-3, particularly the extracellular domain (e.g., $AA_1$-$AA_{187}$ of SEQ ID NO:2). Such polypeptides are described in U.S. Pat. No. 4,956,281 and co-pending U.S. patent application Ser. No. 07/667,971 (which shares a common assignee with the present application), which are herein incorporated by reference. Preferred soluble LFA-3 polypeptides include polypeptides consisting of $AA_1$-$AA_{92}$ of SEQ ID NO:2, $AA_1$-$AA_{80}$ of SEQ ID NO:2, $AA_{50}$-$AA_{65}$ of SEQ ID NO:2 and $AA_{20}$-$AA_{80}$ of SEQ ID NO:2. A vector comprising a DNA sequence encoding SEQ ID NO:2 (i.e., SEQ ID NO:1) is deposited with the American Type Culture Collection under Accession No. 75107.

The most preferred fusion proteins of this type contain the amino terminal 92 amino acids of mature LFA-3, the C-terminal 10 amino acids of a human IgG1 hinge region containing the two cysteine residues thought to participate in interchain disulfide bonding, and the $C_{H}2$ and $C_{H}3$ regions of a human IgG.sub.1 heavy chain constant domain (e.g., SEQ ID NO:8). This fusion protein is referred to herein as "LFA3TIP." A plasmid, pSAB152, encoding an exemplary LFA3TIP was deposited with American Type Culture Collection on Oct. 1, 1991, under the accession number ATCC 68720. The DNA sequence of the pSAB152 insert is SEQ ID NO:7.

One way of producing LFA3TIP for use in the methods of this invention is described in co-pending, commonly assigned U.S. patent application Ser. No. 07/770,967. Generally, conditioned culture medium of COS7 or CHO cells transfected with pSAB152 was concentrated using an AMICON® S1Y30 spiral cartridge system (AMICON®., Danvers, Mass.) and subjected to Protein A-Sepharose 4B® (Sigma, St. Louis, Mo.) chromatography. The bound proteins were eluted and subjected to Superose-12™(Pharmacia/LKB, Piscataway, N.J.) gel filtration chromatography.

Superose-12™ fractions containing LFA3TIP with the least amount of contaminating proteins, as determined on SDS-PAGE gels and by Western blot analysis, (see, e.g., Towbin et al., Proc. Natl. Acad. Sci. USA, 74, pp. 4350-54 (1979); Antibodies: A Laboratory Manual, pp. 474-510 (Cold Spring Harbor Laboratory (1988)), were pooled and concentrated in a YM30 Centricon (AMICON.RTM.). LFA3TIP was detected on Western blots using a rabbit anti-LFA-3 polyclonal antiserum, followed by detectably labeled goat anti-rabbit IgG. The purified LFA3TIP of COS7 or CHO cells was a dimer of two monomeric LFA-3-Ig fusion proteins, connected by disulfide bonds.

Another preferred fusion protein consists of the first and second LFA-3 domain fused to the hinge $C_{H}2$ and $C_{H}3$ regions of human IgG1, herein referred to as LLFA3-Ig.

Soluble LFA-3 polypeptides may also be derived from the PI-linked form of LFA-3, such as those described in PCT Patent Application Ser. No. WO 90/02181. A vector comprising a DNA sequence encoding PI-linked LFA-3 (i.e., SEQ ID NO:3) is deposited with the American Type Culture Collection under Accession No. 68788. It is to be understood that the PI-linked form of LFA-3 and the transmembrane form of LFA-3 have identical amino acid sequences through the entire extracellular domain. Accordingly, the preferred PI-linked LFA-3 polypeptides are the same as for the transmembrane form of LFA-3.

Soluble CD2 polypeptides may be derived from full length CD2, particularly the extracellular domain (e.g., $AA_1$-$AA_{185}$ of SEQ ID NO:6). Such polypeptides may comprise all or part of the extracellular domain of CD2. Exemplary soluble CD2 polypeptides are described in PCT WO 90/08187, which is herein incorporated by reference.

The production of the soluble polypeptides useful in this invention may be achieved by a variety of methods known in the art. For example, the polypeptides may be derived from intact transmembrane LFA-3 or CD2 molecules or an intact PI-linked LFA-3 molecule by proteolysis using specific endopeptidases in combination with exopeptidases, Edman degradation, or both. The intact LFA-3 molecule or the intact CD2 molecule, in turn, may be purified from its natural source using conventional methods. Alternatively, the intact LFA-3 or CD2 may be produced by known recombinant DNA techniques using cDNAs (see, e.g., U.S. Pat. No. 4,956,281 to Wallner et al.; Aruffo and Seed, *Proc. Natl. Acad. Sci.*, 84, pp. 2941-45 (1987); Sayre et al., *Proc. Natl. Acad. Sci. USA*, 84, pp. 2941-45 (1987)).

Preferably, the soluble polypeptides useful in the present invention are produced directly, thus eliminating the need for an entire LFA-3 molecule or an entire CD2 molecule as a starting material. This may be achieved by conventional chemical synthesis techniques or by well-known recombinant DNA techniques wherein only those DNA sequences which encode the desired peptides are expressed in transformed hosts. For example, a gene which encodes the desired soluble LFA-3 polypeptide or soluble CD2 polypeptide may be synthesized by chemical means using an oligonucleotide synthesizer. Such oligonucleotides are designed based on the amino acid sequence of the desired soluble LFA-3 polypeptide or soluble CD2 polypeptide. Specific DNA sequences coding for the desired peptide also can be derived from the full length DNA sequence by isolation of specific restriction endonuclease fragments or by PCR synthesis of the specified region.

Standard methods may be applied to synthesize a gene encoding a soluble LFA-3 polypeptide or a soluble CD2 polypeptide that is useful in this invention. For example, the complete amino acid sequence may be used to construct a back-translated gene. A DNA oligomer containing a nucleotide sequence coding for a soluble LFA-3 polypeptide or a soluble CD2 polypeptide useful in this invention may be synthesized in a single step. Alternatively, several smaller oligonucleotides coding for portions of the desired polypeptide may be synthesized and then ligated. Preferably, a soluble LFA-3 polypeptide or a soluble CD2 polypeptide useful in this invention will be synthesized as several separate oligonucleotides which are subsequently linked together. The individual oligonucleotides typically contain 5' or 3' overhangs for complementary assembly.

Once assembled, preferred genes will be characterized by sequences that are recognized by restriction endonucleases (including unique restriction sites for direct assembly into a cloning or an expression vector), preferred codons taking into consideration the host expression system to be used, and a sequence which, when transcribed, produces a stable, efficiently translated mRNA. Proper assembly may be confirmed by nucleotide sequencing, restriction mapping, and expression of a biologically active polypeptide in a suitable host.

It will be appreciated by those of skill in the art that, due to the degeneracy of the genetic code, DNA molecules comprising many other nucleotide sequences will also be capable of encoding the soluble LFA-3 and CD2 polypeptides encoded by the specific DNA sequences described above. These degenerate sequences also code for polypeptides that are useful in this invention.

The DNA sequences may be expressed in unicellular hosts. As is well known in the art, in order to obtain high expression levels of a transfected gene in a host, the gene must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an additional expression marker useful in the expression host.

The DNA sequences encoding the desired soluble polypeptides may or may not encode a signal sequence. If the expression host is prokaryotic, it generally is preferred that the DNA sequence not encode a signal sequence. If the expression host is eukaryotic, it generally is preferred that a signal sequence be encoded.

An amino terminal methionine may or may not be present on the expressed product. If the terminal methionine is not cleaved by the expression host, it may, if desired, be chemically removed by standard techniques.

A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from E. coli, including col E1, pCR1, pBR322, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941.

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

A wide variety of unicellular host cells are useful. These hosts may include well known eukaryotic and prokaryotic hosts, such as strains of E. coli, Pseudomonas, Bacillus, Streptomyces, fungi, yeast, insect cells such as Spodoptera frugiperda (SF9), animal cells such as CHO and mouse cells, African green monkey cells such as COS 1, COS 7, BSC 1, BSC 40, and BMT 10, and human cells, as well as plant cells in tissue culture. For animal cell expression, we prefer CHO cells and COS 7 cells.

It should, of course, be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the sequence, its controllability, and its compatibility with the DNA sequences discussed herein, particularly as regards potential secondary structures. Unicellular hosts should be selected by consideration of their compatibility with the chosen vector, the toxicity of the product coded for by the DNA sequences, their secretion characteristics, their ability to fold the soluble polypeptides correctly, their fermentation or culture requirements, and the ease of purification of the products coded for by the DNA sequences.

Within these parameters, one of skill in the art may select various vector/expression control sequence/host combinations that will express the desired DNA sequences on fermentation or in large scale animal culture, for example with CHO cells or COS 7 cells.

The soluble LFA-3 and CD2 polypeptides may be isolated from the fermentation or cell culture and purified using any of a variety of conventional methods. One of skill in the art may select the most appropriate isolation and purification techniques.

While recombinant DNA techniques are the preferred method of producing useful soluble CD2 polypeptides or soluble LFA-3 polypeptides having a sequence of more than 20 amino acids, shorter CD2 or LFA-3 polypeptides having less than about 20 amino acids are preferably produced by conventional chemical synthesis techniques. Synthetically produced polypeptides useful in this invention can advantageously be produced in extremely high yields and can be easily purified.

Preferably, such soluble CD2 polypeptides or soluble LFA-3 polypeptides are synthesized by solution phase or solid phase polypeptide synthesis and, optionally, digested with carboxypeptidase (to remove C-terminal amino acids) or degraded by manual Edman degradation (to remove N-terminal amino acids). Proper folding of the polypeptides may be achieved under oxidative conditions which favor disulfide bridge formation as described by Kent, "Chemical Synthesis of Polypeptides and Proteins", *Ann. Rev. Biochem.*, 57, pp. 957-89 (1988). Polypeptides produced in this way may then be purified by separation techniques widely known in the art, preferably utilizing reverse phase HPLC. The use of solution phase synthesis advantageously allows for the direct addition of certain derivatized amino acids to the growing polypeptide chain, such as the O-sulfate ester of tyrosine. This obviates the need for a subsequent derivatization step to modify any residue of the polypeptides useful in this invention.

C. LFA-3 And CD2 Mimetic Agents

Also useful in the methods of this invention are LFA-3 and CD2 mimetic agents. These agents which may be peptides, semi-peptidic compounds or non-peptidic compounds, are inhibitors of the CD2/LFA-3 interaction. The most preferred CD2 and LFA-3 mimetic agents will inhibit the CD2/LFA-3 interaction at least as well as anti-LFA-3 monoclonal antibody 7A6 or anti-CD2 monoclonal antibody TS2/18 (described supra).

Such mimetic agents may be produced by synthesizing a plurality of peptides (e.g., 5-20 amino acids in length), semi-peptidic compounds or non-peptidic, organic compounds, and then screening those compounds for their ability to inhibit the CD2/LFA-3 interaction. See generally U.S. Pat. No. 4,833,092, Scott and Smith, "Searching for Peptide Ligands with an Epitope Library", *Science*, 249, pp.

386-90 (1990), and Devlin et al., "Random Peptide Libraries: A Source of Specific Protein Binding Molecules", *Science*, 249, pp. 404-07 (1990), which are herein incorporated by reference.

D. Derivatized Inhibitors

Also useful in the methods of this invention are derivatized inhibitors of the CD2/LFA-3 interaction in which, for example, any of the antibody homologs, soluble CD2 and LFA-3 polypeptides, or CD2 and LFA-3 mimetic agents described herein are functionally linked (by chemical coupling, genetic fusion or otherwise) to one or more members independently selected from the group consisting of anti-LFA-3 and anti-CD2 antibody homologs, soluble LFA-3 and CD2 polypeptides, CD2 and LFA-3 mimetic agents, cytotoxic agents and pharmaceutical agents.

One type of derivatized inhibitor is produced by crosslinking two or more inhibitors (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another possibility for cross-linking takes advantage of the PI linkage signal sequence in PI-linked LFA-3, or fragments thereof. Specifically, DNA encoding the PI-linkage signal sequence (e.g., $AA_{162}$-$AA_{212}$ of SEQ ID NO:4) is ligated downstream of DNA encoding a desired polypeptide, preferably a soluble LFA-3 polypeptide. If this construct is expressed in an appropriate eukaryotic cell, the cell will recognize the PI linkage signal sequence and will covalently link PI to the polypeptide. The hydrophobic property of the PI may then be exploited to form micellar aggregates of the polypeptides.

Also useful are inhibitors linked to one or more cytotoxic or pharmaceutical agents. Useful pharmaceutical agents include biologically active peptides, polypeptides and proteins, such as antibody homologs specific for a human polypeptide other than CD2 or LFA-3, or portions thereof. Useful pharmaceutical agents and cytotoxic agents also include cyclosporin A, prednisone, FK506, methotrexate, steroids, retinoids, interferon, and nitrogen mustard.

Preferred inhibitors derivatized with a pharmaceutical agent include recombinantly-produced polypeptides in which a soluble LFA-3 polypeptide, soluble CD2 polypeptide, or a peptidyl CD2 or peptidyl LFA-3 mimetic agent is fused to all or part of an immunoglobulin heavy chain hinge region and all or part of a heavy chain constant region. Preferred polypeptides for preparing such fusion proteins are soluble LFA-3 polypeptides. Most preferred are fusion proteins containing $AA_1$-$AA_{92}$ of LFA-3 (e.g., SEQ ID NO:2) fused to a portion of a human $IgG_1$ hinge region (including the C-terminal ten amino acids of the hinge region containing two cysteine residues thought to participate in interchain disulfide bonding) and the $C_H2$ and $C_H3$ regions of an $IgG_1$ heavy chain constant domain. Such fusion proteins are expected to exhibit prolonged serum half-lives and enable inhibitor dimerization.

Pharmaceutical Compositions And Methods According To This Invention

This invention provides a method for preventing or treating the above-mentioned skin conditions in a mammal by administering to the mammal one or more inhibitors of the CD2/LFA-3 interaction, or derivatized form(s) thereof.

Preferably, an effective amount of the inhibitor or derivatized form thereof is administered. By "effective amount" is meant an amount capable of lessening the spread or severity of the skin conditions described herein.

It will be apparent to those of skill in the art that the effective amount of inhibitor will depend, inter alia, upon the administration schedule, the unit dose administered, whether the inhibitor is administered in combination with other therapeutic agents, the immune status and health of the patient, the therapeutic or prophylactic activity of the particular inhibitor administered and the serum half-life.

Preferably, the inhibitor is administered at a dose between about 0.001 and about 50 mg inhibitor per kg body weight, more preferably, between about 0.01 and about 10 mg inhibitor per kg body weight, most preferably between about 0.1 and about 4 mg inhibitor per kg body weight.

Unit doses should be administered until an effect is observed. The effect may be measured by a variety of methods, including, in vitro T cell activity assays and clearing of affected skin areas. Preferably, the unit dose is administered about one to three times per week or one to three times per day. More preferably, it is administered about one to three times per day for between about 3 and 7 days, or about one to three times per day for between about 3 and 7 days on a monthly basis. It will be recognized, however, that lower or higher dosages and other administrations schedules may be employed.

The inhibitor(s) or derivatized form(s) thereof are also preferably administered in a composition including a pharmaceutically acceptable carrier. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the inhibitor.

The pharmaceutical composition or inhibitor may be administered in conjunction with other therapeutic or prophylactic agents. These include, for example, cyclosporin A, steroids, retinoids, nitrogen mustard, interferon, methotrexate, antibiotics and antihistamines.

These agents may be administered in single dosage form with the inhibitor (i.e., as part of the same pharmaceutical composition), a multiple dosage form separately from the inhibitor, but concurrently, or a multiple dosage form wherein the two components are administered separately but sequentially. Alternatively, the inhibitor and the other active agent may be in the form of a single conjugated molecule. Conjugation of the two components may be achieved by standard cross-linking techniques well known in the art. A single molecule may also take the form of a recombinant fusion protein. In addition, the inhibitors, or pharmaceutical compositions, useful in the present invention may be used in combination with other therapies such as PUVA, chemotherapy and UV light. Such combination therapies may advantageously utilize lower dosages of the therapeutic or prophylactic agents.

The inhibitor, or pharmaceutical composition, may be in a variety of forms. These include, for example, solid, semi-solid and liquid dosage forms, such as tablets, pills, powders, liquid solutions, dispersions or suspensions, liposomes, suppositories, injectable infusible, and topical preparations. The preferred form depends on the intended mode of administration and therapeutic application. The preferred forms are injectable or infusible solutions.

The inhibitor or pharmaceutical composition may be administered intravenously, intramuscularly, subcutaneously, intra-articularly, intrathecally, periostally, intratumorally, intralesionally, perilesionally by infusion, orally, topically or by inhalation. Preferably it is administered subcutaneously, intramuscularly or intravenously. Most preferably, it is administered subcutaneously.

The invention includes formulations suitable for use as topically applied sunscreens or UV-protectants. Preferred embodiments include LFA3TIP preparations. The active ingredient can be formulated in a liposome. The product can be applied before, during, or after UV exposure, or before, during, or after the development of redness.

In order that this invention may be better understood, the following examples are set forth. These examples are for purposes of illustration only, and are not to be construed as limiting the scope of the invention in any manner.

EXAMPLES

Example 1

Subjects

Six adult patients participated in the investigation. Informed consent was obtained after Internal Review Board approval of the protocol. All patients satisfied the major diagnostic criteria for psoriasis, namely chronic papulosquamous plaques of characteristic morphology and distribution. The intermittent use of topical corticosteroids was common among these patients but was discontinued 2 weeks prior to entry into the study. A group of healthy volunteers with no history of psoriasis or other skin disease was utilized as the normal control group.

Preparation of Epidermal Cell Suspensions

Skin biopsy specimens were obtained from both normal and lesional skin by using a keratome. The specimens were submerged in Dulbecco's phosphate buffered saline ("PBS") (Gibco Labs, Grand Island, N.Y.) containing 50 units/ml dispase (Collaborative Research, Bedford, Mass.). The specimens were then incubated at 4° C. for 18 hours and the epidermis removed from the remaining dermis.

Epidermal sheets were removed from the dermis, submerged in Dulbecco's PBS containing 0.5% trypsin (Sigma Chemical Co., St. Louis, Mo.), and incubated at 37° C. for 30 minutes.

Trypsinized epidermal sheets were transferred to 0.05% DNase (Sigma) in Dulbecco's PBS where they were teased into a cell suspension. Fetal bovine serum ("FBS") (Hyclone, Logan, Utah) was added to inactivate residual trypsin and the epidermal cell suspension then passed through a 112 µm nylon filter (Tetko, Elmsford, N.Y.). After washing the predominantly single cell suspension three times in Dulbecco's PBS with 1% FBS, cells were resuspended in culture media which consisted of RPMI 1640 (Whittaker, Mass.; Bioproducts, Wakerfield, Md.) containing 1% penicillin and streptomycin, 1% glutamine (Gibco), and 10% human AB serum (Sigma).

Preparation of MNC and T cells

Peripheral blood mononuclear cells ("MNC") were isolated from heparinized blood using Ficoll-Hypaque® (Pharmacia) density gradient centrifugation according to manufacturer's suggested protocol. Resting CD4+ T cells were prepared as follows. Macrophages were removed by plastic adherence at 37° C. for 1 hour. The nonadherent, macrophage-depleted MNC were washed, and then depleted of $CD8^+$ T lymphocytes, activated T cells, B cells, antigen presenting cells and NK cells by incubation with monoclonal antibodies to CD8 (ATCC CRL 8014), HLA-DR (ATCC CRL H355), and CD11b (ATCC CRL 8026). These antibodies were used as dilutions in PBS (1:200) of ascites fluid from pristane-primed mice.

The antibody treated MNC were incubated at 4° C. with 4.5 nm magnetic particles coated with goat anti-mouse IgG (Dynabeads® M-450, Dynal, Oslo, Norway) at a ratio of 3 beads per cell. Antigen positive cells were depleted by being drawn by a magnet (Advanced Magnetics, Cambridge, Mass.) against the side of the tube allowing the remaining cells in suspension to be decanted. The decanted cell suspension was again exposed to a magnet and cells remaining in suspension collected. Fresh goat anti-mouse IgG beads were again added to the collected cells in suspension in order to deplete any remaining antigen positive cells, and the magnetic removal process repeated. Cells were washed in PBS and resuspended in culture media prior to use. This treatment results in a preparation of resting $CD4^+$ T lymphocytes enriched to 99% purity and devoid of intrinsic antigen presenting activity.

Proliferative Response of T Lymphocytes to Autologous Psoriatic Cells

One hundred thousand $CD4^+$ T lymphocytes were added to round bottom microtiter wells (Costar, Cambridge, Mass.) with eighty thousand psoriatic epidermal cells in 0.2 ml of RPMI containing 10% human AB serum (Sigma, St. Louis, Mo.). This number of psoriatic epidermal cells per well was chosen because previous experiments demonstrated that this number is sufficient to induce autoreactive T cell responses. After incubation at 37° C. in 5% $CO_2$/95% air for 6 days, 1 µCi of [$^3$H]TdR (ICN Radiochemicals, Irvine, Calif.) was added per well and the cells harvested 18 hours later on a PHD cell harvester (Cambridge Technology Inc., Cambridge, Mass.). The [$^3$H]TdR incorporation was measured on a Packard scintillation counter (Packard Instrument Co., Downers Grover, Ill.). [$^3$H]TdR incorporation is a measure of T cell proliferation.

Appropriate controls for T cells ("TC") alone or epidermal cells ("EC") alone were carried out using the above protocol. No [$^3$H]TdR incorporation was observed in these assays (data not shown). Brisk proliferation of autologous T cells in response to psoriatic skin cells was observed (data not shown).

In addition, to test the allogeneic response to normal skin, the above protocol was carried out using one hundred thousand allogeneic T cells and eighty thousand normal skin cells. Under these conditions, a brisk proliferation of allogeneic T cells was observed (data not shown).

Blocking of Psoriatic Epidermal Cells' Ability To Stimulate Autologous T Lymphocyte Proliferation The effect on [$^3$H]TdR incorporation (i.e., T cell proliferation) of an anti-CD2 monoclonal antibody (TS2/18) (Sanchez-Madrid et al., "Three Distinct Antigens Associated with Human T-lymphocyte-mediated Cytolysis: LFA-1, LFA-2, and LFA-3", *Proc. Natl. Acad. Sci. USA*, 79, pp. 7489-93 (1982)), an anti-LFA-3 monoclonal antibody (7A6) (ATCC HB 10695), or an isotype-matched, control monoclonal antibody of irrelevant specificity (MOPC21, Sigma Chemical Co., St. Louis, Mo.) was measured using the protocol outlined above in the presence of 50 µg/ml of the respective antibodies.

FIG. 1 demonstrates that addition of anti-CD2 or anti-LFA-3 resulted in a consistent (n=4) and substantial (approximately 60%) inhibition of autologous T cell proliferation in response to lesional psoriatic epidermis, as compared to proliferation in the presence of the isotype-matched control antibody.

FIG. 1 displays data for four patients only. These four patients demonstrated autoreactivity of blood CD4+ T cells to their own lesional epidermis, despite the fact that no antigen was added to the system. This is an abnormal finding; normal individuals' cocultures of autologous blood T cells and epidermal cells do not react. Such a reaction is considered to be an in vitro model of autoimmune reactions occurring in the skin. EC preparations from two additional patients were not informative. One EC preparation was bacterially contaminated; the other contained antigen presenting cells that did not induce autoreactive T cell responses.

Addition of 50 μg per ml of the anti-CD2 or anti-LFA-3 antibodies to the allogeneic normal skin assay described above also resulted in an inhibition of allogeneic T cell activation. The degree of inhibition was not as substantial (approximately 40%) as that observed for autologous antigen presenting cell activity when using lesional psoriatic epidermis (data not shown).

Addition of the isotype-matched control antibody (specific for an irrelevant antigen) did not significantly alter the level of T cell proliferation of autologous T cells induced by lesional psoriatic epidermis (data not shown).

Example 2

Subject

One adult subject participated in this investigation. Informed consent was obtained after Internal Review Board approval of the protocol. The minimal dose of UV B from a bank of fluorescent bulbs (FS 40) required to induce skin erythema in the subject was determined prior to the study. A moderate sunburn (4 minimal erythemal doses) was then administered to the left buttock, which 3 days later was the source of UV damaged skin. Skin from the right buttock, which was unburned, was utilized for the control.

Preparation of Epidermal Cell Suspensions

Skin biopsy specimens were obtained from both normal and sunburned skin by using a keratome. Epidermal cell suspensions were prepared from these specimens using substantially the same protocol as in Example 1.

Isolation and Depletion of T cells

Peripheral blood mononuclear cells ("MNC") were isolated from heparinized blood of another person, using Ficoll-Hypaque® (Pharmacia) density gradient centrifugation according to manufacturer's suggested protocol. CD4+ T lymphocytes were then prepared substantially as outlined in Example 1.

Proliferative Response Of T Lymphocytes To Allogeneic UV Damaged Epidermal Cells One hundred thousand CD4+ T lymphocytes from another individual were added to round bottom microtiter wells (Costar, Cambridge, Mass.) with UV damaged epidermal cells from the subject, incubated in the presence of [$^3$H]TdR, harvested and [$^3$H]TdR incorporation was measured substantially as outlined in Example 1. This example differs from Example 1 in that the antigenic stimulus is alloantigen, rather than autoantigens that are stimulatory in psoriasis. Thus, allogeneic T cells were used, rather than autologous T cells.

Figure 2:
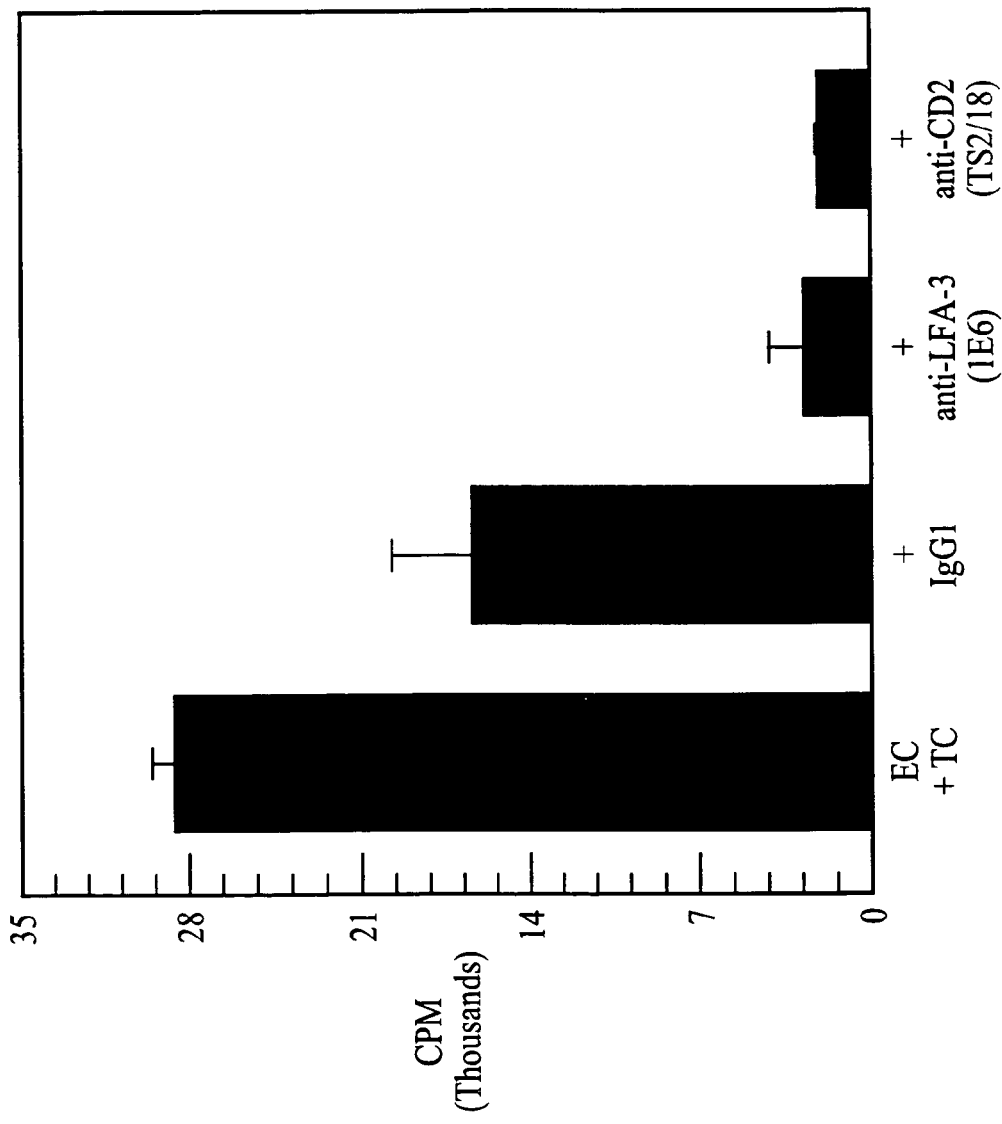
FIG. 2 illustrates the inhibition of allogeneic T cell activation by UV damaged epidermal cells ([$^3$H]TdR incorporation) caused by an anti-LFA-3 monoclonal antibody (1E6) or an anti-CD2 monoclonal antibody (TS2/18) as compared to a non-specific IgG antibody (MOPC21).

FIG. 2 shows a brisk proliferation of allogeneic T cells (as measured by [$^3$H]TdR incorporation) when incubated with UV damaged epidermal cells ("EC+TC").

Blocking Of UV Damaged Epidermal Cells' Ability To Stimulate Allogeneic T Lymphocyte Proliferation The effect on [$^3$H]TdR incorporation (i.e., T cell proliferation) of an anti-LFA-3 monoclonal antibody (1E6) (ATCC HB 10693), an anti-CD2 monoclonal antibody (TS2/18) (Sanchez-Madrid et al., "Three Distinct Antigens Associated With Human T-lymphocyte-Mediated Cytolysis: LFA-1, LFA-2, and LFA-3", Proc. Natl. Acad. Sci. USA, 79, pp. 7489-93 (1982)), and an isotype-matched, control monoclonal antibody of irrelevant specificity (MOPC21, Sigma Chemical Co.), was measured using the protocol outlined above in the presence of 50 μg/ml of the respective antibodies.

FIG. 2 shows that in the presence of a monoclonal antibody of irrelevant specificity (MOPC21, Sigma Chemical Co.), [$^3$H]TdR incorporation was somewhat reduced. However, the addition of anti-LFA-3 monoclonal antibody 1E6 or anti-CD2 monoclonal antibody TS2/18 resulted in a substantial inhibition of T cell proliferation compared to proliferation in the presence of the control antibody.

Example 3

Preparation of LFA3TIP

LFA3TIP, a fusion protein comprised of the first extracellular domain of LFA-3 fused to the hinge, $C_H2$ and $C_H3$ regions of human IgG1 was constructed as described in Miller, G T et al. (1993) J. Exp. Med. 178:211, hereby incorporated by reference. LFA3TIP was purified from culture medium of transfectant CHO (chinese hamster ovary) cell lines by absorption to Protein-A Sepharose 4B® (Pharmacia) and eluted with 50 mM glycine, 250 mM NaCl (pH 3.0). Fractions containing protein were pooled and subjected to gel filtration on Superose-6™ (Pharmacia) in phosphate buffered saline (PBS). Peak fractions were pooled and analyzed for purity on 12% reducing and non-reducing SDS-PAGE.

Figure 3:
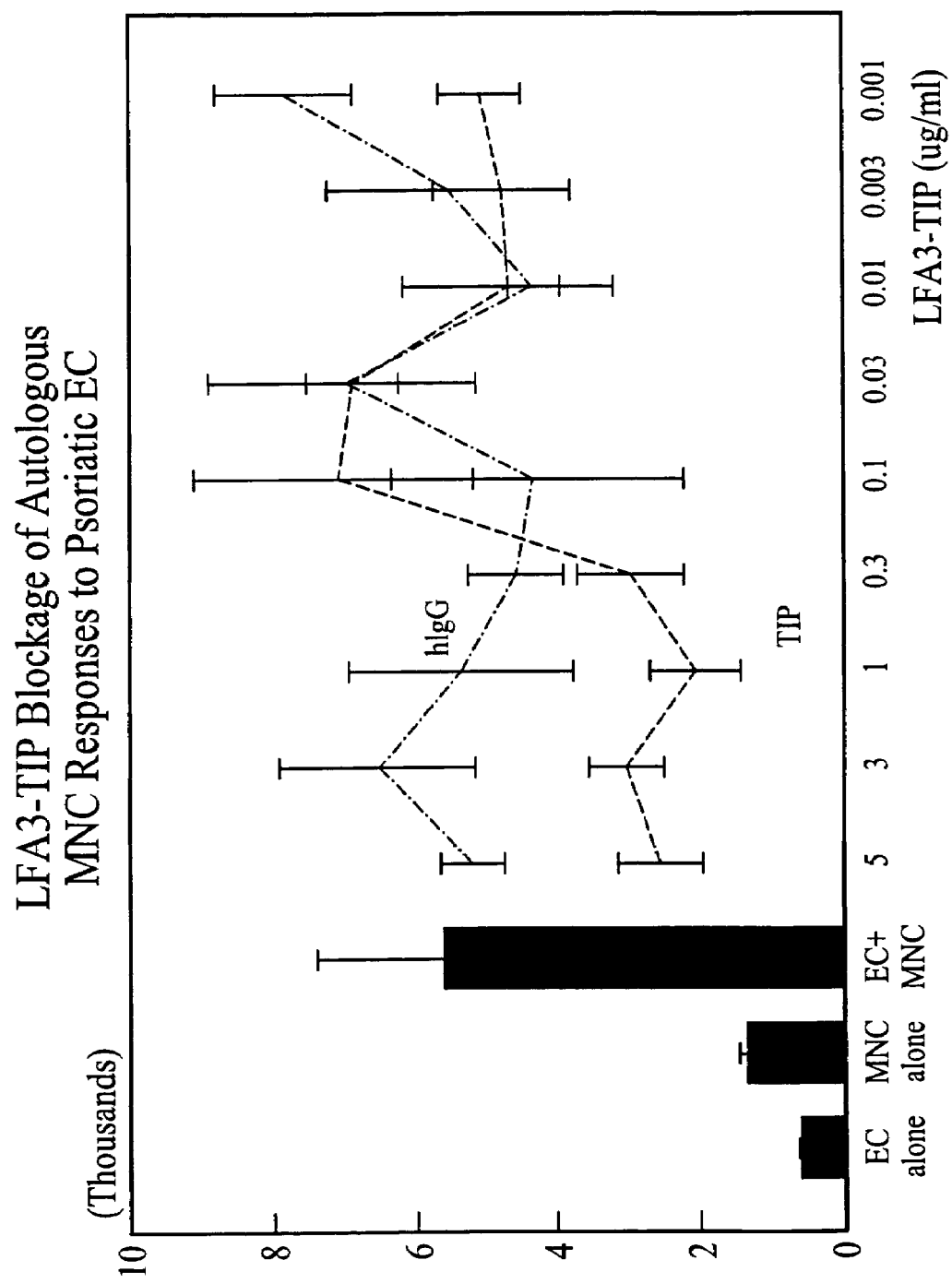
FIG. 3 illustrates the inhibition of autologous mononuclear cell responses to psoriatic epidermal cells ([$^3$H]TdR incorporation) caused by an LFA3TIP fusion molecule as compared to a human IgG control.

1. LFA3TIP Results in a Decrease of the Proliferative Response of Autologous Mononuclear Cells to Lesional Psoriatic Epidermal Cells The ability of LFA3TIP to inhibit the response of autologous mononuclear cells (MNC) to lesional psoriatic epidermal cells (EC) in suspension was determined. Epidermal cell suspensions were prepared essentially in the same way as in Example 1 above. Proliferation of MNC was measured by thymidine incorporation. As shown in FIG. 3 there was minimal proliferation with epidermal cells alone. Combination of EC with MNC resulted in a relatively strong response, approaching 6000 cpm. In contrast to the human IgG controls, addition of LFA3TIP, at concentrations between 5 and 0.3 μg/ml, resulted in a consistent inhibition of the autoreactive response. If the counts of EC and MNC alone are taken into account, the LFA3TIP inhibition is quite substantial.

The mechanism of the IgG1 enhancement of EC-induced MNC proliferation is unknown. It is clear however, from the experiment described above, using autologous MNC and lesional epidermal cells of psoriasis, that LFA3TIP results in very substantial inhibition.

2. Spontaneous Proliferation of Lesional Psoriatic Dermal Cells

Figure 4:
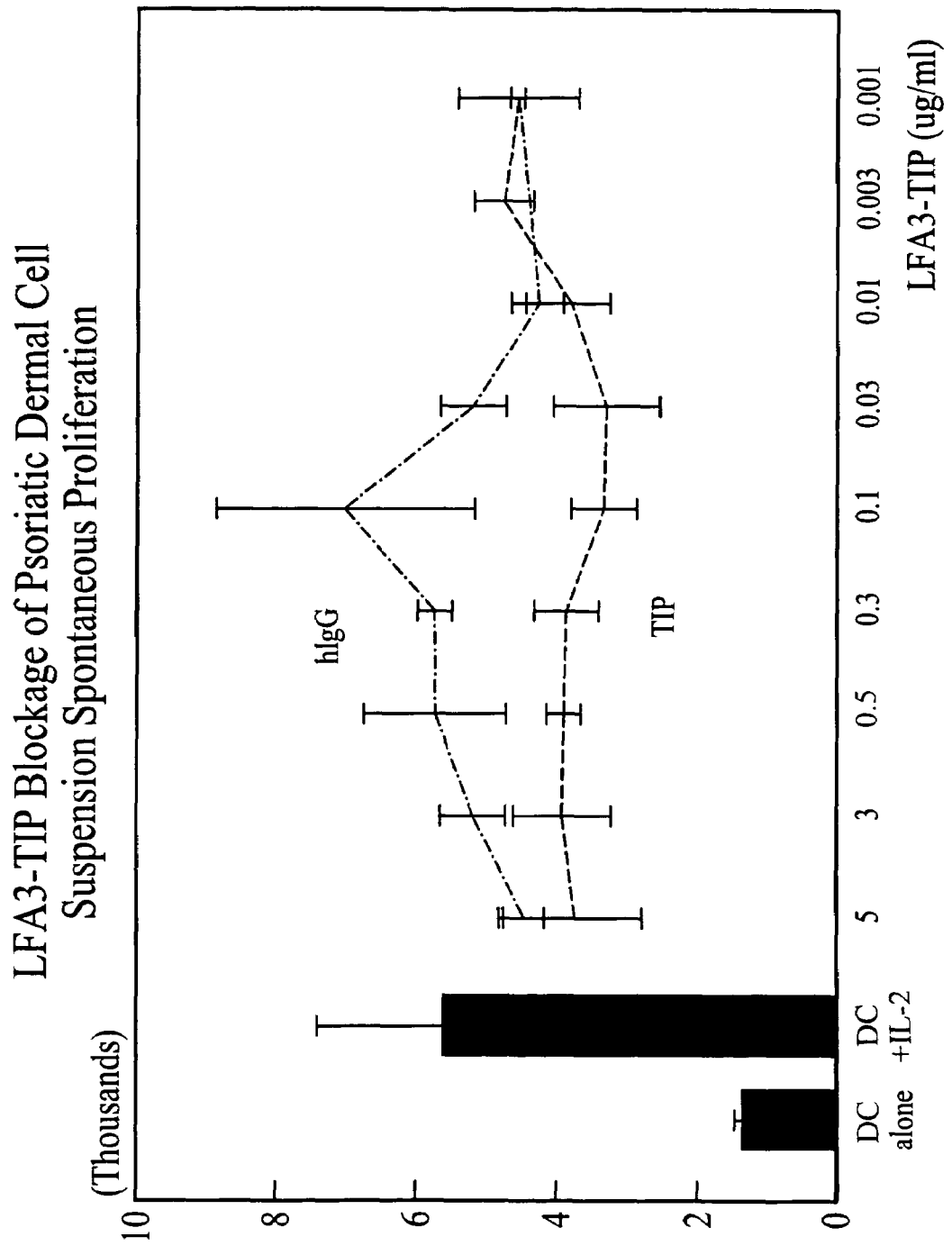
FIG. 4 illustrates the effect of LFA3TIP on spontaneous lesional psoriatic dermal cell proliferation. A reduction in spontaneous dermal cell proliferation ([$^3$H]TdR incorporation) was seen with dose responses between 0.03 and 0.003 µg/ml of LFA3TIP. LFA3TIP cultures are consistently less proliferative than the human IgG control cultures through the concentration of 0.01 µg/ml.

FIG. 4 shows the effect of LFA3TIP on spontaneous lesional psoriatic dermal cell proliferation. Suspensions of psoriatic dermis were prepared by dispase splitting of the epidermis from the dermis, followed by digestion of the dermis with collagenase, hyalurinidase, and DNase, and filtering through sequential nylon mesh sizing filters. Psoriatic dermis, upon digestion into a single cell suspension, undergoes an increased level of spontaneous proliferation relative to dermal cells in suspensions from normal subjects. The increased proliferation is accompanied by the formation of clusters, which occurs in psoriatic and not in normal cultures. The proliferation can only partly be accounted for by T cell proliferation. There appears additionally to be heterotypic or homotypic adhesion between the dermal cells, some of which may be macrophages and some of which may be stromal cells. To determine if LFA3TIP could block at least the T cell component of the spontaneous proliferation, lesional dermal cells were plated in suspension. Approximately 2000 cpm was observed with dermal cells alone (normal controls generally exhibit between 200 and 1500 cpm). A limiting dose of IL-2 was then added at a concentration that should activate only T cells expressing the high affinity IL-2 receptor (10 units/ml on a daily basis ×4 days). This boosted the counts to 4600 cpm (dermal cells plus IL-2). Varying dilutions of LFA3TIP or human IgG were than added. A reduction in spontaneous dermal cell proliferation was seen with dose responses between 0.03 and 0.003 µg/ml. Furthermore, the LFA3TIP cultures are consistently less proliferative than the human IgG control cultures through the concentration of 0.01 µg/ml. These results provide an interesting and important evidence of LFA3TIP activity on immunologic mechanisms occurring in fresh ex vivo psoriatic tissue.

Figure 5:
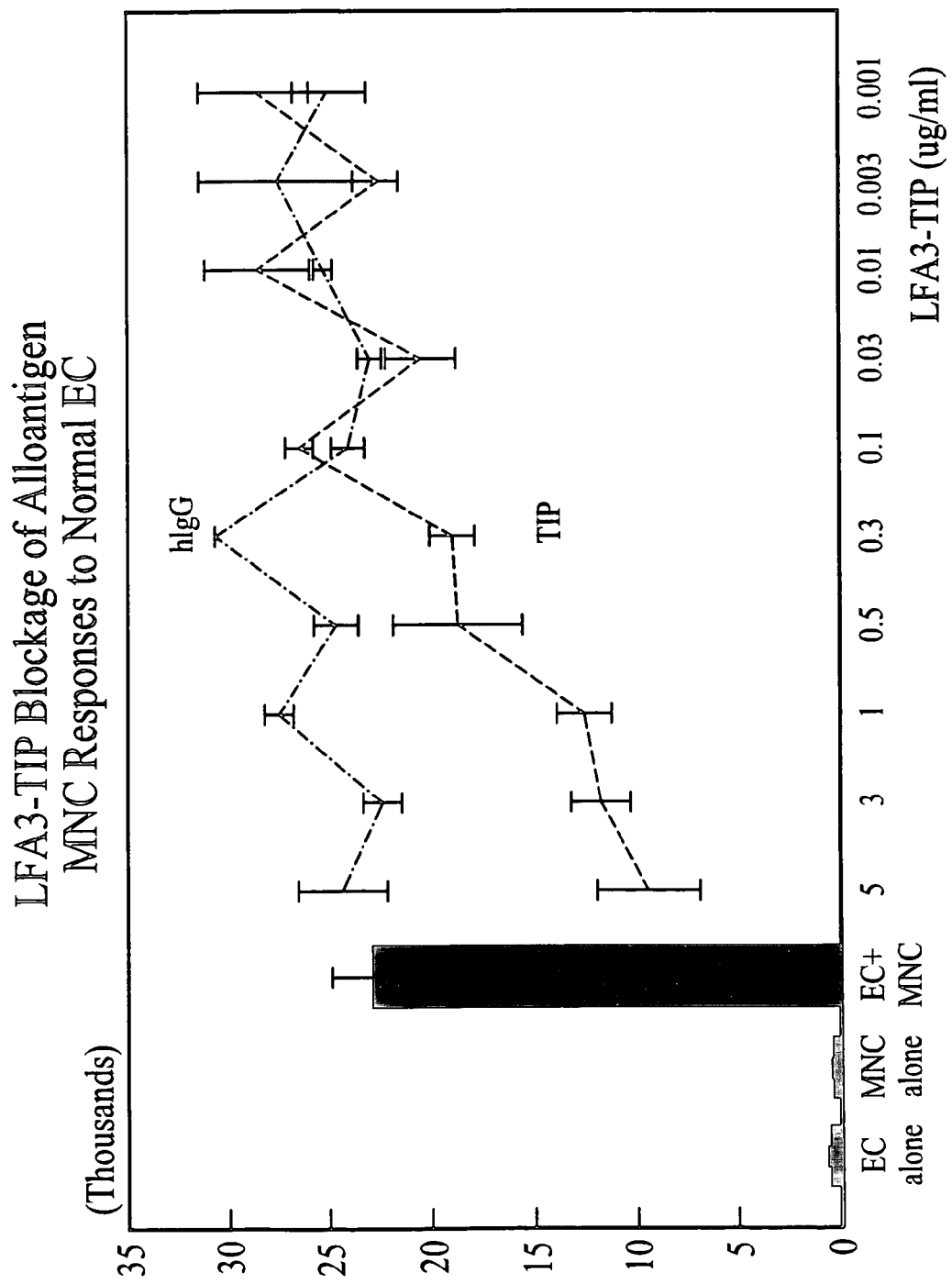
FIG. 5 illustrates the inhibition of allogeneic mononuclear cell responses to normal epidermal cells ([$^3$H]TdR incorporation) caused by an LFA3TIP fusion molecule as compared to a human IgG control.

3. Proliferative Response of Allogeneic Mononuclear Cells to Normal Epidermal Cells This experiment shows the ability of LFA3TIP to inhibit proliferation of allogeneic mononuclear cells to normal epidermal cells. Normal epidermal cells were prepared essentially as described for Example 1. MNC were prepared essentially as described for Example 1. As shown in FIG. 5, epidermal cells (EC) plus MNC demonstrated levels of proliferation of approximately 22,000 cpm. Human IgG appears to be slightly enhancing between 12 and 0.3 µg/ml of LFA3TIP, relative to EC plus MNC alone. However, LFA3TIP between 5 and 0.1 µg/ml, exerted a clear dose-responsive inhibition. Inhibition of Langerhans cell dependent T cell activation models the type of activation that occurs in allergic contact dermatitis, atopic dermatitis and mycosis fungoides type of cutaneous T cell lymphoma.

Figure 6:
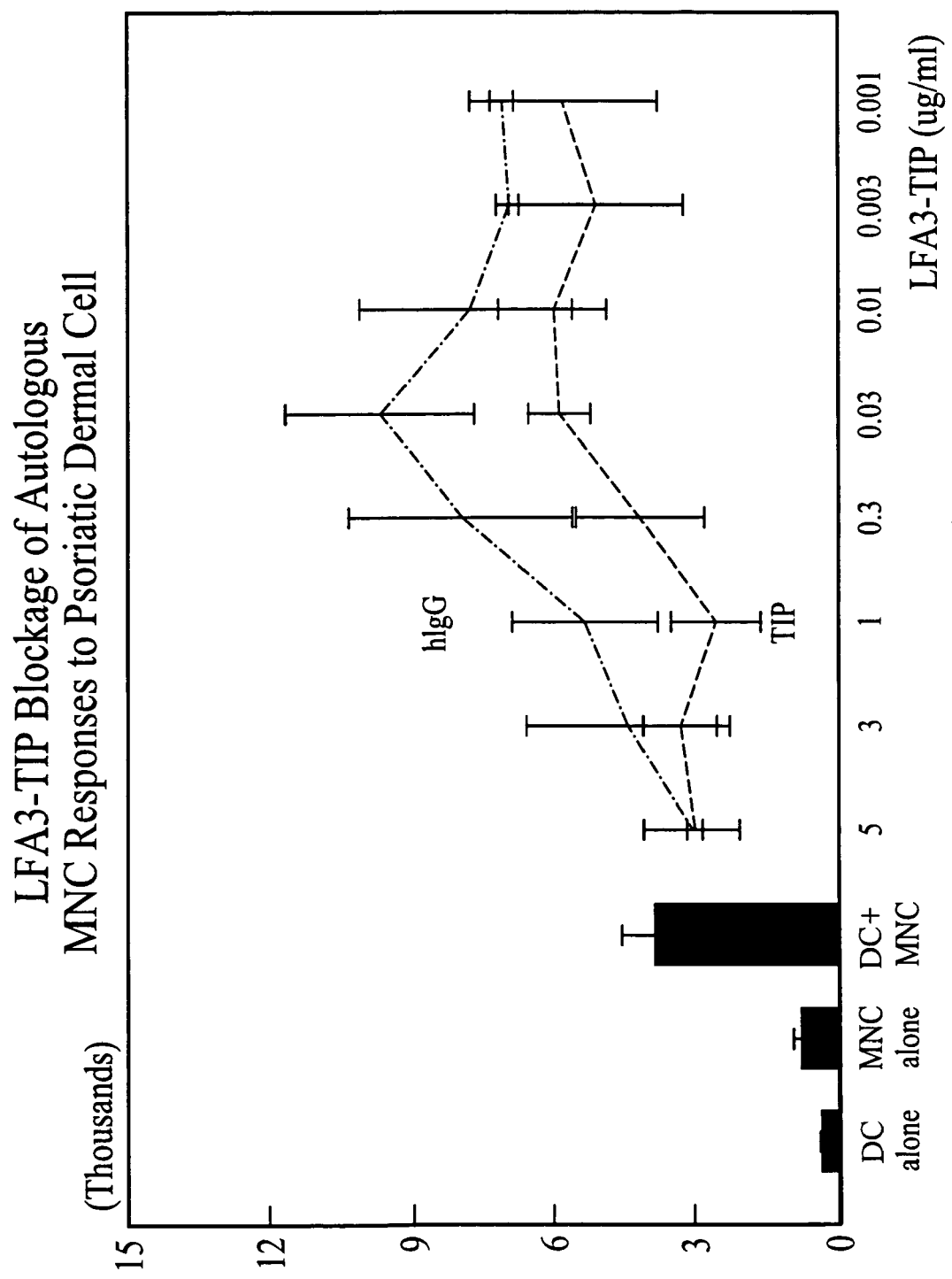
FIG. 6 illustrates the inhibition of autologous mononuclear cell responses to psoriatic dermal cells ([$^3$H]TdR incorporation) caused by an LFA3TIP fusion molecule as compared to a human IgG control.

4. Proliferative Response of Autologous Mononuclear Cells to Lesional Psoriatic Dermal Cells FIG. 6 demonstrates the response of autologous MNC to lesional dermal cells prepared as a single cell suspension. Following dispase splitting of the epidermis from the dermis, the dermis is digested by collagenase, hyaluronidase, and DNase, and filtered through sequential nylon mesh sizing filters. In this patient, the spontaneous level of dermal cell proliferation was low, and induction of a dermal cell plus mononuclear cell reaction could be observed. This is a fairly complex system because the dermal cell preparation has a number of cell types, including macrophages, some neutrophils, antigen presenting cells, filbroblasts, mast cells, and endothelial cells, as well as T lymphocytes. However, it is probably a reasonable approximation of the in vivo milieu as the infiltrating mononuclear cells first enter into perivascular interstitium of the dermis in response to chemoattractive signals present in psoriasis. Enhancement of the dermal cell-induced proliferation occurred between 0.3 and 0.01 µg/ml of human IgG control. LFA3TIP inhibited this enhancement, and resulted in a reduced proliferative response between 1 and 0.03 µg/ml. In this dermal cell assay, the addition of IgG or removal of Fc IgG receptor bearing cells, specifically cells bearing the macrophage and neutrophil integrin CD11b, results in elevated spontaneous proliferation of dermal fibroblasts. To what degree the LFA3TIP inhibitory effect is upon T cell proliferation as opposed to complex FcγRIII-mediated macrophage antiproliferative effects on other cell types is not possible to determine. Regardless, the data clearly support a trend in both this and the previous dermal cell proliferation assays from psoriatic lesional skin which is in the therapeutically beneficial direction for use of LFA3TIP.

Figure 7A:
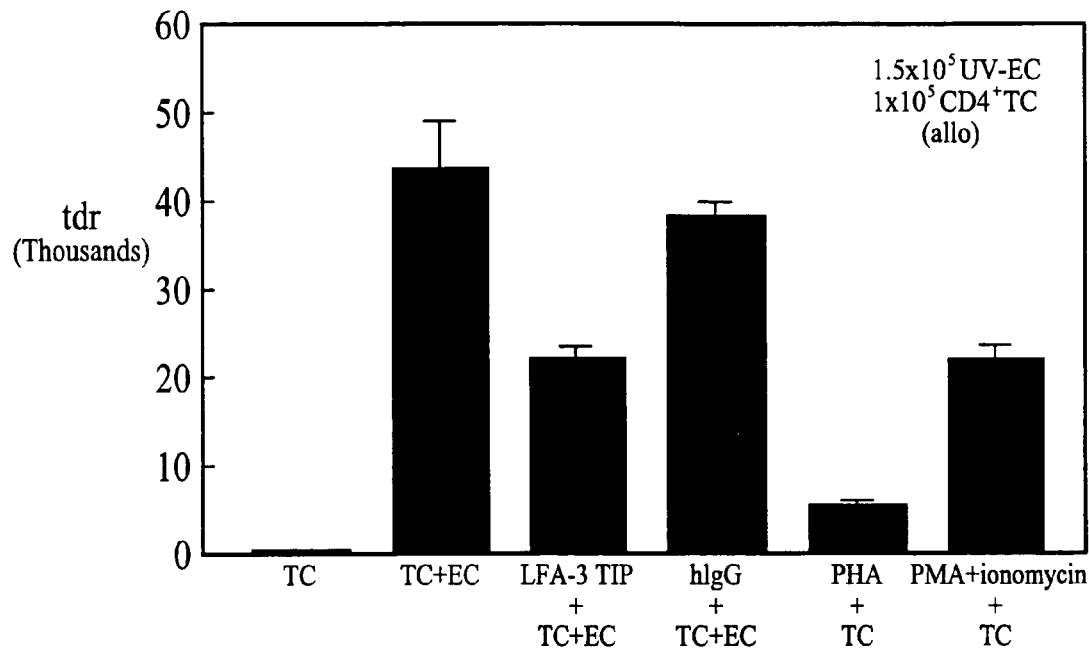
FIG. 7 illustrates the inhibition of inflammatory macrophage APC activity in UV-exposed epidermal cells (EC) ([$^3$H]TdR incorporation) caused by an LFA3TIP fusion molecule as compared to a human IgG control. Two concentrations of UV-EC are shown in panel 7A and 7B. LFA3TIP incubation resulted in approximately 50% inhibition.
Figure 7B:
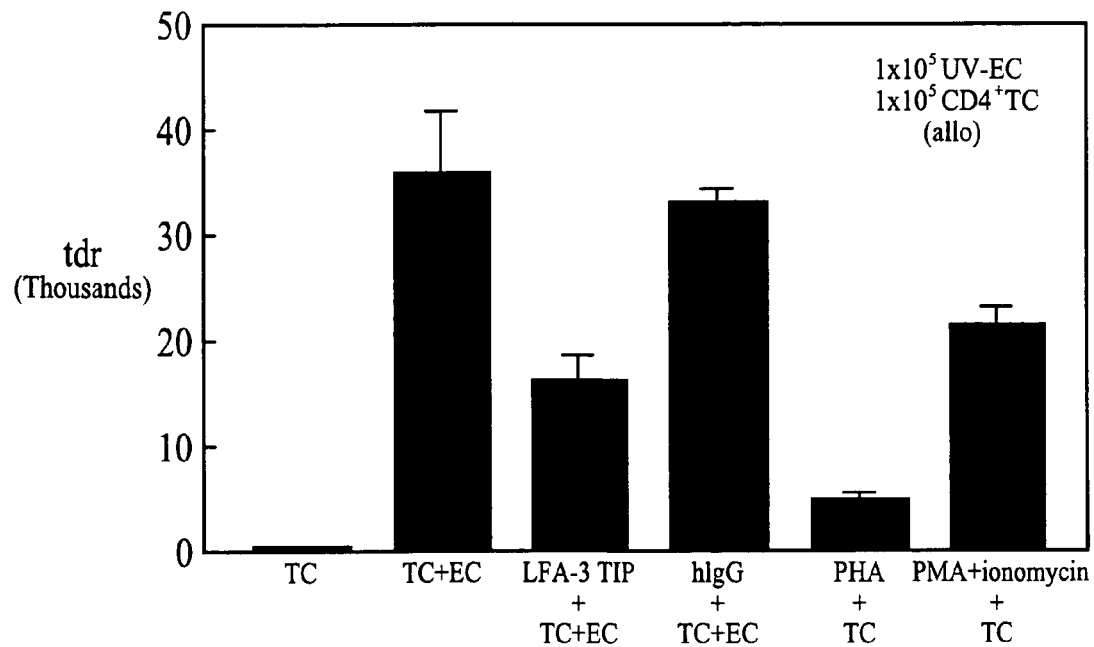

5. Proliferative Response of Allogeneic T lymphocytes to UV Damaged Epidermal Cells Human subjects were exposed to 4 minimal erythemal doses of ultraviolet radiation, and 3 days later the epidermis was removed and prepared into an epidermal cell suspension. Suspensions were combined with resting, negatively selected CD4+ T lymphocytes which were allogeneic to the sunburned donor. Two concentrations of UV-EC are shown in FIGS. 7A and B. Relative to T cells plus epidermal cells alone, or T cells plus epidermal cells incubated with identical concentrations of IgG, LFA3TIP incubation resulted in approximately 50% inhibition. The cells were moderately free of antigen presenting cells (APC's), as evidenced by relatively minimal PHA proliferation, but were capable of responding as evidenced by responsiveness to PMA plus ionomycin. These data demonstrate that inflammatory UV macrophages which migrate into sunburned skin use an LFA3TIP dependent mechanism to induce T cell activation. Blockade of this process should be relevant to photoaging, in that repeated inflammatory activation in the skin is likely responsible for collagenase and elastase activation via lymphokine activation. In addition, blockade of this signaling may reduce the generation of T suppressor cells which these UV induced macrophages generate. These suppressor cells are the one responsible for tolerance in a contact sensitivity mode of UV-induced immunologic host susceptibility to UV carcinogenesis.

DEPOSITS

Murine hybridoma cells and anti-LFA-3 antibodies useful in the present invention are exemplified by cultures deposited under the Budapest Treaty with American Type Culture Collection, 10801 University Boulevard, Manassas, Va. 20110-2209, on Mar. 5, 1991, and identified as:

| Designation | ATCC Accession No. |
| --- | --- |
| 1E6 | HB 10693 |
| HC-1B11 | HB 10694 |
| 7A6 | HB 10695 |
| 8B8 | HB 10696 |

A bacteriophage carrying a plasmid encoding transmembrane LFA-3 was deposited under the Budapest Treaty with In Vitro International, Inc., Linthicum, Md., U.S.A., on May 28, 1987 under Accession No. IVI-10133. This deposit was transferred to American Type Culture Collection on Jun. 20, 1991 and identified as:

| Designation | ATCC Accession No. |
|---|---|
| λHT16[λgt10/LFA-3] | 75107 |

E. *coli* transformed with a plasmid encoding PI-linked LFA-3 was deposited under the Budapest Treaty with In Vitro International, Inc. on Jul. 22, 1988 under Accession No. IVI-10180. This deposit was transferred to American Type Culture Collection on Jun. 20, 1991 and identified as:

| Designation | ATCC Accession No. |
|---|---|
| p24 | 68788 |

SEQUENCES

The following is a summary of the sequences set forth in the Sequence Listing:

SEQ ID NO:1 DNA sequence of transmembrane LFA-3

SEQ ID NO:2 Amino acid sequence of transmembrane LFA-3

SEQ ID NO:3 DNA sequence of PI-linked LFA-3

SEQ ID NO:4 Amino acid sequence of PI-linked LFA-3

SEQ ID NO:5 DNA sequence of CD2

SEQ ID NO:6 Amino acid sequence of CD2

SEQ ID NO:7 DNA sequence of LFA3TIP

SEQ ID NO:8 Amino acid sequence of LFA3TIP

While we have hereinbefore described a number of embodiments of this invention, it is apparent that our basic embodiments can be altered to provide other embodiments that utilize the processes of this invention. Therefore, it will be appreciated that the scope of this invention includes all alternative embodiments and variations which are defined in the foregoing specification and by the claims appended hereto; and the invention is not to be limited by the specific embodiments that have been presented herein by way of example.

We claim:

1. A method of preventing or treating skin conditions characterized by increased T cell activation and abnormal antigen presentation in the dermis and epidermis, comprising the step of administering to a mammal a first agent that binds to LFA-3 or CD2 selected from the group consisting of an LFA-3 polypeptide, a CD2 polypeptide, an anti-CD2 antibody homolog, and an anti-LFA-3 antibody homolog, in combination with a therapeutic or prophylactic second agent, wherein the second agent is selected from the group consisting of: cyclosporin A, prednisone, FK506, methotrexate, steroids, retinoids, and nitrogen mustard.

2. The method of claim 1, wherein the first agent is a soluble LFA-3 polypeptide or an immunoglobulin (Ig) fusion thereof.

3. The method of claim 1, wherein the first agent comprises a soluble LFA-3 polypeptide fused to all or part of an immunoglobulin heavy chain hinge region and all or part of a heavy chain constant region.

4. The method of claim 1, wherein the first agent comprises a fusion protein comprising the amino terminal 92 amino acids of mature LFA-3, the C-terminal 10 amino acids of a human IgG1 hinge region and the CH2 and CH3 regions of a human IgG1 heavy chain constant domain.

5. The method of claim 1, wherein the first agent is LFA3TIP (amino acids 1-319 of SEQ ID NO:8).

6. The method of claim 1, wherein the first agent is encoded by an insert contained in plasmid pSAB152, deposited with American Type Culture Collection under the accession number ATCC 68720.

7. The method of claim 1, wherein the condition is psoriasis.

8. The method of claim 2, wherein the condition is psoriasis.

9. The method of claim 3, wherein the condition is psoriasis.

10. The method of claim 4, wherein the condition is psoriasis.

11. The method of claim 5, wherein the condition is psoriasis.

12. The method of claim 6, wherein the condition is psoriasis.

13. The method of claim 1, wherein the condition is elected from the group consisting of atopic dermatitis, cutaneous T cell lymphoma, mycosis fungoides, allergic and irritant contact dermatitis, lichen planus, alopecia areata, pyoderma gangrenosum, vitiligo, ocular cicatricial pemphigoid, and urticaria.

14. The method of claim 2, wherein the condition is elected from the group consisting of atopic dermatitis, cutaneous T cell lymphoma, mycosis fungoides, allergic and irritant contact dermatitis, lichen planus, alopecia areata, pyoderma gangrenosum, vitiligo, ocular cicatricial pemphigoid, and urticaria.

15. The method of claim 3, wherein the condition is elected from the group consisting of atopic dermatitis, cutaneous T cell lymphoma, mycosis fungoides, allergic and irritant contact dermatitis, lichen planus, alopecia areata, pyoderma gangrenosum, vitiligo, ocular cicatricial pemphigoid, and urticaria.

16. The method of claim 4, wherein the condition is elected from the group consisting of atopic dermatitis, cutaneous T cell lymphoma, mycosis fungoides, allergic and irritant contact dermatitis, lichen planus, alopecia areata, pyoderma gangrenosum, vitiligo, ocular cicatricial pemphigoid, and urticaria.

17. The method of claim 5, wherein the condition is elected from the group consisting of atopic dermatitis, cutaneous T cell lymphoma, mycosis fungoides, allergic and irritant contact dermatitis, lichen planus, alopecia areata, pyoderma gangrenosum, vitiligo, ocular cicatricial pemphigoid, and urticaria.

18. The method of claim 6, wherein the condition is elected from the group consisting of atopic dermatitis, cutaneous T cell lymphoma, mycosis fungoides, allergic and irritant contact dermatitis, lichen planus, alopecia areata, pyoderma gangrenosum, vitiligo, ocular cicatricial pemphigoid, and urticaria.

19. The method according to claim 1, wherein the first and second agent are administered concurrently.

20. The method according to claim 2, wherein the first and second agent are administered concurrently.

21. The method according to claim 3, wherein the first and second agent are administered concurrently.

22. The method according to claim 4, wherein the first and second agent are administered concurrently.

23. The method according to claim 5, wherein the first and second agent are administered concurrently.

24. The method according to claim 6, wherein the first and second agent are administered concurrently.

25. The method according to claim 1, wherein the first and second agent are administered sequentially.

26. The method according to claim 2, wherein the first and second agent are administered sequentially.

27. The method according to claim 3, wherein the first and second agent are administered sequentially.

28. The method according to claim 4, wherein the first and second agent are administered sequentially.

29. The method according to claim 5, wherein the first and second agent are administered sequentially.

30. The method according to claim 6, wherein the first and second agent are administered sequentially.

31. The method of claim 1, wherein the mammal is a human.

32. The method of claim 2, wherein the mammal is a human.

33. The method of claim 4, wherein the mammal is a human.

34. The method of claim 5, wherein the mammal is a human.

35. The method of claim 1, wherein the first agent is administered at a dose between about 0.001 and about 50 mg agent per kg body weight.

36. The method of claim 2, wherein the first agent is administered at a dose between about 0.001 and about 50 mg agent per kg body weight.

37. The method of claim 4, wherein the first agent is administered at a dose between about 0.001 and about 50 mg agent per kg body weight.

38. The method of claim 5, wherein the first agent is administered at a dose between about 0.001 and about 50 mg agent per kg body weight.

39. The method of claim 1, wherein the first agent is administered at a dose between about 0.01 and about 10 mg agent per kg body weight.

40. The method of claim 2, wherein the first agent is administered at a dose between about 0.01 and about 10 mg agent per kg body weight.

41. The method of claim 4, wherein the first agent is administered at a dose between about 0.01 and about 10 mg agent per kg body weight.

42. The method of claim 5, wherein the first agent is administered at a dose between about 0.01 and about 10 mg agent per kg body weight.

43. The method of claim 1, wherein the first agent is administered at a dose between about 0.1 and about 4 mg per kg body weight.

44. The method of claim 2, wherein the first agent is administered at a dose between about 0.1 and about 4 mg per kg body weight.

45. The method of claim 4, wherein the first agent is administered at a dose between about 0.1 and about 4 mg per kg body weight.

46. The method of claim 5, wherein the first agent is administered at a dose between about 0.1 and about 4 mg per kg body weight.

47. The method of claim 1, wherein the first agent is administered intramuscularly, intravenously or subcutaneously.

48. The method of claim 2, wherein the first agent is administered intramuscularly, intravenously or subcutaneously.

49. The method of claim 4, wherein the first agent is administered intramuscularly, intravenously or subcutaneously.

50. The method of claim 5, wherein the first agent is administered intramuscularly, intravenously or subcutaneously.

51. The method according to claim 1, wherein the first agent is an anti-CD2 or anti-LFA-3 antibody homolog.

52. The method of claim 51, wherein the antibody homolog is a humanized or chimeric antibody homolog.

53. The method of claim 51, wherein the first agent is a monoclonal anti-LFA-3 antibody produced by a hybridoma selected from the group consisting of hybridomas having Accession Nos. ATCC HB 10693 (1E6), ATCC HB 10694 (HC-1B11), ATCC HB 10695 (7A6), and ATCC HB 10696 (8B8).

54. The method of claim 51, wherein the first agent is selected from the group consisting of an Fab fragment, an Fab' fragment, an F(ab') 2 fragment, an F(v) fragment and an intact immunoglobulin heavy chain of an anti-LFA-3 antibody homolog.

55. The method of claim 51, wherein the first agent is selected from the group consisting of an Fab fragment, an Fab' fragment, an F(ab') 2 fragment, an F(v) fragment and an intact immunoglobulin heavy chain of an anti-CD2 antibody homolog.

56. The method of claim 1, wherein the first agent is a soluble CD2 polypeptide.

57. The method of claim 1, wherein the second agent is cyclosporine A.

58. The method of claim 2, wherein the second agent is cyclosporine A.

59. The method of claim 4, wherein the second agent is cyclosporine A.

60. The method of claim 5, wherein the second agent is cyclosporine A.

61. The method of claim 51, wherein the second agent is cyclosporine A.

62. The method of claim 56, wherein the second agent is cyclosporine A.

63. The method of claim 1, wherein the second agent is methotrexate.

64. The method of claim 2, wherein the second agent is methotrexate.

65. The method of claim 4, wherein the second agent is methotrexate.

66. The method of claim 5, wherein the second agent is methotrexate.

67. The method of claim 51, wherein the second agent is methotrexate.

68. The method of claim 56, wherein the second agent is methotrexate.

* * * * *

SEQUENCE LISTING

```
(1) GENERAL INFORMATION:

(iii) NUMBER OF SEQUENCES: 8

(2) INFORMATION FOR SEQ ID NO: 1:

(i) SEQUENCE CHARACTERISTICS:
         (A) LENGTH: 753 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..750

(ix) FEATURE:
         (A) NAME/KEY: sig_peptide
         (B) LOCATION: 1..84

(ix) FEATURE:
         (A) NAME/KEY: mat_peptide
         (B) LOCATION: 85..750

(ix) FEATURE:
         (A) NAME/KEY: misc_feature
         (B) LOCATION: 1..750
         (D) OTHER INFORMATION: /note= "Human transmembrane LFA-3"

(ix) FEATURE:
         (A) NAME/KEY: misc_feature
         (B) LOCATION: 646
         (D) OTHER INFORMATION: /note= "Transmembrane domain"

(xi) SEQUENCE DESCRIPTION: SEQ ID NO: 1:

ATG GTT GCT GGG AGC GAC GCG GGG CGG GCC CTG GGG GTC CTC AGC GTG      48
Met Val Ala Gly Ser Asp Ala Gly Arg Ala Leu Gly Val Leu Ser Val
-28             -25                 -20                 -15
```

```
GTC TGC CTG CTG CAC TGC TTT GGT TTC ATC AGC TGT TTT TCC CAA CAA       96
Val Cys Leu Leu His Cys Phe Gly Phe Ile Ser Cys Phe Ser Gln Gln
        -10                  -5                   1

ATA TAT GGT GTT GTG TAT GGG AAT GTA ACT TTC CAT GTA CCA AGC AAT      144
Ile Tyr Gly Val Val Tyr Gly Asn Val Thr Phe His Val Pro Ser Asn
  5                  10                  15                  20

GTG CCT TTA AAA GAG GTC CTA TGG AAA AAA CAA AAG GAT AAA GTT GCA      192
Val Pro Leu Lys Glu Val Leu Trp Lys Lys Gln Lys Asp Lys Val Ala
                 25                  30                  35

GAA CTG GAA AAT TCT GAA TTC AGA GCT TTC TCA TCT TTT AAA AAT AGG      240
Glu Leu Glu Asn Ser Glu Phe Arg Ala Phe Ser Ser Phe Lys Asn Arg
             40                  45                  50

GTT TAT TTA GAC ACT GTG TCA GGT AGC CTC ACT ATC TAC AAC TTA ACA      288
Val Tyr Leu Asp Thr Val Ser Gly Ser Leu Thr Ile Tyr Asn Leu Thr
         55                  60                  65

TCA TCA GAT GAA GAT GAG TAT GAA ATG GAA TCG CCA AAT ATT ACT GAT      336
Ser Ser Asp Glu Asp Glu Tyr Glu Met Glu Ser Pro Asn Ile Thr Asp
     70                  75                  80

ACC ATG AAG TTC TTT CTT TAT GTG CTT GAG TCT CTT CCA TCT CCC ACA      384
Thr Met Lys Phe Phe Leu Tyr Val Leu Glu Ser Leu Pro Ser Pro Thr
 85                  90                  95                 100

CTA ACT TGT GCA TTG ACT AAT GGA AGC ATT GAA GTC CAA TGC ATG ATA      432
Leu Thr Cys Ala Leu Thr Asn Gly Ser Ile Glu Val Gln Cys Met Ile
                105                 110                 115

CCA GAG CAT TAC AAC AGC CAT CGA GGA CTT ATA ATG TAC TCA TGG GAT      480
Pro Glu His Tyr Asn Ser His Arg Gly Leu Ile Met Tyr Ser Trp Asp
            120                 125                 130

TGT CCT ATG GAG CAA TGT AAA CGT AAC TCA ACC AGT ATA TAT TTT AAG      528
Cys Pro Met Glu Gln Cys Lys Arg Asn Ser Thr Ser Ile Tyr Phe Lys
        135                 140                 145

ATG GAA AAT GAT CTT CCA CAA AAA ATA CAG TGT ACT CTT AGC AAT CCA      576
Met Glu Asn Asp Leu Pro Gln Lys Ile Gln Cys Thr Leu Ser Asn Pro
    150                 155                 160

TTA TTT AAT ACA ACA TCA TCA ATC ATT TTG ACA ACC TGT ATC CCA AGC      624
Leu Phe Asn Thr Thr Ser Ser Ile Ile Leu Thr Thr Cys Ile Pro Ser
165                 170                 175                 180

AGC GGT CAT TCA AGA CAC AGA TAT GCA CTT ATA CCC ATA CCA TTA GCA      672
Ser Gly His Ser Arg His Arg Tyr Ala Leu Ile Pro Ile Pro Leu Ala
                185                 190                 195

GTA ATT ACA ACA TGT ATT GTG CTG TAT ATG AAT GGT ATT CTG AAA TGT      720
Val Ile Thr Thr Cys Ile Val Leu Tyr Met Asn Gly Ile Leu Lys Cys
            200                 205                 210

GAC AGA AAA CCA GAC AGA ACC AAC TCC AAT TGA                          753
Asp Arg Lys Pro Asp Arg Thr Asn Ser Asn
        215                 220
```

(2) INFORMATION FOR SEQ ID NO: 2:

(i) SEQUENCE CHARACTERISTICS:
        (A) LENGTH: 250 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Val Ala Gly Ser Asp Ala Gly Arg Ala Leu Gly Val Leu Ser Val
-28                 -25                 -20                 -15

Val Cys Leu Leu His Cys Phe Gly Phe Ile Ser Cys Phe Ser Gln Gln
        -10                  -5                   1
```

-continued

```
Ile Tyr Gly Val Val Tyr Gly Asn Val Thr Phe His Val Pro Ser Asn
 5               10                  15                  20

Val Pro Leu Lys Glu Val Leu Trp Lys Lys Gln Lys Asp Lys Val Ala
                25                  30                  35

Glu Leu Glu Asn Ser Glu Phe Arg Ala Phe Ser Ser Phe Lys Asn Arg
            40                  45                  50

Val Tyr Leu Asp Thr Val Ser Gly Ser Leu Thr Ile Tyr Asn Leu Thr
        55                  60                  65

Ser Ser Asp Glu Asp Glu Tyr Glu Met Glu Ser Pro Asn Ile Thr Asp
    70                  75                  80

Thr Met Lys Phe Phe Leu Tyr Val Leu Glu Ser Leu Pro Ser Pro Thr
85                  90                  95                  100

Leu Thr Cys Ala Leu Thr Asn Gly Ser Ile Glu Val Gln Cys Met Ile
                105                 110                 115

Pro Glu His Tyr Asn Ser His Arg Gly Leu Ile Met Tyr Ser Trp Asp
            120                 125                 130

Cys Pro Met Glu Gln Cys Lys Arg Asn Ser Thr Ser Ile Tyr Phe Lys
        135                 140                 145

Met Glu Asn Asp Leu Pro Gln Lys Ile Gln Cys Thr Leu Ser Asn Pro
    150                 155                 160

Leu Phe Asn Thr Thr Ser Ser Ile Ile Leu Thr Thr Cys Ile Pro Ser
165                 170                 175                 180

Ser Gly His Ser Arg His Arg Tyr Ala Leu Ile Pro Ile Pro Leu Ala
                185                 190                 195

Val Ile Thr Thr Cys Ile Val Leu Tyr Met Asn Gly Ile Leu Lys Cys
            200                 205                 210

Asp Arg Lys Pro Asp Arg Thr Asn Ser Asn
        215                 220
```

(2) INFORMATION FOR SEQ ID NO: 3:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..720

(ix) FEATURE:
        (A) NAME/KEY: sig_peptide
        (B) LOCATION: 1..84

(ix) FEATURE:
        (A) NAME/KEY: mat_peptide
        (B) LOCATION: 85..720

(ix) FEATURE:
        (A) NAME/KEY: misc_feature
        (B) LOCATION: 1..720
        (D) OTHER INFORMATION: /note= "Human PI-linked LFA-3"

(ix) FEATURE:
        (A) NAME/KEY: misc_feature
        (B) LOCATION: 568..720
        (D) OTHER INFORMATION: /note= "Signal sequence for
            PI-linkage"

(xi) SEQUENCE DESCRIPTION: SEQ ID NO: 3:

ATG GTT GCT GGG AGC GAC GCG GGG CGG GCC CTG GGG GTC CTC AGC GTG    48

-continued

```
Met Val Ala Gly Ser Asp Ala Gly Arg Ala Leu Gly Val Leu Ser Val
-28             -25                 -20                 -15

GTC TGC CTG CTG CAC TGC TTT GGT TTC ATC AGC TGT TTT TCC CAA CAA        96
Val Cys Leu Leu His Cys Phe Gly Phe Ile Ser Cys Phe Ser Gln Gln
            -10                 -5                   1

ATA TAT GGT GTT GTG TAT GGG AAT GTA ACT TTC CAT GTA CCA AGC AAT       144
Ile Tyr Gly Val Val Tyr Gly Asn Val Thr Phe His Val Pro Ser Asn
  5                  10                  15                  20

GTG CCT TTA AAA GAG GTC CTA TGG AAA AAA CAA AAG GAT AAA GTT GCA       192
Val Pro Leu Lys Glu Val Leu Trp Lys Lys Gln Lys Asp Lys Val Ala
                 25                  30                  35

GAA CTG GAA AAT TCT GAA TTC AGA GCT TTC TCA TCT TTT AAA AAT AGG       240
Glu Leu Glu Asn Ser Glu Phe Arg Ala Phe Ser Ser Phe Lys Asn Arg
                 40                  45                  50

GTT TAT TTA GAC ACT GTG TCA GGT AGC CTC ACT ATC TAC AAC TTA ACA       288
Val Tyr Leu Asp Thr Val Ser Gly Ser Leu Thr Ile Tyr Asn Leu Thr
                 55                  60                  65

TCA TCA GAT GAA GAT GAG TAT GAA ATG GAA TCG CCA AAT ATT ACT GAT       336
Ser Ser Asp Glu Asp Glu Tyr Glu Met Glu Ser Pro Asn Ile Thr Asp
         70                  75                  80

ACC ATG AAG TTC TTT CTT TAT GTG CTT GAG TCT CTT CCA TCT CCC ACA       384
Thr Met Lys Phe Phe Leu Tyr Val Leu Glu Ser Leu Pro Ser Pro Thr
 85                  90                  95                 100

CTA ACT TGT GCA TTG ACT AAT GGA AGC ATT GAA GTC CAA TGC ATG ATA       432
Leu Thr Cys Ala Leu Thr Asn Gly Ser Ile Glu Val Gln Cys Met Ile
                105                 110                 115

CCA GAG CAT TAC AAC AGC CAT CGA GGA CTT ATA ATG TAC TCA TGG GAT       480
Pro Glu His Tyr Asn Ser His Arg Gly Leu Ile Met Tyr Ser Trp Asp
                120                 125                 130

TGT CCT ATG GAG CAA TGT AAA CGT AAC TCA ACC AGT ATA TAT TTT AAG       528
Cys Pro Met Glu Gln Cys Lys Arg Asn Ser Thr Ser Ile Tyr Phe Lys
        135                 140                 145

ATG GAA AAT GAT CTT CCA CAA AAA ATA CAG TGT ACT CTT AGC AAT CCA       576
Met Glu Asn Asp Leu Pro Gln Lys Ile Gln Cys Thr Leu Ser Asn Pro
150                 155                 160

TTA TTT AAT ACA ACA TCA TCA ATC ATT TTG ACA ACC TGT ATC CCA AGC       624
Leu Phe Asn Thr Thr Ser Ser Ile Ile Leu Thr Thr Cys Ile Pro Ser
165                 170                 175                 180

AGC GGT CAT TCA AGA CAC AGA TAT GCA CTT ATA CCC ATA CCA TTA GCA       672
Ser Gly His Ser Arg His Arg Tyr Ala Leu Ile Pro Ile Pro Leu Ala
                185                 190                 195

GTA ATT ACA ACA TGT ATT GTG CTG TAT ATG AAT GGT ATG TAT GCT TTT       720
Val Ile Thr Thr Cys Ile Val Leu Tyr Met Asn Gly Met Tyr Ala Phe
                200                 205                 210

TAA                                                                   723
```

(2) INFORMATION FOR SEQ ID NO: 4:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Val Ala Gly Ser Asp Ala Gly Arg Ala Leu Gly Val Leu Ser Val
-28             -25                 -20                 -15

Val Cys Leu Leu His Cys Phe Gly Phe Ile Ser Cys Phe Ser Gln Gln
            -10                 -5                   1
```

```
Ile Tyr Gly Val Val Tyr Gly Asn Val Thr Phe His Val Pro Ser Asn
  5              10                  15                  20

Val Pro Leu Lys Glu Val Leu Trp Lys Lys Gln Lys Asp Lys Val Ala
             25                  30                  35

Glu Leu Glu Asn Ser Glu Phe Arg Ala Phe Ser Ser Phe Lys Asn Arg
         40                  45                  50

Val Tyr Leu Asp Thr Val Ser Gly Ser Leu Thr Ile Tyr Asn Leu Thr
     55                  60                  65

Ser Ser Asp Glu Asp Glu Tyr Glu Met Glu Ser Pro Asn Ile Thr Asp
     70                  75                  80

Thr Met Lys Phe Phe Leu Tyr Val Leu Glu Ser Leu Pro Ser Pro Thr
85                   90                  95                  100

Leu Thr Cys Ala Leu Thr Asn Gly Ser Ile Glu Val Gln Cys Met Ile
                105                 110                 115

Pro Glu His Tyr Asn Ser His Arg Gly Leu Ile Met Tyr Ser Trp Asp
                120                 125                 130

Cys Pro Met Glu Gln Cys Lys Arg Asn Ser Thr Ser Ile Tyr Phe Lys
             135                 140                 145

Met Glu Asn Asp Leu Pro Gln Lys Ile Gln Cys Thr Leu Ser Asn Pro
150                 155                 160

Leu Phe Asn Thr Thr Ser Ser Ile Ile Leu Thr Thr Cys Ile Pro Ser
165                 170                 175                 180

Ser Gly His Ser Arg His Arg Tyr Ala Leu Ile Pro Ile Pro Leu Ala
                185                 190                 195

Val Ile Thr Thr Cys Ile Val Leu Tyr Met Asn Gly Met Tyr Ala Phe
                200                 205                 210

(2) INFORMATION FOR SEQ ID NO: 5:

(i) SEQUENCE CHARACTERISTICS:
        (A) LENGTH: 1056 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1053

(ix) FEATURE:
        (A) NAME/KEY: sig_peptide
        (B) LOCATION: 1..72

(ix) FEATURE:
        (A) NAME/KEY: mat_peptide
        (B) LOCATION: 73..1053

(ix) FEATURE:
        (A) NAME/KEY: misc_feature
        (B) LOCATION: 1..1053
        (D) OTHER INFORMATION: /note= "Human CD2"

(ix) FEATURE:
        (A) NAME/KEY: misc_feature
        (B) LOCATION: 628..702
        (D) OTHER INFORMATION: /note= "Transmembrane domain"

(xi) SEQUENCE DESCRIPTION: SEQ ID NO: 5:

ATG AGC TTT CCA TGT AAA TTT GTA GCC AGC TTC CTT CTG ATT TTC AAT      48
Met Ser Phe Pro Cys Lys Phe Val Ala Ser Phe Leu Leu Ile Phe Asn
-24             -20                 -15                 -10

GTT TCT TCC AAA GGT GCA GTC TCC AAA GAG ATT ACG AAT GCC TTG GAA      96
```

```
                Val Ser Ser Lys Gly Ala Val Ser Lys Glu Ile Thr Asn Ala Leu Glu
                         -5                   1                   5

ACC TGG GGT GCC TTG GGT CAG GAC ATC AAC TTG GAC ATT CCT AGT TTT                144
Thr Trp Gly Ala Leu Gly Gln Asp Ile Asn Leu Asp Ile Pro Ser Phe
         10                  15                  20

CAA ATG AGT GAT GAT ATT GAC GAT ATA AAA TGG GAA AAA ACT TCA GAC                192
Gln Met Ser Asp Asp Ile Asp Asp Ile Lys Trp Glu Lys Thr Ser Asp
 25              30                  35                  40

AAG AAA AAG ATT GCA CAA TTC AGA AAA GAG AAA GAG ACT TTC AAG GAA                240
Lys Lys Lys Ile Ala Gln Phe Arg Lys Glu Lys Glu Thr Phe Lys Glu
                 45                  50                  55

AAA GAT ACA TAT AAG CTA TTT AAA AAT GGA ACT CTG AAA ATT AAG CAT                288
Lys Asp Thr Tyr Lys Leu Phe Lys Asn Gly Thr Leu Lys Ile Lys His
             60                  65                  70

CTG AAG ACC GAT GAT CAG GAT ATC TAC AAG GTA TCA ATA TAT GAT ACA                336
Leu Lys Thr Asp Asp Gln Asp Ile Tyr Lys Val Ser Ile Tyr Asp Thr
         75                  80                  85

AAA GGA AAA AAT GTG TTG GAA AAA ATA TTT GAT TTG AAG ATT CAA GAG                384
Lys Gly Lys Asn Val Leu Glu Lys Ile Phe Asp Leu Lys Ile Gln Glu
     90                  95                 100

AGG GTC TCA AAA CCA AAG ATC TCC TGG ACT TGT ATC AAC ACA ACC CTG                432
Arg Val Ser Lys Pro Lys Ile Ser Trp Thr Cys Ile Asn Thr Thr Leu
105             110                 115                 120

ACC TGT GAG GTA ATG AAT GGA ACT GAC CCC GAA TTA AAC CTG TAT CAA                480
Thr Cys Glu Val Met Asn Gly Thr Asp Pro Glu Leu Asn Leu Tyr Gln
                125                 130                 135

GAT GGG AAA CAT CTA AAA CTT TCT CAG AGG GTC ATC ACA CAC AAG TGG                528
Asp Gly Lys His Leu Lys Leu Ser Gln Arg Val Ile Thr His Lys Trp
            140                 145                 150

ACC ACC AGC CTG AGT GCA AAA TTC AAG TGC ACA GCA GGG AAC AAA GTC                576
Thr Thr Ser Leu Ser Ala Lys Phe Lys Cys Thr Ala Gly Asn Lys Val
        155                 160                 165

AGC AAG GAA TCC AGT GTC GAG CCT GTC AGC TGT CCA GAG AAA GGT CTG                624
Ser Lys Glu Ser Ser Val Glu Pro Val Ser Cys Pro Glu Lys Gly Leu
170                 175                 180

GAC ATC TAT CTC ATC ATT GGC ATA TGT GGA GGA GGC AGC CTC TTG ATG                672
Asp Ile Tyr Leu Ile Ile Gly Ile Cys Gly Gly Gly Ser Leu Leu Met
185                 190                 195                 200

GTC TTT GTG GCA CTG CTC GTT TTC TAT ATC ACC AAA AGG AAA AAA CAG                720
Val Phe Val Ala Leu Leu Val Phe Tyr Ile Thr Lys Arg Lys Lys Gln
                205                 210                 215

AGG AGT CGG AGA AAT GAT GAG GAG CTG GAG ACA AGA GCC CAC AGA GTA                768
Arg Ser Arg Arg Asn Asp Glu Glu Leu Glu Thr Arg Ala His Arg Val
            220                 225                 230

GCT ACT GAA GAA AGG GGC CGG AAG CCC CAC CAA ATT CCA GCT TCA ACC                816
Ala Thr Glu Glu Arg Gly Arg Lys Pro His Gln Ile Pro Ala Ser Thr
        235                 240                 245

CCT CAG AAT CCA GCA ACT TCC CAA CAT CCT CCT CCA CCT GGT CAT                    864
Pro Gln Asn Pro Ala Thr Ser Gln His Pro Pro Pro Pro Gly His
    250                 255                 260

CGT TCC CAG GCA CCT AGT CAT CGT CCC CCG CCT CCT GGA CAC CGT GTT                912
Arg Ser Gln Ala Pro Ser His Arg Pro Pro Pro Pro Gly His Arg Val
265                 270                 275                 280

CAG CAC CAG CCT CAG AAG AGG CCT CCT GCT CCG TCG GGC ACA CAA GTT                960
Gln His Gln Pro Gln Lys Arg Pro Pro Ala Pro Ser Gly Thr Gln Val
                285                 290                 295

CAC CAG CAG AAA GGC CCG CCC CTC CCC AGA CCT CGA GTT CAG CCA AAA               1008
His Gln Gln Lys Gly Pro Pro Leu Pro Arg Pro Arg Val Gln Pro Lys
            300                 305                 310
```

```
CCT CCC CAT GGG GCA GCA GAA AAC TCA TTG TCC CCT TCC TCT AAT    1053
Pro Pro His Gly Ala Ala Glu Asn Ser Leu Ser Pro Ser Ser Asn
        315                 320                 325

TAA                                                              1056
```

(2) INFORMATION FOR SEQ ID NO: 6:

(i) SEQUENCE CHARACTERISTICS:
        (A) LENGTH: 351 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ser Phe Pro Cys Lys Phe Val Ala Ser Phe Leu Ile Phe Asn
-24             -20             -15             -10

Val Ser Ser Lys Gly Ala Val Ser Lys Glu Ile Thr Asn Ala Leu Glu
            -5              1               5

Thr Trp Gly Ala Leu Gly Gln Asp Ile Asn Leu Asp Ile Pro Ser Phe
        10              15              20

Gln Met Ser Asp Asp Ile Asp Asp Ile Lys Trp Glu Lys Thr Ser Asp
 25              30              35                      40

Lys Lys Lys Ile Ala Gln Phe Arg Lys Glu Lys Glu Thr Phe Lys Glu
            45              50                      55

Lys Asp Thr Tyr Lys Leu Phe Lys Asn Gly Thr Leu Lys Ile Lys His
            60              65                      70

Leu Lys Thr Asp Asp Gln Asp Ile Tyr Lys Val Ser Ile Tyr Asp Thr
            75              80              85

Lys Gly Lys Asn Val Leu Glu Lys Ile Phe Asp Leu Lys Ile Gln Glu
     90              95              100

Arg Val Ser Lys Pro Lys Ile Ser Trp Thr Cys Ile Asn Thr Thr Leu
105             110             115                     120

Thr Cys Glu Val Met Asn Gly Thr Asp Pro Glu Leu Asn Leu Tyr Gln
                125             130              135

Asp Gly Lys His Leu Lys Leu Ser Gln Arg Val Ile Thr His Lys Trp
            140             145             150

Thr Thr Ser Leu Ser Ala Lys Phe Lys Cys Thr Ala Gly Asn Lys Val
        155             160             165

Ser Lys Glu Ser Ser Val Glu Pro Val Ser Cys Pro Glu Lys Gly Leu
    170             175             180

Asp Ile Tyr Leu Ile Ile Gly Ile Cys Gly Gly Ser Leu Leu Met
185             190             195                 200

Val Phe Val Ala Leu Leu Val Phe Tyr Ile Thr Lys Arg Lys Lys Gln
            205             210             215

Arg Ser Arg Arg Asn Asp Glu Glu Leu Glu Thr Arg Ala His Arg Val
        220             225             230

Ala Thr Glu Glu Arg Gly Arg Lys Pro His Gln Ile Pro Ala Ser Thr
        235             240             245

Pro Gln Asn Pro Ala Thr Ser Gln His Pro Pro Pro Pro Gly His
    250             255             260

Arg Ser Gln Ala Pro Ser His Arg Pro Pro Pro Gly His Arg Val
265             270             275             280

Gln His Gln Pro Gln Lys Arg Pro Pro Ala Pro Ser Gly Thr Gln Val
            285             290             295

His Gln Gln Lys Gly Pro Pro Leu Pro Arg Pro Arg Val Gln Pro Lys
```

-continued

```
                  300                 305                 310
         Pro Pro His Gly Ala Ala Glu Asn Ser Leu Ser Pro Ser Ser Asn
             315                 320                 325
```

(2) INFORMATION FOR SEQ ID NO: 7:

(i) SEQUENCE CHARACTERISTICS:
        (A) LENGTH: 1050 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1041

(ix) FEATURE:
        (A) NAME/KEY: sig-peptide
        (B) LOCATION: 1..84

(ix) FEATURE:
        (A) NAME/KEY: mat_peptide
        (B) LOCATION: 85..1041

(ix) FEATURE:
        (A) NAME/KEY: misc-feature
        (B) LOCATION: 85..1041
        (D) OTHER INFORMATION: /note- "LFA3TIP"

(ix) FEATURE:
        (A) NAME/KEY: misc-feature
        (B) LOCATION: 360..361
        (D) OTHER INFORMATION: /note- "LFA-3/IgG fusion point"

(xi) SEQUENCE DESCRIPTION: SEQ ID NO: 7:

```
ATG GTT GCT GGG AGC GAC GCG GGG CGG GCC CTG GGG GTC CTC AGC GTG        48
Met Val Ala Gly Ser Asp Ala Gly Arg Ala Leu Gly Val Leu Ser Val
-28         -25                 -20                 -15

GTC TGC CTG CTG CAC TGC TTT GGT TTC ATC AGC TGT TTT TCC CAA CAA        96
Val Cys Leu Leu His Cys Phe Gly Phe Ile Ser Cys Phe Ser Gln Gln
        -10                  -5                   1

ATA TAT GGT GTT GTG TAT GGG AAT GTA ACT TTC CAT GTA CCA AGC AAT       144
Ile Tyr Gly Val Val Tyr Gly Asn Val Thr Phe His Val Pro Ser Asn
  5                  10                  15                  20

GTG CCT TTA AAA GAG GTC CTA TGG AAA AAA CAA AAG GAT AAA GTT GCA       192
Val Pro Leu Lys Glu Val Leu Trp Lys Lys Gln Lys Asp Lys Val Ala
             25                  30                  35

GAA CTG GAA AAT TCT GAA TTC AGA GCT TTC TCA TCT TTT AAA AAT AGG       240
Glu Leu Glu Asn Ser Glu Phe Arg Ala Phe Ser Ser Phe Lys Asn Arg
                 40                  45                  50

GTT TAT TTA GAC ACT GTG TCA GGT AGC CTC ACT ATC TAC AAC TTA ACA       288
Val Tyr Leu Asp Thr Val Ser Gly Ser Leu Thr Ile Tyr Asn Leu Thr
             55                  60                  65

TCA TCA GAT GAA GAT GAG TAT GAA ATG GAA TCG CCA AAT ATT ACT GAT       336
Ser Ser Asp Glu Asp Glu Tyr Glu Met Glu Ser Pro Asn Ile Thr Asp
 70                  75                  80

ACC ATG AAG TTC TTT CTT TAT GTC GAC AAA ACT CAC ACA TGC CCA CCG       384
Thr Met Lys Phe Phe Leu Tyr Val Asp Lys Thr His Thr Cys Pro Pro
 85                  90                  95                 100

TGC CCA GCA CCT GAA CTC CTG GGG GGA CCG TCA GTC TTC CTC TTC CCC       432
Cys Pro Ala Pro Glu Leu Leu Gly Gly Pro Ser Val Phe Leu Phe Pro
                105                 110                 115

CCA AAA CCC AAG GAC ACC CTC ATG ATC TCC CGG ACC CCT GAG GTC ACA       480
Pro Lys Pro Lys Asp Thr Leu Met Ile Ser Arg Thr Pro Glu Val Thr
            120                 125                 130
```

```
TGC GTG GTG GTG GAC GTG AGC CAC GAA GAC CCT GAG GTC AAG TTC AAC        528
Cys Val Val Val Asp Val Ser His Glu Asp Pro Glu Val Lys Phe Asn
        135                 140                 145

TGG TAC GTG GAC GGC GTG GAG GTG CAT AAT GCC AAG ACA AAG CCG CGG        576
Trp Tyr Val Asp Gly Val Glu Val His Asn Ala Lys Thr Lys Pro Arg
    150                 155                 160

GAG GAG CAG TAC AAC AGC ACG TAC CGG GTG GTC AGC GTC CTC ACC GTC        624
Glu Glu Gln Tyr Asn Ser Thr Tyr Arg Val Val Ser Val Leu Thr Val
165                 170                 175                 180

CTG CAC CAG GAC TGG CTG AAT GGC AAG GAG TAC AAG TGC AAG GTC TCC        672
Leu His Gln Asp Trp Leu Asn Gly Lys Glu Tyr Lys Cys Lys Val Ser
                185                 190                 195

AAC AAA GCC CTC CCA GCC CCC ATC GAG AAA ACC ATC TCC AAA GCC AAA        720
Asn Lys Ala Leu Pro Ala Pro Ile Glu Lys Thr Ile Ser Lys Ala Lys
            200                 205                 210

GGG CAG CCC CGA GAA CCA CAG GTG TAC ACC CTG CCC CCA TCC CGG GAT        768
Gly Gln Pro Arg Glu Pro Gln Val Tyr Thr Leu Pro Pro Ser Arg Asp
        215                 220                 225

GAG CTG ACC AAG AAC CAG GTC AGC CTG ACC TGC CTG GTC AAA GGC TTC        816
Glu Leu Thr Lys Asn Gln Val Ser Leu Thr Cys Leu Val Lys Gly Phe
    230                 235                 240

TAT CCC AGC GAC ATC GCC GTG GAG TGG GAG AGC AAT GGG CAG CCG GAG        864
Tyr Pro Ser Asp Ile Ala Val Glu Trp Glu Ser Asn Gly Gln Pro Glu
245                 250                 255                 260

AAC AAC TAC AAG ACC ACG CCT CCC GTG CTG GAC TCC GAC GGC TCC TTC        912
Asn Asn Tyr Lys Thr Thr Pro Pro Val Leu Asp Ser Asp Gly Ser Phe
                265                 270                 275

TTC CTC TAC AGC AAG CTC ACC GTG GAC AAG AGC AGG TGG CAG CAG GGG        960
Phe Leu Tyr Ser Lys Leu Thr Val Asp Lys Ser Arg Trp Gln Gln Gly
            280                 285                 290

AAC GTC TTC TCA TGC TCC GTG ATG CAT GAG GCT CTG CAC AAC CAC TAC       1008
Asn Val Phe Ser Cys Ser Val Met His Glu Ala Leu His Asn His Tyr
        295                 300                 305

ACG CAG AAG AGC CTC TCC CTG TCT CCG GGT AAA TGAGTGCGG                 1050
Thr Gln Lys Ser Leu Ser Leu Ser Pro Gly Lys
    310                 315

(2) INFORMATION FOR SEQ ID NO: 8:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO: 8:

Met Val Ala Gly Ser Asp Ala Gly Arg Ala Leu Gly Val Leu Ser Val
-28             -25                 -20                 -15

Val Cys Leu Leu His Cys Phe Gly Phe Ile Ser Cys Phe Ser Gln Gln
            -10                 -5                  1

Ile Tyr Gly Val Val Tyr Gly Asn Val Thr Phe His Val Pro Ser Asn
  5                  10                  15                  20

Val Pro Leu Lys Glu Val Leu Trp Lys Lys Gln Lys Asp Lys Val Ala
            25                  30                  35

Glu Leu Glu Asn Ser Glu Phe Arg Ala Phe Ser Ser Phe Lys Asn Arg
        40                  45                  50

Val Tyr Leu Asp Thr Val Ser Gly Ser Leu Thr Ile Tyr Asn Leu Thr
    55                  60                  65
```

-continued

```
Ser Ser Asp Glu Asp Glu Tyr Glu Met Glu Ser Pro Asn Ile Thr Asp
     70                  75                  80

Thr Met Lys Phe Phe Leu Tyr Val Asp Lys Thr His Thr Cys Pro Pro
 85                  90                  95                 100

Cys Pro Ala Pro Glu Leu Leu Gly Gly Pro Ser Val Phe Leu Phe Pro
            105                 110                 115

Pro Lys Pro Lys Asp Thr Leu Met Ile Ser Arg Thr Pro Glu Val Thr
            120                 125                 130

Cys Val Val Val Asp Val Ser His Glu Asp Pro Glu Val Lys Phe Asn
            135                 140                 145

Trp Tyr Val Asp Gly Val Glu Val His Asn Ala Lys Thr Lys Pro Arg
        150                 155                 160

Glu Glu Gln Tyr Asn Ser Thr Tyr Arg Val Val Ser Val Leu Thr Val
165                 170                 175                 180

Leu His Gln Asp Trp Leu Asn Gly Lys Glu Tyr Lys Cys Lys Val Ser
            185                 190                 195

Asn Lys Ala Leu Pro Ala Pro Ile Glu Lys Thr Ile Ser Lys Ala Lys
            200                 205                 210

Gly Gln Pro Arg Glu Pro Gln Val Tyr Thr Leu Pro Pro Ser Arg Asp
        215                 220                 225

Glu Leu Thr Lys Asn Gln Val Ser Leu Thr Cys Leu Val Lys Gly Phe
230                 235                 240

Tyr Pro Ser Asp Ile Ala Val Glu Trp Glu Ser Asn Gly Gln Pro Glu
245                 250                 255                 260

Asn Asn Tyr Lys Thr Thr Pro Pro Val Leu Asp Ser Asp Gly Ser Phe
            265                 270                 275

Phe Leu Tyr Ser Lys Leu Thr Val Asp Lys Ser Arg Trp Gln Gln Gly
            280                 285                 290

Asn Val Phe Ser Cys Ser Val Met His Glu Ala Leu His Asn His Tyr
            295                 300                 305

Thr Gln Lys Ser Leu Ser Leu Ser Pro Gly Lys
        310                 315
```